(12) United States Patent
Dow et al.

(10) Patent No.: US 11,400,152 B2
(45) Date of Patent: Aug. 2, 2022

(54) COMPOSITIONS AND METHODS FOR ENHANCING INNATE IMMUNITY IN A SUBJECT FOR TREATMENT OF INFECTIONS AND CANCER AND OTHER ACUTE AND CHRONIC CONDITIONS OF THE EYE

(71) Applicant: Colorado State University Research Foundation, Fort Collins, CO (US)

(72) Inventors: Steven Dow, Littleton, CO (US); Kathryn Wotman, Livermore, CO (US); Lyndah Chow, Fort Collins, CO (US)

(73) Assignee: COLORADO STATE UNIVERSITY RESEARCH FOUNDATION, Fort Collins, CO (US)

( * ) Notice: Subject to any disclaimer, the term of this patent is extended or adjusted under 35 U.S.C. 154(b) by 171 days.

(21) Appl. No.: 16/670,785

(22) Filed: Oct. 31, 2019

(65) Prior Publication Data
US 2020/0069795 A1 Mar. 5, 2020

Related U.S. Application Data

(63) Continuation-in-part of application No. 15/476,723, filed on Mar. 31, 2017, now Pat. No. 10,512,687.

(60) Provisional application No. 62/456,505, filed on Feb. 8, 2017, provisional application No. 62/316,985, filed on Apr. 1, 2016, provisional application No. 62/316,986, filed on Apr. 1, 2016.

(51) Int. Cl.
| | | |
|---|---|---|
| A61K 8/14 | (2006.01) | |
| A61K 39/39 | (2006.01) | |
| C12N 15/117 | (2010.01) | |
| A61K 47/69 | (2017.01) | |
| A61K 9/00 | (2006.01) | |
| A61K 9/127 | (2006.01) | |
| A61P 37/02 | (2006.01) | |
| A61K 39/12 | (2006.01) | |
| A61K 49/00 | (2006.01) | |
| A61K 39/00 | (2006.01) | |

(52) U.S. Cl.
CPC ............ *A61K 39/39* (2013.01); *A61K 8/14* (2013.01); *A61K 9/0019* (2013.01); *A61K 9/0043* (2013.01); *A61K 9/1272* (2013.01); *A61K 39/12* (2013.01); *A61K 47/6911* (2017.08); *A61P 37/02* (2018.01); *C12N 15/117* (2013.01); *A61K 49/0054* (2013.01); *A61K 49/0084* (2013.01); *A61K 2039/53* (2013.01); *A61K 2039/543* (2013.01); *A61K 2039/545* (2013.01); *A61K 2039/552* (2013.01); *A61K 2039/555* (2013.01); *A61K 2039/55511* (2013.01); *A61K 2039/55516* (2013.01); *A61K 2039/55555* (2013.01); *A61K 2039/55561* (2013.01); *A61K 2039/57* (2013.01); *C12N 2710/16034* (2013.01)

(58) Field of Classification Search
CPC ...... A61K 2039/55555; A61K 2039/53; A61K 39/39; A61K 39/12; A61K 2039/543; A61K 2039/57; A61K 2039/55561; A61K 2039/545; A61K 2039/552; A61K 2039/55511; A61K 2039/55516; A61K 35/68

See application file for complete search history.

(56) References Cited

U.S. PATENT DOCUMENTS

| | | | |
|---|---|---|---|
| 6,251,678 B1 | 6/2001 | Volkin et al. | |
| 10,512,687 B2 * | 12/2019 | Dow | A61P 37/02 |
| 2005/0013812 A1 | 1/2005 | Dow et al. | |
| 2010/0297165 A1 | 11/2010 | Berzofsky et al. | |
| 2011/0070298 A1 | 3/2011 | Mansour et al. | |

FOREIGN PATENT DOCUMENTS

| | | |
|---|---|---|
| WO | 2008057696 | 5/2008 |
| WO | 2010060030 | 5/2010 |
| WO | 2014204791 A1 | 12/2014 |
| WO | 2016161309 A1 | 10/2016 |
| WO | 2019054960 A2 | 3/2019 |

OTHER PUBLICATIONS

Contreras et al. Effects of a liposome-TLR mucosal immune stimulant on kittens infected with feline herpesvirus 1. J Vet Int Med 31(4): 1312, Jun. 2017.*

Contreras et al. Evaluaton of liposome toll-like receptor ligand complexes for non-specific mucosal immunoprotection from feline herpesvirus-1 infection. J Vet Int Med 33: 831-837, 2019.*

Dow et al. Activation of innate immune responses in cat leukocytes by a liposomal TLR ligand immune stimulant. J Vet Int Med 31(4): 1308, #IM05, Jun. 2017.*

(Continued)

*Primary Examiner* — Bridget E Bunner
(74) *Attorney, Agent, or Firm* — Polsinelli PC

(57) ABSTRACT

Embodiments of the present invention generally relate to novel immunostimulatory compositions of use to stimulate non-specific immune responses in a subject. In certain embodiments, immunogenic compositions disclosed herein can be directed to use in the eye of a subject. In some embodiments, the immunogenic compositions disclosed herein enhance non-specific immune responses in the eye of a subject to treat or reduce the risk of onset of an eye condition. In other embodiments, compositions disclosed herein can be used to treat eye infections due to a microorganism, tumors of the eye, as well as, chronic wounds of the eye.

20 Claims, 37 Drawing Sheets
Specification includes a Sequence Listing.

(56) References Cited

OTHER PUBLICATIONS

Logue et al. Treatment with cationic liposome-DNA complexes (CLDCs) protects mice from lethal Western equine encephalitis virus (WEEV) challgenge. Antiviral Res 87: 195-203, 2010.*
Wheat et al. Local immune and microbiological responses to mucosal administration of a liposome-TLR agonist immunotherapeutic in dogs. BMC Vet Res 15: 330, 2019.*
Wheat et al. Activation of upper respiratory tract mucosal innate immune responses in cats by liposomal toll-like receptor ligand complexes delivered topically. J Vet Int Med 33: 838-845, 2019.*
Wheat et al. Non-specific protection from respiratory tract infections in cattle generated by intranasal administration of an innate immune response. PLoS One 15(6): e0235422, 2020.*
Bal et al. Co-encapsulation of antigen and Toll-like receptor ligand in cationic liposomes affects the quality of the immune response in mice after intradermal vaccination. Vaccine 29: 1045-1052, 2011.
Diwan et al. Enhancement of immune responses by co-delivery of a CpG oligodeoxynucleotide and tetanus toxoid in biodegradable nanospheres. J Controlled Release 85: 247-262, 2002.
Dow et al. Liposome-nucleic acid immunotherapeutics. Expert Opin Drug Delivery 5(1): 11-24, 2008.
Graciotti et al. The era of bioengineering: how will this affect the next generation of cancer immunotherapy? J Transl Med 15: 142, 2017.
Kawakami et al. Effect of hydrophilic polymers on physical stability of liposome dispersions. J Phys Chern B 105: 2374-2385, 2001.
Lee et al. Biodegradable nanoparticles containing TLR3 or TLR9 agonists together with antigen enhance MHC-restricted presentation of the antigen. Arch Pharm Res 33(11): 1859-1866, 2010.
Milicic et al. Small cationic DDA:TDB liposomes as protein vaccine adjuvants obviate the need for TLR agonists in inducing cellular and humoral responses. PLoS One 7(3): e34255, 2012.
Patel et al. Novel drugs targeting Toll-like receptors for antiviral therapy. Future Virol 9(9): 811-829, 2014.
Suzuki et al. Liposome-encapsulated CpG oligonucleotides as a potent adjuvant for inducing Type 1 innate immunity. Cancer Res 64: 8754-8760, 2004.

Temizoz et al. Vaccine adjuvants as potential cancer immunotherapeutics. Int Immunol 28(7): 329-338, 2016.
Uematsu et al. Toll-like receptors (TLRs) and their ligands. "Toll-like receptors (TLRs) and Innate Immunity" in Handbook of Experimental Pharmacology 183: 1-20, 2008.
Wong et al. Activation of toll-like receptor signaling pathway for protection against influenza virus infection. Vaccine 27: 3481-3483, 2009.
Zaks et al. Efficient immunization and cross-priming by vaccine adjuvants containing TLR3 or TLR9 agonists complexed to cationic liposomes. J Immunol 176: 7335-7345, 2006.
Chang et al., "A novel vaccine adjuvant for recombinant flu antigens", Biologicals, Jun. 2009, vol. 37, Issue 3, pp. 141-147.
Luo et al., "Plasmid DNA containing multiple CpG motifs triggers a strong immune response to hepatitis B surface antigen when combined with incomplete Freund's adjuvant but not aluminum hydroxide", Molecular Medicine Reports, Sep. 12, 2012, pp. 1309-1314.
Park et al., "Construction of CpG motif-enriched DNA vaccine plasmids for enhanced early immune response", Biotechnology and Bioprocess Engineering, Feb. 2005, vol. 10, pp. 29-33.
Lievens et al., "Evaluation of an Enhanced Viscosity Artificial Tear for Moderate to Severe Dry Eye Disease: A Multicenter, Double-masked, Randomized 30-day Study", Contact Lens and Anterior Eye, 2019, vol. 42, pp. 443-449.
Stiles, "Ocular Manifestations of Feline Viral Diseases", Veterinary Journal, 2014, vol. 201, pp. 166-173.
Gowen et al., "Prophylaxis with cationic liposome-DNA complexes protects hamsters from phleboviral disease importance of liposomal delivery and CpG motifs", Antiviral Res, 2009, vol. 81, pp. 37-46.
Grossman et al., "Enhancement of the priming efficacy of DNA vaccines encoding dendritic cell-targeted antigens by synergistic toll-like receptor ligands", BMC Immunol, 2009, vol. 10, No. 43, 10 pages.
Henderson et al., "Mucosal immunization with liposome-nucleic acid adjuvants generates effective humoral and cellular immunity", Vaccine, 2011, vol. 29, pp. 5304-5312.

\* cited by examiner

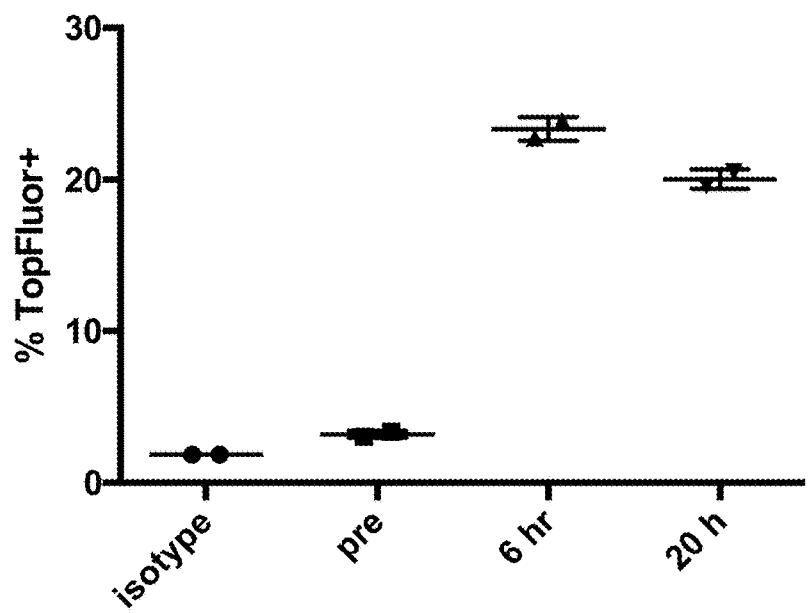
Fig. 13A (labeled MIM uptake by nasal lavage cells)
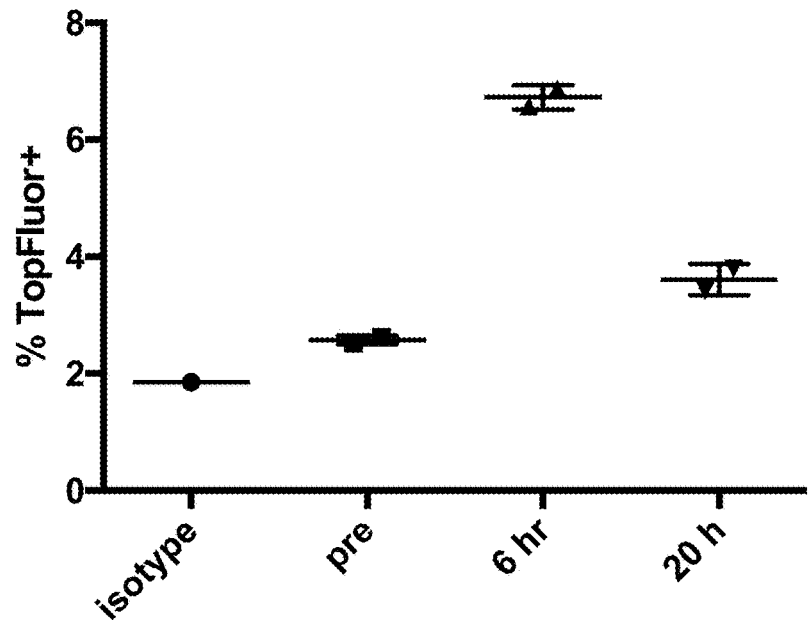
Fig. 13B (labeled MIM uptake by throat swab cells)

Fig. 14A (Neutrophil infiltrate into nose)
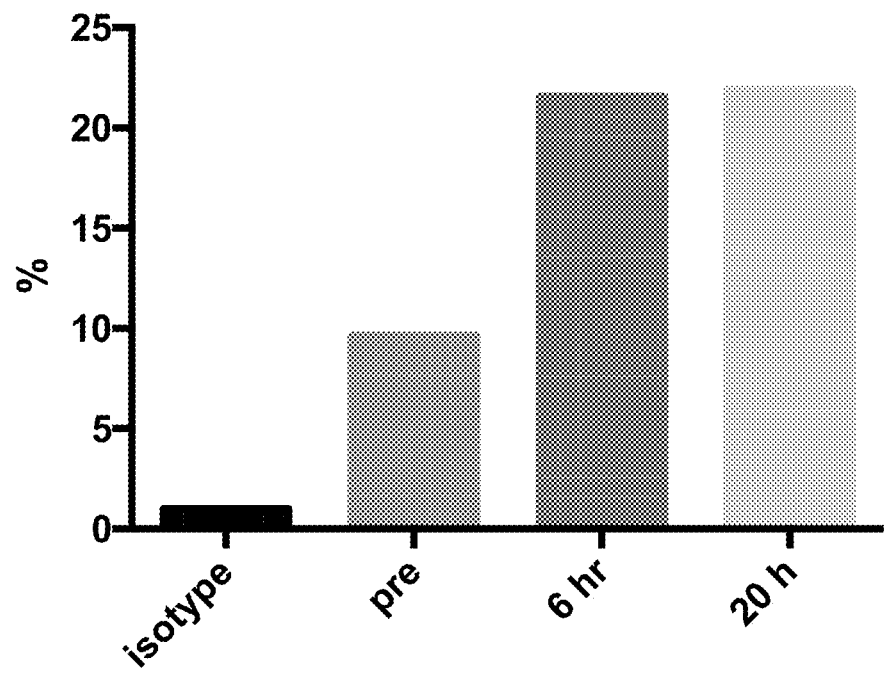
Fig. 14B (Monocyte infiltrate into throat)
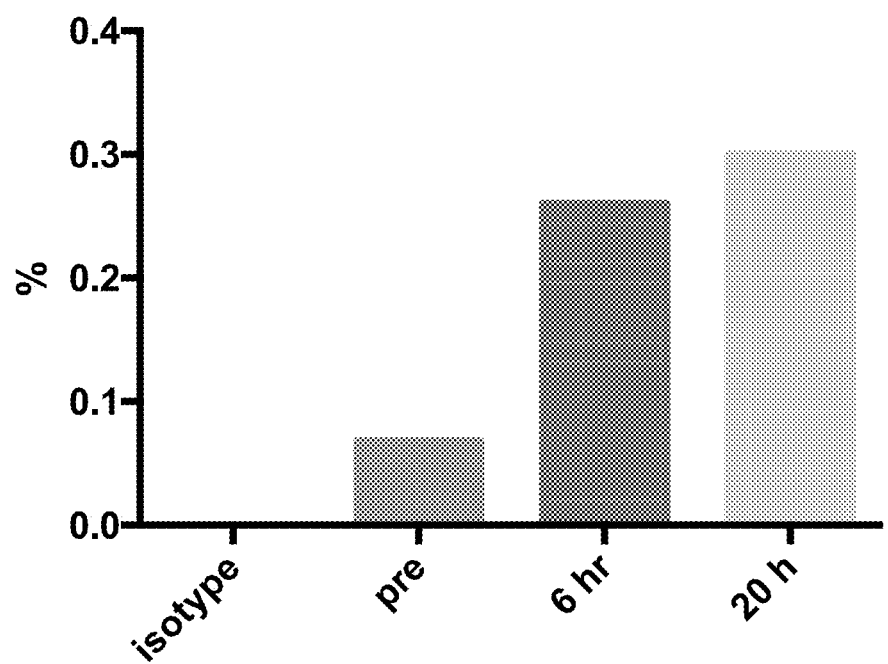

Fig. 15A (CD4 T cell infiltration: nasal lavage)
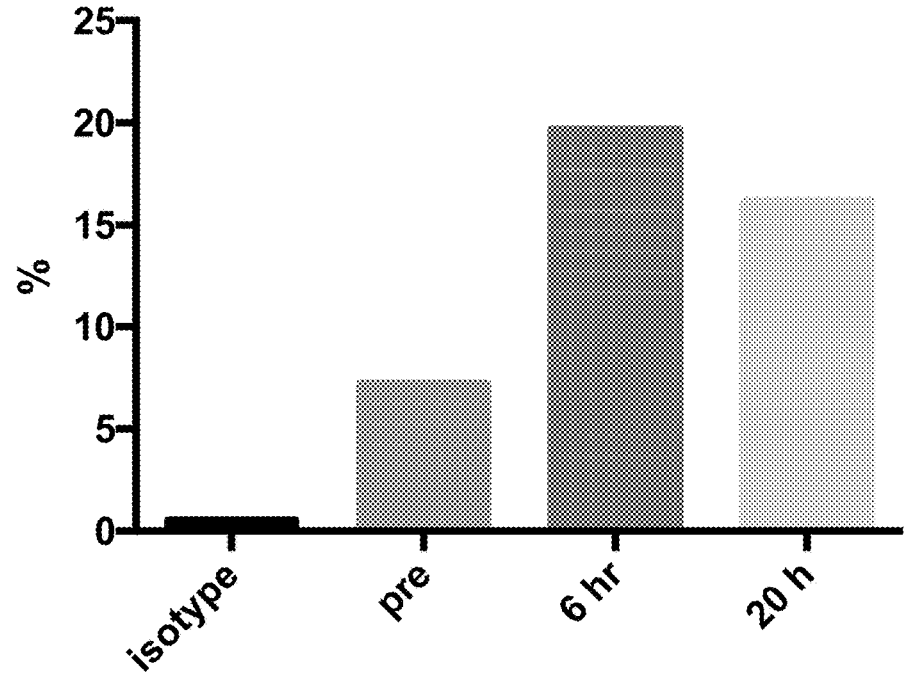
Fig. 15B (CD4 T cell infiltration: throat swabs)
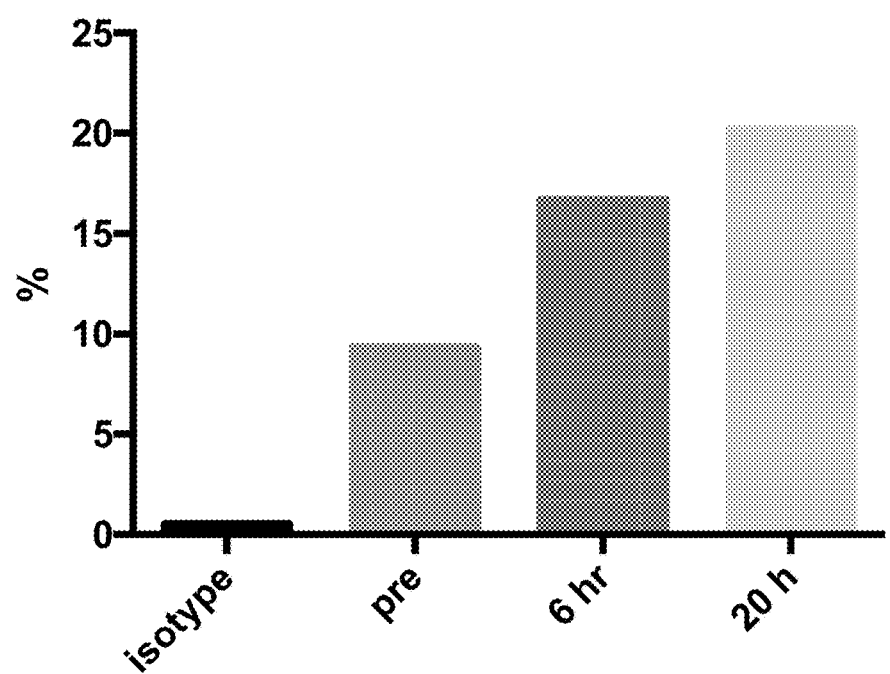

Monocyte infiltration after MIM
% CD14+

MFI MHCII on CD14+

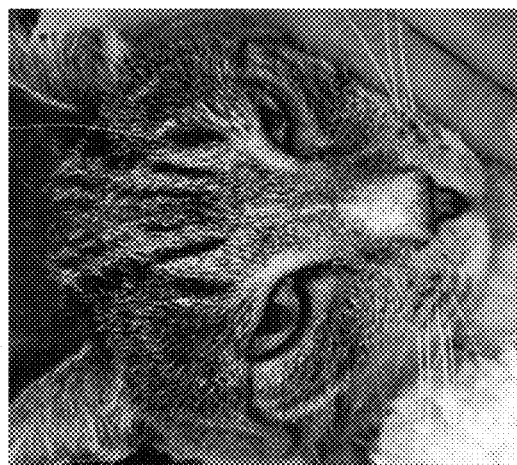
Fig. 35A (Pre-treatment)
Fig. 35B (4 days after Rx)

(Pre-treatment)

(Week 2)

(Week 4)

(Week 6)

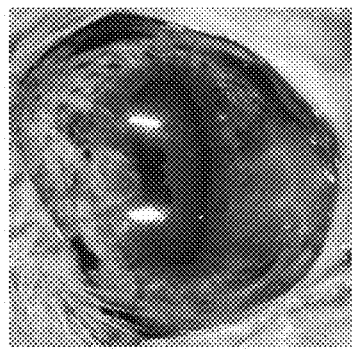 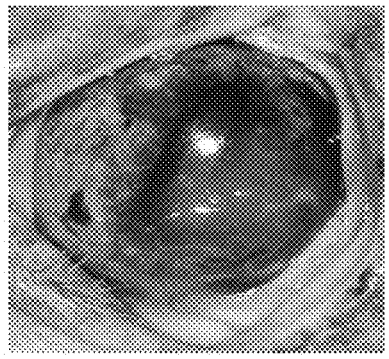 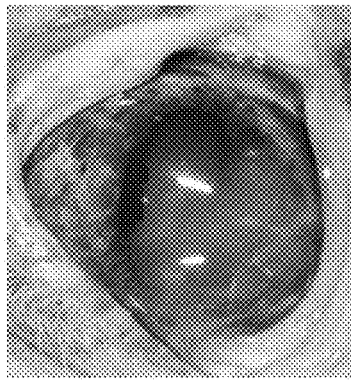 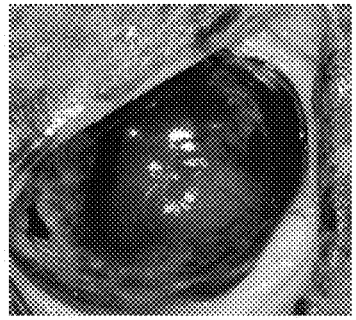
Fig. 37A  Fig. 37B  Fig. 37C  Fig. 37D
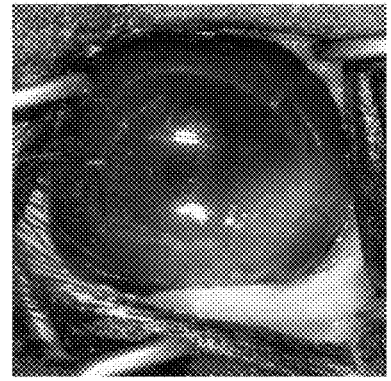 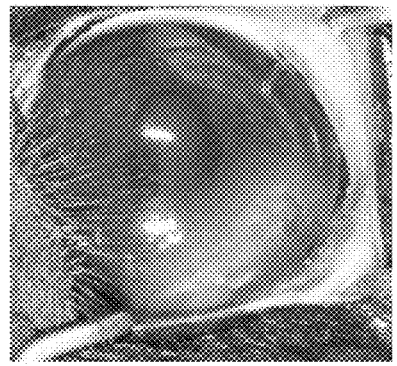 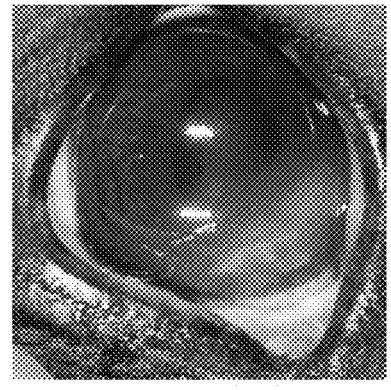 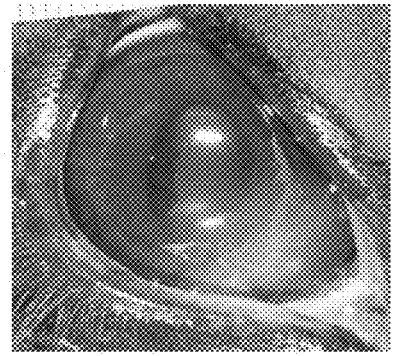
Pre-treatment, Topical only  2 weeks, Topical only  4 weeks, Topical only  6 weeks, Topical only

SEQUENCE LISTING

```
<160> NUMBER OF SEQ ID NOS: 2

<210> SEQ ID NO 1
<211> LENGTH: 2152
<212> TYPE: DNA
<213> ORGANISM: Artificial Sequence
<220> FEATURE:
<223> OTHER INFORMATION: Non-coding plasmid DNA and TLR3 agonist

<400> SEQUENCE: 1
taccctgaat tcatttcact tgcgactttg gctgcttttt gtatggtgaa ggatgcgccc        60
```

```
tggcgcgcat acacagcaca tctctttgca ggaaaaaaac gctgtgaaaa atgttggttt    120
tatcggctgg cgcggaatgg tcggctctgt tctcatgcaa cgcatggtag aggagcgcga    180
tttcgacgct attcgccctg tttctttttc tacctcccag tttggacagg cggcgcccac    240
cttcggcgac acctccaccg gcacgctaca ggacgctttt gatctggatg cgctaaaagc    300
gctcgatatc atcgtgacct gccagggcgg cgattatacc aacgaaattt atccaaagct    360
gcgcgaaagc ggatggcagg gttactggat tgatgcggct tctacgctgc gcatgaaaga    420
tgatgccatt attattctcg acccggtcaa ccaggacgtg attaccgacg gcctgaacaa    480
tggcgtgaag acctttgtgg gcggtaactg taccgttagc ctgatgttga tgtcgctggg    540
cggtctcttt gcccataatc tcgttgactg ggtatccgtc gcgacctatc aggccgcctc    600
cggcggcggc gcgcgccata tgcgcgagct gttaacccag atgggtcagt tgtatggcca    660
tgtcgccgat gaactggcga cgccgtcttc cgcaattctt gatattgaac gcaaagttac    720
ggcattgacc cgcagcggcg agctgccggt tgataacttt ggcgtaccgc tggcgggaag    780
cctgatcccc tggatcgaca aacagctcga taacggccag agccgcgaag agtggaaagg    840 ccagcggaa accaacaaga ttctcaatac tgcctctgtg attccggttg atggtttgtg    900
tgtgcgcgtc ggcgcgctgc gctgtcacag ccaggcgttc accatcaagc tgaaaaaaga    960
ggtatccatt ccgacggtgg aagaactgct ggcggcacat aatccgtggg cgaaagtggt    1020
gccgaacgat cgtgatatca ctatgcgcga attaaccccg gcggcggtga ccggcacgtt    1080
gactacgccg gttggtcgtc tgcgtaagct gaacatgggg ccagagttct tgtcggcgtt    1140
taccgtaggc gaccagttgt tatggggcgc cgccgagccg ctgcgtcgaa tgctgcgcca    1200
gttggcgtag tggctaataa aacgaaaggc tcagtcgaaa gactgggcct ttcgttttat    1260
gtcgactcgt cgttgtcgtt ttgtcgttag cttagctgcc aatcgttaag gtgcatcgat    1320 gcagggggc tgaattgcag tctatttgcg tcgtcgtttt gtcgttttgt cgttacgttc    1380
cggaagtcaa tcgattcgtc gttaacgtta acgctatgcc tccgatgcga atcagtctcg    1440
tcgttgtcgt tgtcgttcca tgctttacgt actactgctc gtcgctgttg tcgtttcttg    1500 tccacccta agggccatct tcgtcgttgt cgttttgtcg ttctgattag tcccaatgct    1560
cgtggtgcat cgatgcaggg gggcgtaaac ctgctgaatc ggactcgtcg ttttgtcgtt    1620
ttgtcgttga tggccagctt taccatgact cgtcgttaac gttaacgcta tttactgatc    1680
ctgggatcca gtcgtcgttg tcgttgtcgt tatgccaagc tgccaatgtt tatcgtcgct    1740
gttgtcgttt cttgatatcc cggttgtcag ccgttaagtg ttcctgtgtc actcaaaatt    1800
gctttgagag gctctaaggg cttctcagtg cgttacatcc ctggcttgtt gtccacaacc    1860
gttaaacctt aaaagcttta aaagccttat atattctttt ttttcttata aaacttaaaa    1920
ccttagaggc tatttaagtt gctgatttat attaattta ttgttcaaac atgagagctt    1980
agtacgtgaa acatgagagc ttagtacgtt agccatgaga gcttagtacg ttagccatga    2040
gggtttagtt cgttaaacat gagagcttag tacgttaaac ttgagagctt agtacgtgaa    2100
acatgagagc ttagtacgta ctatcaacag gttgaactgc gaattctcag at           2152
```

```
<210> SEQ ID NO 2
<211> LENGTH: 11
<212> TYPE: PRT
<213> ORGANISM: Artificial Sequence
<220> FEATURE:
<223> OTHER INFORMATION: a polycationic polymer polypeptide

<400> SEQUENCE: 2

Lys Leu Lys Leu Leu Leu Leu Leu Lys Leu Lys
1               5                   10
```

COMPOSITIONS AND METHODS FOR ENHANCING INNATE IMMUNITY IN A SUBJECT FOR TREATMENT OF INFECTIONS AND CANCER AND OTHER ACUTE AND CHRONIC CONDITIONS OF THE EYE

PRIORITY

This continuation-in-part application claims priority to U.S. Non-Provisional application Ser. No. 15/476,723 filed Mar. 31, 2017 which claim priority to U.S. Provisional Application No. 62/456,505 filed Feb. 8, 2017 entitled "Mucosal immune stimulant for eliciting non-specific protection from viral and bacterial pathogens," U.S. Provisional Application No. 62/316,986 filed Apr. 1, 2016 entitled "Enhanced Liposomal Immunotherapeutic for Vaccination," and U.S. Provisional Application No. 62/316,985 filed Apr. 1, 2016 and entitled "Compositions and Methods for Stimulating Mucosal Innate Immune Response," each of these applications is hereby incorporated by reference in their entirety for all purposes under 35 U.S.C. § 119(e).

FIELD OF THE INVENTION

Embodiments of the instant disclosure relate to novel immunostimulatory compositions, adjuvants and vaccines, and their use to stimulate immune responses and treat or reduce the risk of onset of a condition and/or infection. In certain embodiments, immunogenic compositions disclosed herein can be directed to use in the eye of a subject. In some embodiments, the immunogenic compositions disclosed herein enhance immune responses in the eye of humans or other mammals such as pets, livestock, zoo animals, and wild animals. In other embodiments, compositions disclosed herein can be used to treat eye infections due to a microorganism, tumors of the eye, as well as, chronic wounds of the eye or chronic conditions such as non-healing corneal ulcers.

BACKGROUND OF THE INVENTION

There is a growing need for new approaches for generating non-specific protection from viral and bacterial infections without having to resort to the use of antibiotics or other antimicrobial drugs, which serve to stimulate the development of antibiotic resistance. Currently however there are few immunostimulatory compounds that are capable of eliciting rapid and sustained activation of innate immune responses at mucosal surfaces such as the nasopharynx, upper respiratory tract, eye conditions, GI tract, and reproductive tract to generate protection from infection. There is a need in the art for novel compositions and methods to enhance innate immune responses; for example, at mucosal surfaces for non-specific protection from infections, as well as to increase the efficacy of existing vaccines.

BRIEF SUMMARY OF THE INVENTION

In certain embodiments disclosed herein, immunogenic compositions including at least one of (a) cationic liposomes, at least one (b) toll like receptor (TLR) or mixture thereof, and at least one (c) cellular adhesion agent. In certain embodiments, the TLRs include but are not limited to TLR3 and TLR9 ligands. In other embodiments, the cationic liposomes can include, but are not limited to, a mixture of cationic lipid and non-charged lipids. In accordance with these embodiments, a mixture of cationic lipid and non-charged lipids can include a mixture of DOTAP and cholesterol. In certain embodiments, the DOTAP and cholesterol can be about a 1:1 molar ratio or about a 2:1 or about a 1:2 or similar ratio. In some embodiments, the mixture of cationic lipid and non-charged lipids can include at least one of non-coding plasmid DNA and polyI:C. In other embodiments, the non-coding plasmid DNA can include a polynucleotide represented by the nucleic acid sequence, SEQ ID NO. 1. In yet other aspects, the mixture of cationic lipid and non-charged lipids can include plasmid DNA and polyI:C in about a 1:1 ratio (by weight) or about a 2:1 or about a 1:2 or similar ratio. In certain embodiments, the cellular adhesion agent can be a low- to mid-weight viscosity carboxymethylcellulose. In certain embodiments, the low molecular weight cellular adhesion agent can be carboxymethylcellulose. In some embodiments, carboxymethylcellulose can be present in an immunogenic composition disclosed herein at about 1% to about 20% (v/v). Certain immunogenic compositions disclosed herein can include complexes of the cationic liposomes and any TLR 3 and TLR 9 ligands known in the art. According to further aspects, the complexes include about 10 to about 200 μg TLR ligands per milliliter cationic liposomes. In certain embodiments, cationic liposomes can be present at about 1 to about 20 mM concentration in an immunogenic composition disclosed herein. In certain alternative embodiments, the immunogenic composition can further include an antigen. In some embodiments, the antigen can be a protein antigen. In other embodiment, the antigen can be derived from a virus, bacterium, prion, fungus, a toxin, a tumor-related antigen or other protein or non-protein antigen.

In other embodiments, methods for inducing an innate immune response in a subject are disclosed. In certain embodiments, methods are disclosed for inducing an innate immune response in a subject having an infection or other condition. In accordance with these embodiments, methods can include, but are not limited to, providing to a subject an effective amount of an immunogenic composition disclosed herein. In certain embodiments, the immunogenic composition can include: (a) cationic liposomes; (b) one or more TLR ligands (e.g. a mixture of toll like receptor 3 (TLR3) and toll like receptor 9 (TLR9) ligands); and/or (c) a cellular adhesion agent. In certain aspects, the subject can be a human, a pet, livestock, bird, fish or other animal. In further aspects, the composition can be provided to an animal prior to and/or during boarding. According the further aspects, the subject can be a horse, a dog, a cat, a cow, sheep, a pig, a goat, a chicken, a zoo animal, a wild animal and a fish. In even further aspects, an infection is from a virus or bacterium or fungus, prion or protozoan. In certain aspects, the condition is a respiratory infection. In accordance with these embodiments, an immunogenic composition can include a polynucleotide represented by SEQ ID NO. 1 and the ligand polyI:C.

In some embodiments, an immunogenic composition disclosed herein can be provided to the subject within 24 hours prior to the risk of exposure and/or within 24 hours to a week or more after exposure, during early onset of clinical signs of an infection, or during chronic infection. In accordance with these embodiments, the immunogenic composition is capable of inducing a local, non-specific immune response at a site of administration. In certain embodiments, immunogenic compositions disclosed herein can be administered to the subject at the site of a wound, an infection or other condition or alternatively, administered to induced a systemic non-specific immune response. In certain subjects, immunogenic compositions disclosed herein can be administered to the reproductive tract, the gastrointestinal tract, the mammary gland, to gills, to air sacs, to eyes, to ears, and to the nose of a subject in need of such a treatment. In yet further aspects, the composition can be administered without the concurrent administration of a vaccine or other known agent for the treatment or reducing onset of a condition.

Further disclosed herein is a method for inducing an immune response to an antigen in a subject, including providing to the subject a composition including: (a) cationic liposomes; (b) a mixture of toll like receptor 3 (TLR3) and toll like receptor 9 (TLR9) ligands; (c) a cellular adhesion agent and the antigen. According to certain aspects, the composition can be administered to the subject orally, nasally, intranasally, topically, intradermally, subcutaneously, intra-vaginally, by uterine or intra-mammary injection, by aerosol delivery, by delivery in water, or parenterally.

In other embodiments, an immunogenic composition can be used to treat a subject having an adverse eye condition. In accordance with these embodiments, an eye condition can include but are not limited to, an infection, a tumor, an eye injury, chronic wound or ulcer or similar condition of the eye thereof. In accordance with these embodiments, the eye condition can include a condition that affects the cornea or retina or other component of the eye, such as the adnexa of the eye. Certain embodiments of the invention can include administering an immunogenic composition disclosed herein to the eye of a subject to reduce incidence of blindness or loss of eyes or vision or to treat an infection or injury of the eye. In some embodiments, an infection of the eye can be caused by a virus, bacterium, fungus, prion or other microorganism. In certain embodiments, the infection can be caused by a Herpesvirus or other microorganism capable of causing an eye infection. In some embodiments, the infection can be a chronic viral infection of the eye of a subject. In certain embodiments, the eye condition can include an infection of the cornea, adverse condition of the cornea or outer service of the eye. In other embodiments, the infection can involve the adnexa of the eye such as the conjunctiva and sclera, which can further involve cancer (e.g. squamous cell carcinoma) or chronic infection (e.g., herpesvirus infection, mycoplasma infection, calicivirus infection)

In other embodiments, an immunogenic composition disclosed herein can be used to treat cancer of the eye. In accordance with these embodiments, the immunogenic composition of use to treat an eye condition can include, but is not limited to, at least one cationic liposome agent, at least one TLR agonist and at least one ocular adhesive agent. In some embodiments, the adhesive agent can be carboxymethyl cellulose, chitosan, a polyglycol, or a hyaluronic acid like agent. In certain embodiments, the immunogenic composition of use to treat the eye of a subject can include a liposome and dual TLR (e.g. TLR 3 and TLR9 agonist) composition along with and a high molecular weight/high viscosity adhesive agent. In some embodiments, the high molecular weight/high viscosity adhesive agent can include, but is not limited to, high viscosity carboxymethylcellulose (CMC). In some embodiments, high viscosity CMC is about 1500 to about 3000 centipoise (cps). In certain embodiments, cancer of the eye can include cancers of any part of the eye. In other embodiments, cancer of the eye can include a squamous cell carcinoma (e.g. of the cornea or other component of the eye). In accordance with these embodiments, immunogenic compositions disclosed herein of use to treat a condition of the eye can provide broad spectrum activity of increased duration, reducing frequency of treatment and having reduced side effects. In certain embodiments, the immunogenic compositions disclosed herein can reduce the incidence of irritation and inflammation as well as treat chronic eye conditions with improved outcomes.

In certain embodiments, immunogenic compositions disclosed herein are formulated for prolonged administration to the eye of a subject, reducing frequency of application to a site of infection and/or condition. In some embodiments, immunogenic formulations disclosed herein are specifically designed for topical administration to the eye. In some embodiments, an immunogenic formulation of use for topical administration includes cationic liposomes, a mixture of TLR3 and TLR9 agonists and an adhesive agent. In accordance with these embodiments, an essentially liquid immunogenic formulation disclosed herein further comprises a high molecular weight and/or high viscosity adhesion agent. In certain embodiments, the high molecular weight/high viscosity adhesion agent includes, but is not limited to, carboxymethylcellulose (CMC). In other embodiments, a high molecular weight/high viscosity CMC solution is combined with an essentially liquid immunogenic formulation disclosed herein at a predetermined ratio. In accordance with these embodiments, these formulations will have increased viscosity to a gel-like consistency to increase contact time in an affected area (e.g. the eye).

While multiple embodiments are disclosed, still other embodiments of the disclosure will become apparent to those skilled in the art from the following detailed description, which shows and describes illustrative embodiments of the disclosed apparatus, systems and methods. As will be realized, the disclosed apparatus, systems and methods are capable of modifications in various obvious aspects, all without departing from the spirit and scope of the disclosure. Accordingly, the drawings and detailed description are to be regarded as illustrative in nature and not restrictive.

BRIEF DESCRIPTION OF THE DRAWINGS

FIG. 7B illustrates exemplary flow cytometry data demonstrating oropharyngeal cells from cats treated with an immunogenic composition (e.g., PCT-01: CLDC+CMC) of some embodiments disclosed herein.

FIG. 13A illustrates exemplary data quantifying the uptake of an immunogenic composition (e.g., PCT-01: CLDC+CMC) by nasal lavage cells in a healthy dog. FIG. 13B illustrates exemplary data quantifying the update of an immunogenic composition (e.g., PCT-01: CLDC+CMC) by oropharyngeal cells following intranasal and oral administration in a healthy dog of some embodiments disclosed herein.

FIGS. 14A and 14B illustrates exemplary data quantifying the increase in immune cell infiltrates in the nose (FIG. 14A) and throat (FIG. 14B) of dogs following an immunogenic composition (e.g., PCT-01: CLDC+CMC) treatment of some embodiments disclosed herein.

FIGS. 15A and 15B illustrates exemplary data quantifying stimulation of CD4+ T-cell infiltrates in canine nasal lavage cells and throat of the canine following treatment with an immunogenic composition (e.g., PCT-01: MIM: CLDC+CMC) treatment of some embodiments disclosed herein.

MIM: CLDC+CMC) intranasal delivery in goats of some embodiments disclosed herein.

Figure 31:
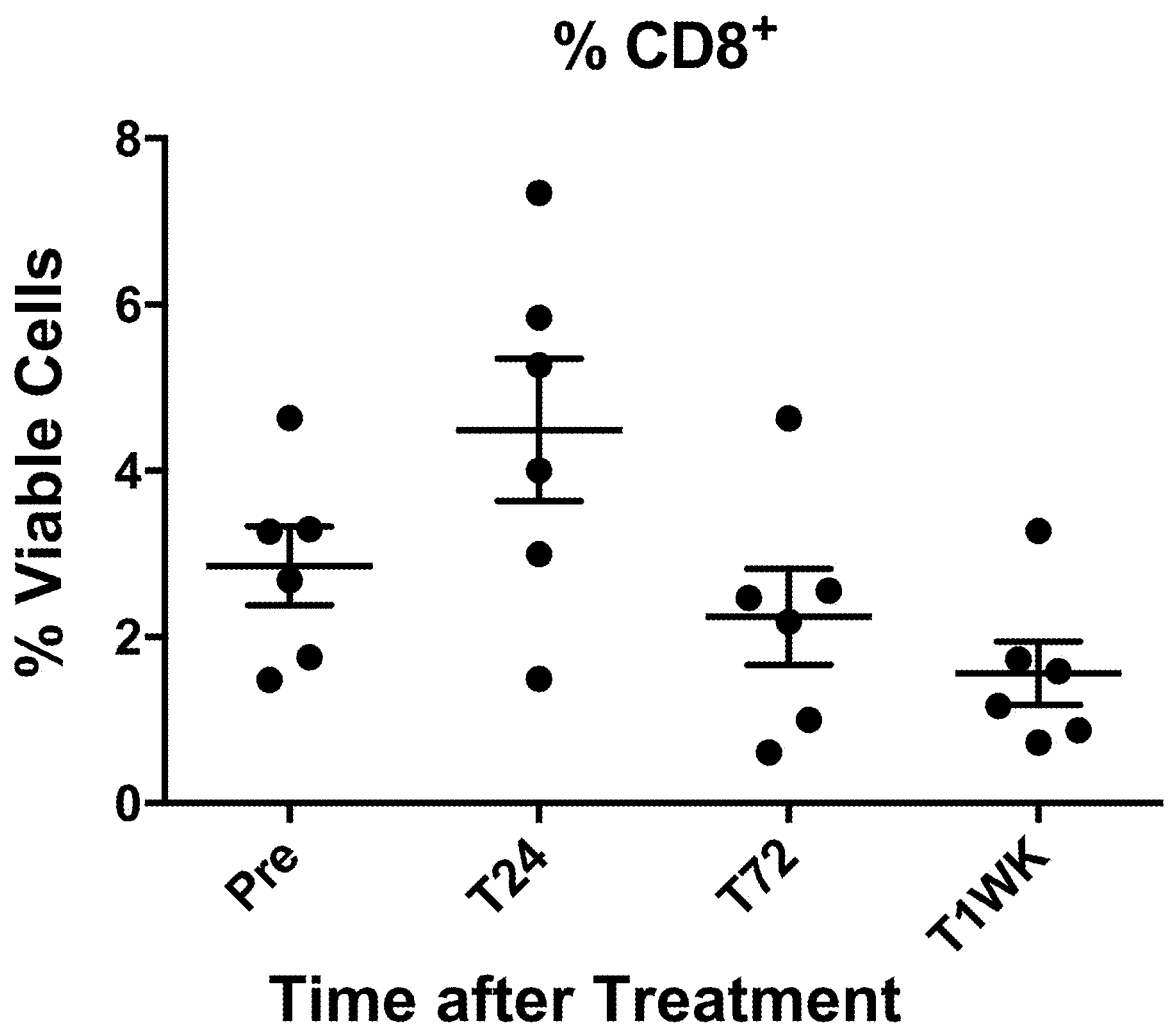

FIG. 31 illustrates an exemplary cell count data demonstrating recruitment of $CD8^+$ T cells into nasopharynx of goats by an immunogenic composition (e.g., PCT-01: MIM: CLDC+CMC) intranasal administration of some embodiments disclosed herein.

Figure 32:
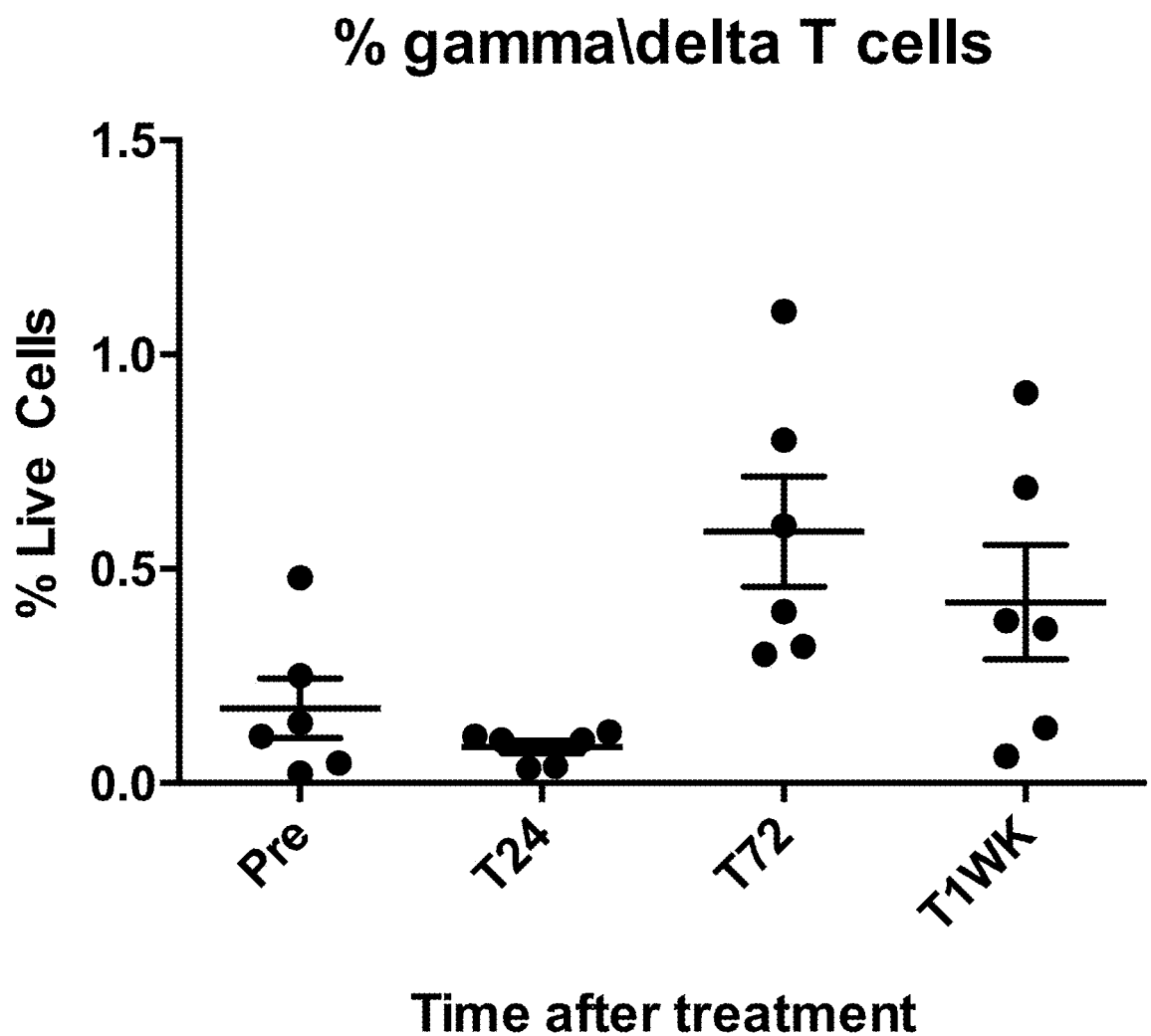

FIG. 32 illustrates an exemplary in vitro expansion of γδ-T cells in goat PBMC cultures following an immunogenic composition (e.g., PCT-01: MIM: CLDC+CMC) stimulation of some embodiments disclosed herein.

Figure 33:
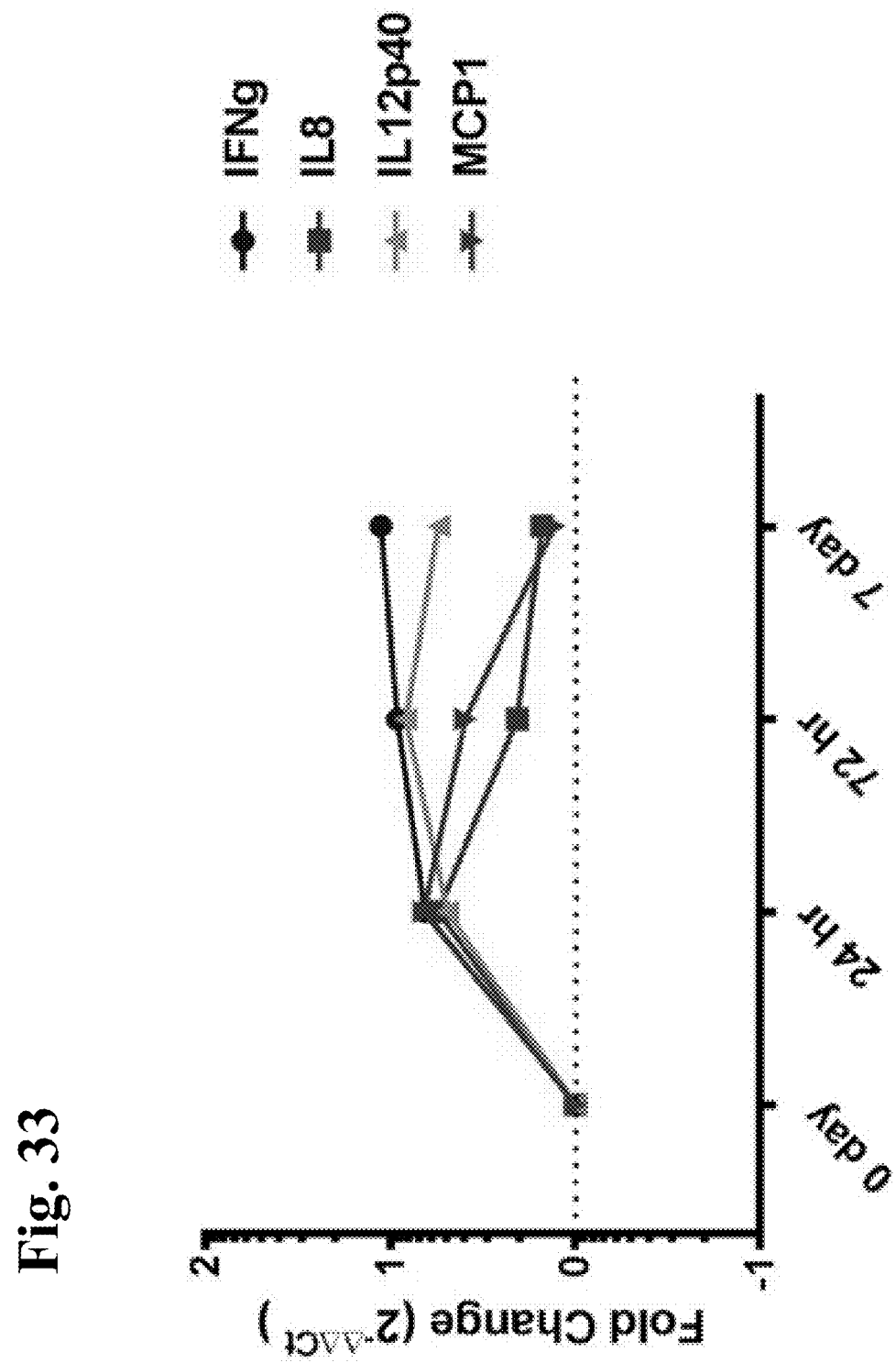

FIG. 33 illustrates an exemplary in vivo induction of mucosal immune responses in the oropharynx of dogs treated orally with an immunogenic composition (e.g., PCT-01: MIM: CLDC+CMC) of some embodiments disclosed herein.

Figure 34:
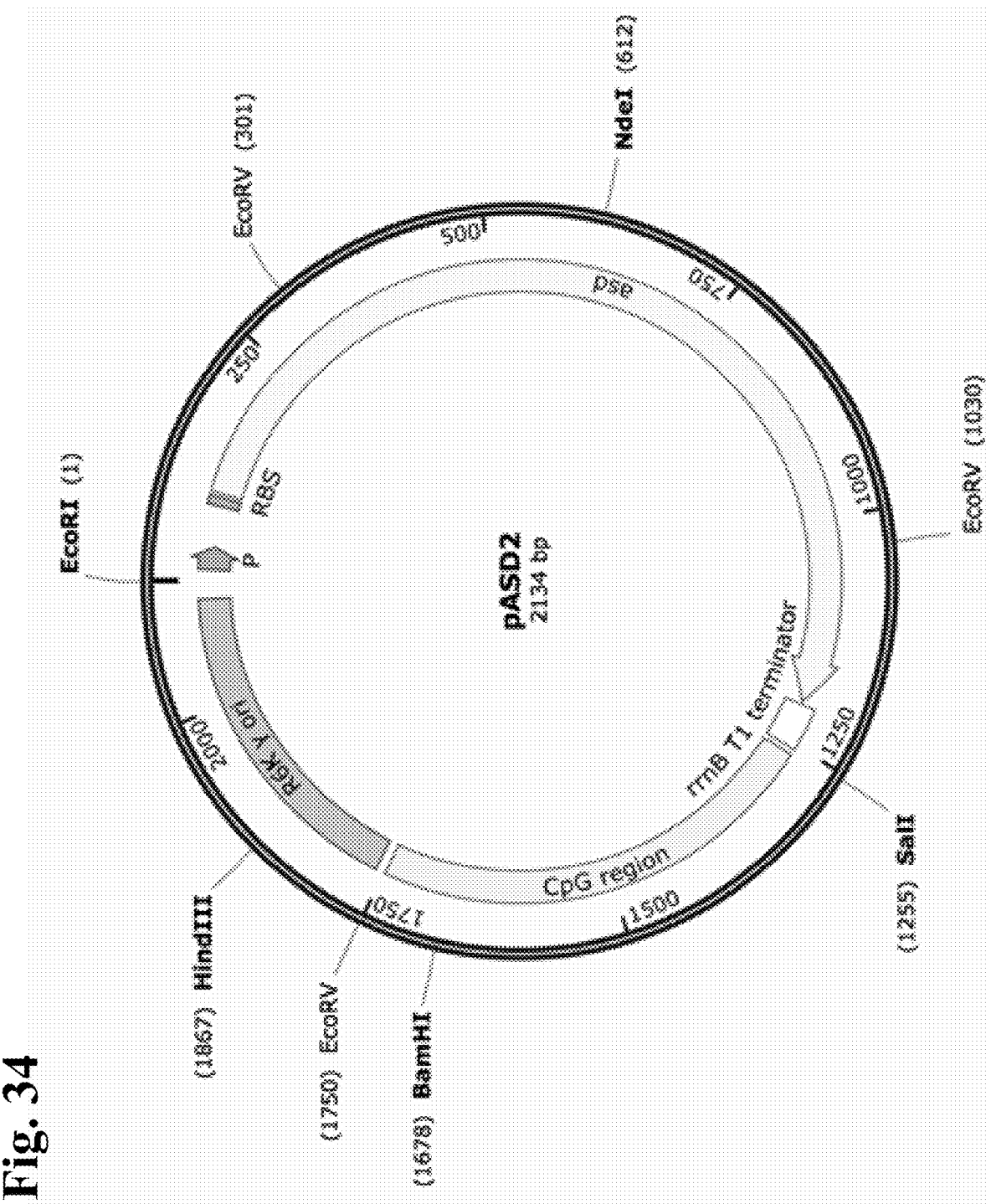

FIG. 34 illustrates an exemplary plasmid map of a TLR9 agonist, according to certain embodiments disclosed herein.

FIGS. 35A and 35B illustrate an exemplary response to certain immunogenic compositions disclosed herein in an animal model having a viral infection of the eye before and after treatment according to certain embodiments of the instant invention.

Figure 36A:
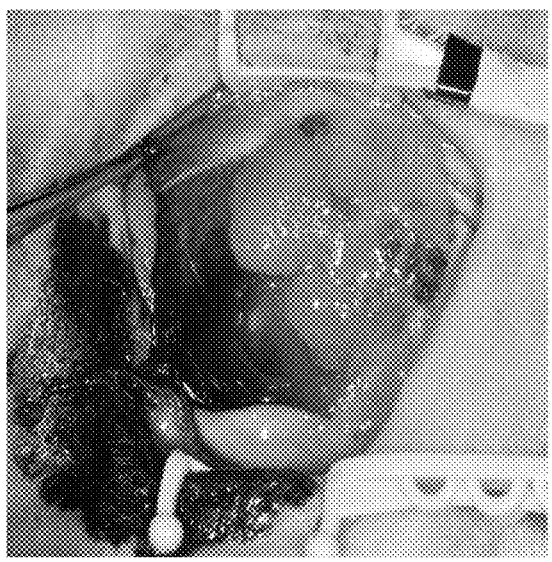
Figure 36B:
Figure 36C:
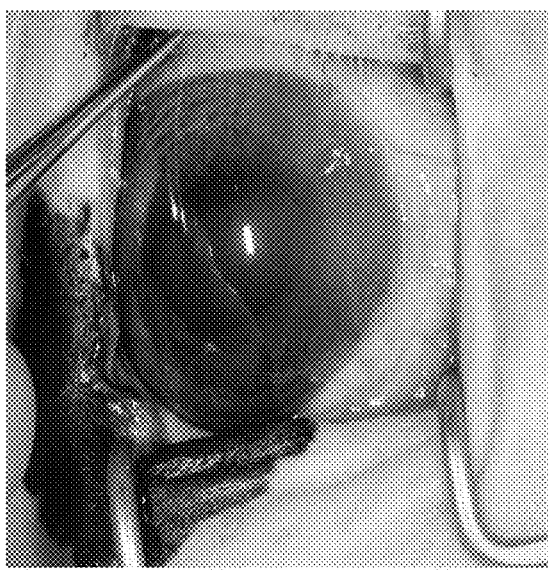
Figure 36D:
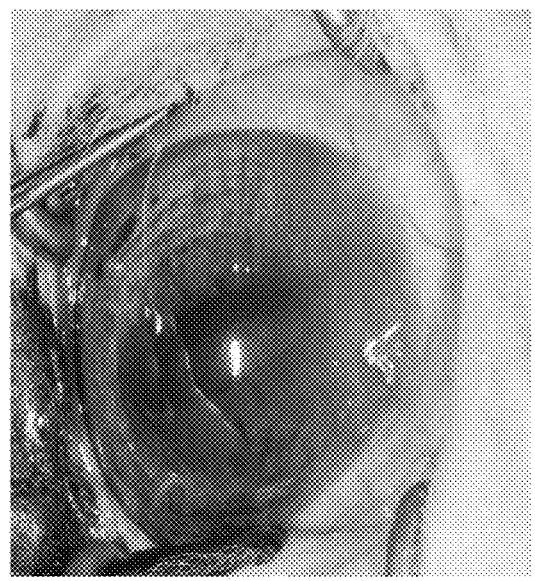

FIGS. 36A and 36D illustrate an exemplary response to certain immunogenic compositions over time (36B-36D) and before treatment (36A) disclosed herein in an animal model having an eye tumor of the cornea according to certain embodiments of the instant invention.

FIGS. 37A and 37D illustrate an exemplary response to topical treatment using certain immunogenic compositions over time (37B-37D) and before treatment (37A) compared to control (top, untreated) disclosed herein in an animal model having an eye tumor of the cornea according to certain embodiments of the instant invention.

DESCRIPTION OF ILLUSTRATIVE EMBODIMENTS

Definitions

Unless defined otherwise, all technical and scientific terms used herein have the same meaning as understood by one of ordinary skill in the art to which the invention belongs.

As used herein, the term "effective amount" can refer to at least an amount effective, at dosages and for periods of time necessary, to achieve the desired result, e.g., enhance innate immune response, an enhanced immune response to an antigen. An effective amount can be provided in one or more administrations.

As used herein, the term "subject" or "individual" or "patient" refers to the target, e.g. human or an animal. A subject disclosed herein can be a vertebrate, such as human or other mammal, a fish, a bird, a reptile, or an amphibian. Alternatively, the subject can be a human, non-human primate, horse, pig, rabbit, dog, sheep, goat, cow, cat, guinea pig, deer, elk, fox, coyote, wolf, or rodent. In one aspect, the subject is a mammal. e.g., a human, or a companion animal (e.g., dog, cat, rodent, rabbit, etc.), a sport animal (e.g., horse, dog, bull, etc.), a farm or food animal (e.g., pig, cow, sheep, goat, etc.), livestock (e.g., donkeys, goats, guinea pigs, sheep, cattle, llamas, etc.), or any other mammalian veterinary animal, or to a bird (e.g., chicken, turkey, duck) or any other avian veterinary species, or other non-mammalian species such as farm-reared fish, or other species such as reptiles or amphibians.

As used herein, the singular form "a", "an", and "the" can include plural references unless indicated otherwise.

As used herein, "about" can include a value or parameter herein refers to the usual error range for the respective value readily known to the skilled person in this technical field. In particular embodiments, reference to about refers to a range within 10% higher or lower than the value or parameter, while in other embodiments, it refers to a range within 5% or 20% higher or lower than the value or parameter. Reference to "about" a value or parameter herein includes (and describes) aspects that are directed to that value or parameter per se. For example, description referring to "about X" includes description of "X."

As used herein, the term "modulating" can mean changing, and can include positively modulating, such as "increasing," "enhancing," "inducing" or "stimulating," as well as negatively modulating such as "decreasing," "inhibiting" or "reducing," typically in a statistically significant or a physiologically significant amount as compared to a control. An "increased," "stimulated" or "enhanced" amount is typically a "statistically significant" amount, and can include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the amount produced by a control of no treatment as described herein or by a control treatment, can include all integers in between. A "decreased," "inhibited" or "reduced" amount is typically a "statistically significant" amount, that can include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%), 80%, 85%, 90%, 95%, or 100% decrease in the amount produced by a control of no treatment as described herein or by a control treatment, including all integers in between.

As used herein, "statistically significant," can mean that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

As used herein, the term "adjuvant" can mean its conventional meaning, for example, the ability to enhance the immune response to a particular antigen or to enhance the immune response in general without an antigen. Such ability is manifested by a significant increase in immune-mediated protection. An enhancement of humoral immunity is typically manifested by a significant increase (usually >10%) in the titer of antibody raised to the antigen. Similarly, enhancement of cellular immunity is typically manifested by a significant increase (usually >10%) in the number of responding CD8+ or CD4+ T cells. The term "about" in relation to a numerical value x means, for example, x+/−10%.

As used herein, the terms "optional" or "optionally" can mean that the subsequently described event or circumstance can or cannot occur, and that the description includes instances where said event or circumstance occurs and instances where it does not.

As used herein, the term "concurrently" as used herein can refer to administration of two or more therapeutic agents, where at least part of the administration overlaps in time. Accordingly, concurrent administration includes a dosing regimen when the administration of one or more agent(s) continues after discontinuing the administration of one or more other agent(s). In certain embodiments, an antigen can be administered concurrently with an immunogenic composition of the present invention. In other embodiments, and immunogenic composition of use in an eye of a subject can be used alone or concurrently or sequentially with another treatment for an eye infection, eye-related tumor and/or chronic ulcer of the eye.

As used herein, the terms "cancer" and "cancerous" can refer to or describe the physiological condition in mammals that is typically characterized by unregulated cell growth. Included in this definition are benign, metastatic and/or malignant cancers as well as dormant tumors or micrometastases. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NEIL; intermediate grade/follicular NHL; intermediate grade diffuse NEIL; high grade immunoblastic NHL; high grade lymphoblastic NEIL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblasts leukemia; and post-transplant lymphoproliferative disorder (PTLD), as well as abnormal vascular proliferation associated with phakomatoses, edema (such as that associated with brain tumors), and Meigs' syndrome.

As used herein, the term "Poly(I:C)" (polyinosinic-polycytidylic acid) is an agent that can be recognized by TLR3. This recognition leads to induction and activation of NF-kB and the production of certain cytokines. Poly(I:C) is composed of a strand of poly(I) annealed to a strand of poly(C). The size of the strands can vary. (e.g. InvivoGen and other manufacturers provide poly(I:C) with at least 2 different sizes: Poly(I:C) (HMW) with a high molecular weight has an average size of about 1.5 kb to about 8.0 kb, and Poly(I:C) (LMW) with a low molecular weight of about 0.2 kb to about 1 kb.

As used herein, the term "CpG oligodeoxynucleotides" (CpG ODN; CpG oligos) are short single-stranded synthetic DNA molecules that contain a cytosine triphosphate deoxynucleotide ("C") followed by a guanine triphosphate deoxynucleotide ("G"). The "p" refers to the phosphodiester link between consecutive nucleotides, although some ODN have a modified phosphorothioate (PS) backbone instead. When these CpG motifs are unmethylated, they act as immunostimulants CpG motifs are considered pathogen-associated molecular patterns (PAMPS) due to their abundance in microbial genomes but their rarity in vertebrate genomes. The CpG PAMP is recognized by the pattern recognition receptor (PRR) Toll-Like Receptor 9 (TLR9), in mammals and avian and fish species.

As used herein, the term "PCT-01" or the term "MiM" is a complex solution that includes cationic liposomes, non-coding plasmid DNA, polyinosinic-polycytidylic acid, and low and/or medium viscosity (and in certain embodiments, molecular weight) adhesion agents of carboxymethylcellulose in a diluent for in vitro and in vivo studies.

As used herein "Non-coding plasmid DNA" can include bacterial replication elements in a circular arrangement. The DNA in plasmids can act as an immunostimulant recognized for example, by the pattern recognition receptor (PRR) Toll-Like Receptor 9 (TLR9), which is expressed in mammals and avian species. In addition, these non-coding plasmids can be engineered to overexpress CpG motifs. In the instant case, the plasmid does not code for any known mammalian genes, and instead codes for several "islands" of CpG motifs (oligonucleotides) engineered into the plasmid to increase its immune stimulatory properties. "CpG oligodeoxynucleotides" (CpG ODN; CpG oligos) are short single-stranded synthetic DNA molecules that contain a cytosine triphosphate deoxynucleotide ("C") followed by a guanine triphosphate deoxynucleotide ("G"). The "p" refers to the phosphodiester link between consecutive nucleotides, although some ODN have a modified phosphorothioate (PS) backbone instead.

DETAILED DESCRIPTION OF THE INVENTION

In the following sections, various exemplary compositions and methods are described in order to detail various embodiments of the invention. It will be obvious to one skilled in the art that practicing the various embodiments does not require the employment of all or even some of the specific details outlined herein, but rather that concentrations, times and other specific details may be modified through routine experimentation. In some cases, well known methods, or components have not been included in the description.

The instant disclosure relates, in part, to improved immunostimulatory compositions, which may be used to induce a non-specific, protective mucosal immune response or other non-specific immune response. In some embodiments, the improved immunostimulatory compositions can be used to treat an eye condition.

In certain embodiments, compositions disclosed herein include improved immunostimulatory compositions. In accordance with these embodiments, immunostimulatory or immunogenic compositions designed to more effectively stimulate local immune responses at mucosal and epithelial surfaces of a subject are disclosed. In accordance with these embodiments, these immunogenic compositions improve properties of a previously developed immunotherapeutic (e.g. cationic-liposome DNA complexes; CLDC). In some embodiments, immunogenic compositions disclosed herein have improved adhesion properties. For example, immunogenic compositions disclosed herein have improved properties, including but not limited to, adhesion to mucosal surfaces, increased potency of immune activation, and duration of immune activation.

In some embodiments, mucosal immune stimulation and adhesion technology disclosed herein provides significant improvement over previously disclosed CLDC technology, which in itself is a potent immune stimulant. In certain embodiments, immunogenic compositions of the instant invention provide for improved induction of mucosal immune responses when compared to previously disclosed cationic liposome-DNA complex (CLDC) formulations.

Some embodiments disclosed herein include immunogenic compositions including at least one of (a) cationic liposomes, at least one (b) toll like receptor (TLR) or mixture thereof, and at least one (c) cellular adhesion agent. Toll-like receptors (TLRs) are conserved pattern recognition receptors expressed on multiple types of cells, including monocytes, dendritic cells, B cells, and macrophages, and play a vital role in modulation of the innate immune system. In certain embodiments, the TLRs include but are not limited to, TLR1, TLR2, TLR3, TLR4, TLR5, TLR6, TLR7, TLR8, TLR9, and TLR10. In other embodiments, TLRs of use in immunogenic compositions disclosed herein include, but are not limited to, TLR3 and TLR9 ligands. In other embodiments, cationic liposomes can include, but are not limited to, a mixture of cationic lipid and non-charged lipids. In accordance with these embodiments, a mixture of cationic lipid and non-charged lipids can include a mixture of DOTAP and cholesterol. In certain embodiments, DOTAP and cholesterol can be about a 1:1 molar ratio or about a 2:1 or about a 1:2 or about 1.5:1 or about 1:1.5 or 1:3 or 3:1 or similar ratio. In some embodiments, the mixture of cationic lipid and non-charged lipids can include at least one of, non-coding plasmid DNA and polyI:C. In other embodiments, the non-coding plasmid DNA can include a polynucleotide represented by the nucleic acid sequence, SEQ ID NO. 1. In yet other embodiments, the mixture of cationic lipid and non-charged lipids can include plasmid DNA and polyI:C in about a 1:1 ratio (by weight) or about a 2:1 or about a 1:2 or about a 1.5:1 or about a 1:1.5 or similar ratio. In certain embodiments, the cellular adhesion agent in an immunogenic composition disclosed herein can be a low- to mid-weight viscosity adhesion agent. In some embodiments, the low- to mid-weight viscosity adhesion agent is carboxymethylcellulose (CMC). In some embodiments, carboxymethylcellulose can be present in an immunogenic composition disclosed herein at about 1% to about 20% (v/v). Certain immunogenic compositions disclosed herein can include complexes of the cationic liposomes and any TLR3 and/or TLR9 ligands known in the art. In other embodiments, complexes disclosed herein can include about 10 µg to about 200 µg TLR ligand per milliliter cationic liposomes. In some embodiments, cationic liposomes can be present at about 1 to about 20 mM concentration in an immunogenic composition disclosed herein. In some alternative embodiments, immunogenic composition can further include an antigen. In some embodiments, the antigen can be a protein antigen. In other embodiments, the antigen can be derived from a virus, bacterium, prion, fungus, a toxin, a tumor-related antigen or other protein or non-protein antigen. In accordance with these embodiments, immunogenic compositions disclosed herein in combination with a targeted antigen can be used to induce an improved innate immune response compared to an antigen without an immunogenic composition of the instant application against the antigen. In certain embodiments, an enhanced innate immune response includes a local or regional response at the site of introducing the immunogenic compositions.

In other embodiments, methods for inducing an innate immune response in a subject are disclosed. In certain embodiments, methods are disclosed for inducing an innate immune response in a subject having an infection or other condition. In accordance with these embodiments, methods can include, but are not limited to, providing to a subject and immunogenic composition disclosed herein. In certain embodiments, the immunogenic composition disclosed herein can include: (a) at least one cationic liposome; (b) one or more TLR ligands (e.g. a mixture of toll like receptor 3 (TLR3) and toll like receptor 9 (TLR9) ligands); and/or (c) one or more cellular adhesion agent. In some embodiments, an infection is caused by a virus, bacterium, fungus, prion or protozoan. In certain embodiments, the condition in a subject includes a respiratory infection and wherein the immunogenic compositions are administered to the lungs of the subject to treat the infection. In accordance with these embodiments, an immunogenic composition disclosed herein can include a polynucleotide represented by SEQ ID NO. 1 and the ligand polyI:C.

In some embodiments, an immunogenic composition disclosed herein can be provided to the subject prior to the risk of or exposure to an infection and/or within 24 hours to a week or more after exposure, during early onset of clinical signs of an infection, or during chronic infection. In accordance with these embodiments, the immunogenic composition is capable of inducing a local, non-specific immune response at a site of administration or at the delivery site after administration (e.g. the lungs). In certain embodiments, immunogenic compositions disclosed herein can be administered to the subject at the site of a wound, an infection or other condition or alternatively, administered to induce a systemic non-specific immune response. In certain subjects, immunogenic compositions disclosed herein can be administered to the reproductive tract, the gastrointestinal tract, the mammary gland, to gills, to air sacs, to eyes, to ears, and to the nose of a subject in need of such a treatment. In yet further aspects, the composition can be administered without the concurrent administration of a vaccine or other known agent for the treatment or reducing onset of a condition.

Further, disclosed herein are embodiments directed to methods for inducing an immune response to an antigen in a subject, including providing to the subject a composition including: (a) at least one cationic liposome; (b) a mixture of toll like receptor 3 (TLR3) and toll like receptor 9 (TLR9) ligands; and (c) at least one cellular adhesion agent; and optionally, an antigen. In other embodiments, an immunogenic composition disclosed herein can be administered to the eye of a subject. In other embodiments, a composition including: (a) at least one cationic liposome; (b) a mixture of toll like receptor 3 (TLR3) and toll like receptor 9 (TLR9) ligands; and (c) at least one cellular adhesion agent can further include a high viscosity and/or high molecular weight (HMW) cellular adhesion agent. In accordance with these embodiments, immunogenic compositions further including a high viscosity and/or high molecular weight adhesion agent can be administered to a subject having a condition of the eye or skin. In certain embodiments, an eye condition can include an infection, a tumor or a chronic injury or wound.

In other embodiments, an eye condition can include but are not limited to, an infection, a tumor, an eye injury, chronic wound or ulcer or similar condition of the eye thereof. In accordance with these embodiments, the eye condition can include a condition that affects the cornea or retina or other component of the eye. Certain embodiments of the invention can include administering an immunogenic composition disclosed herein to the eye of a subject to reduce incidence of blindness or injury to the eye or to treat an infection of the eye. In some embodiments, an infection of the eye can be caused by a virus, bacterium, fungus, prion or other microorganism. In certain embodiments, the infection can be caused by a Herpes virus or other microorganism capable of causing an eye infection. In some embodiments, the eye condition can include an infection of the cornea, adverse condition of the cornea or outer service of the eye.

In other embodiments, an immunogenic composition disclosed herein can be used to treat cancer of the eye. Cancers of the eye can include a localized tumor of the eye or a metastatic cancer of the eye or other type of cancer affecting the eye. In certain embodiments, cancers of the eye can include cancers of any part of the eye or adnexa. In some embodiments, conditions of the eye can include parts of the eye such as parts adjoining the eye. For example, a subsection of the eye and ocular adnexa include ocular muscles and eyelids. In other embodiments, cancer of the eye can include a squamous cell carcinoma (e.g. of the cornea or other component of the eye). In certain embodiments, cancers of the eye can include corneal-related cancers. In other embodiments, cancers of the cornea can include corneal squamous cell carcinoma or other tumor affecting the cornea. In some embodiments, types of tumors of the eye can include, but are not limited to, epithelial tumors of the eyelids, conjunctiva, and cornea which can occur in all species. In some embodiments, intraocular tumors can be treated by immunogenic formulations disclosed herein. For example, iridociliary epithelial tumors and malignant melanomas are contemplated to respond to immunogenic compositions disclosed herein. In other embodiments, other eye tumors can be treated with compositions disclosed herein such as mesenchymal tumors of the eye including, but not limited to, extraocular, optic nerve, nerve sheath, uveal tract tumors, neuroectodermal tumors, melanogenic tumors of the eyelid and/or conjunctiva of the uveal tract and the lacrimal system which line and protect the eye of a subject. In some embodiments, a tumor of the eye can include corneolimbal squamous cell carcinoma (SCC).

In accordance with these embodiments, an immunogenic composition of use to treat an eye-related cancer or tumor can include, but is not limited to, at least one cationic liposome agent, at least one TLR agonist and at least one adhesive agent, wherein the immunogenic composition includes a high viscosity adhesive agent and/or high molecular weight agent. In certain embodiments, the immunogenic composition of use to treat the eye of a subject can include CLDC+CMC of low to mid viscosity and further include a high viscosity adhesive agent. In some embodiments, the high viscosity adhesive agent can include, but is not limited to, high viscosity carboxymethylcellulose (CMC). In certain embodiments, In some embodiments, high viscosity adhesion agent is about 1500 to about 3000 centipoise (cps). In other embodiments, high viscosity CMC is about 1500 to about 3000 centipoise (cps).

In some embodiments, immunogenic compositions disclosed herein can be used to treat an eye infection. In accordance with these embodiments, an infection of the eye can include an infection caused by a pathogenic organism. In some embodiments, a pathogenic organism can include a pathogenic virus, bacterium, prion, fungus or protozoan organism. In certain embodiments, the pathogenic organism can infect any part of the eye or connecting tissues to the eye or eyelid or the like. In other embodiments, an infection of the eye can include an infection of the cornea. In some embodiments, ocular herpes virus infection of the eye is contemplated. In certain embodiments, an infection of the eye can be an acute infection. In other embodiments, an infection of the eye can be a chronic infection. In yet other embodiments, an infection of the eye can be a refractory eye infection; for example, unresponsive to known compositions. In one embodiment, an infection of the eye can be refractory herpes virus keratoconjunctivitis. In certain embodiments, immunogenic compositions of use to treat infectious eye conditions of a subject can reduce the incidence of permanent eye injury and/or blindness in the subject.

In certain embodiments, immunogenic compositions disclosed herein can be used to treat chronic ulcers of the eye. In some embodiments, chronic ulcers of the eye can include a corneal ulcer. A corneal ulcer is an open sore of the cornea. Corneal ulcers contemplated to be treated by immunogenic compositions disclosed herein can include an ulcer due to an infection, physical and/or chemical trauma, corneal drying and exposure, and contact lens over-wear and/or misuse. In certain embodiments, immunogenic compositions disclosed herein can be used to treat corneal ulcers in order to reduce or prevent loss of vision or blindness.

In some embodiments, immunogenic compositions disclosed herein of use to treat a condition of the eye can provide broad spectrum activity of increased duration, reducing frequency of treatment and having reduced side effects such as irritation and inflammation. In certain embodiments, the immunogenic compositions disclosed herein can reduce the incidence of irritation and inflammation as well as treat chronic eye conditions with improved outcomes.

In other embodiments, immunogenic compositions disclosed herein are formulated for prolonged administration reducing frequency of application to a site of infection and/or condition. In some embodiments, immunogenic formulations disclosed herein are designed for topical administration to the eye. In certain embodiments, immunogenic formulations disclosed herein are designed for administering as an eye drop such as a viscous eye drop. In some embodiments, an immunogenic formulation of use for topical administration includes cationic liposomes, a mixture of TLR3 and TLR9 agonists and an adhesive agent. In accordance with these embodiments, an essentially liquid immunogenic formulation disclosed herein (e.g. CLDC plus CMC of low to mid viscosity: MiM) can further include at least one high viscosity adhesion agent. In certain embodiments, a high viscosity or high molecular weight adhesion agent can include, but is not limited to, carboxymethylcellulose (CMC). Other suitable high viscosity and/or high molecular weight adhesion agents include, but are not limited to, dextrans, hyaluronic acid, chondroitin sulfate, petrolatum, mineral oil, and/or lanolin. In other embodiments, a high viscosity and/or high molecular weight adhesion CMC solution is combined with an essentially liquid immunogenic formulation disclosed herein at a predetermined ratio. In accordance with these embodiments, these formulations will have increased viscosity to a gel-like consistency to increase contact time in an affected area (e.g. the eye) in order to increase duration of exposure and improve outcome.

In certain embodiments disclosed herein, combination treatments are contemplated. In accordance with these embodiments, immunogenic compositions disclosed herein (e.g. CLDC plus CMC of low to mid viscosity: MiM) having at least one high molecular weight and/or high viscosity adhesion agent included in the formulation can be used in combination with standard treatments for eye infections, chronic wounds or ulcers and tumors of the eye to obtain improved outcomes. In certain embodiments, immunogenic compositions and formulations disclosed herein can be used before, during or after standard treatment regimens in order to improve outcome. In some embodiments, immunogenic compositions disclosed herein can be used to reduce cost of treatment and reduce the risk of recurrence of an eye condition.

In some embodiments, the immunogenic compositions of the present invention may also be used to induce non-specific immune responses in humans, and pets such as dogs, cats, rabbits; in livestock such as cattle, horses, swine, and birds, such as chickens, turkeys and other birds and fish. In certain embodiments, compositions disclosed herein can be used to treat or reduce the risk of onset of a viral, bacterial, fungus, prion or protozoan infection. In some embodiments, infections of a subject contemplated herein can be a respiratory, ear, eye, sinus, skin, scalp, oral, throat infection, as well as infections of the reproductive or gastrointestinal (GI) tract.

In certain embodiments, compositions disclosed herein can be administered as a liquid by the intranasal and oropharyngeal routes to humans and other mammals (e.g., dogs, cats, cattle, horses, swine, sheep, goats, buffalo poultry) prior to exposure or after exposure to a pathogen. In certain embodiments, animals can be administered an immunogenic composition disclosed herein about 24 h prior to exposure to a pathogen (e.g., shipping animals to feedlots, boarding facilities, veterinary visits or rearing facilities), or within 7 days following exposure to a pathogen and optionally, daily, weekly, bi-weekly or by other regimen while in the facility and for a time after leaving a facility, if desired. In some embodiments, compositions disclosed herein can be used to induce local immune responses in order to reduce the risk of onset of an infection, such as against a virus or bacteria. In some embodiments, the composition may be administered to an animal in a shelter boarding facility to induce an enhanced immune response to a respiratory infection. In some embodiments, a respiratory infection could be one that occurs in a cat or a dog such as an upper respiratory infection due to exposure to a microorganism. It is contemplated herein, that compositions disclosed herein can be of use to a subject in quarantine or other holding facility to reduce the risk of exposing others to a potential infection.

In certain embodiments, immunogenic compositions disclosed herein can be used to treat a subject for, or reduce the risk of onset in a subject of, a viral infection by inducing an enhanced immune response to a respiratory virus such as rhinovirus, influenza virus, adenovirus, or the like. In certain embodiments, immunogenic compositions disclosed herein can be used to treat a subject for or reduce the risk of onset in a subject of, a bacterial infection such as *Staphylococcus, Pneumococcal, Streptococcus* or other bacterial infection.

In a related embodiment, cattle that are shipped to feedlots could be administered an immunogenic composition disclosed herein by intranasal or other rapid administration, before or upon arrival to the facility. It is contemplated that the treatment can be repeated at a predetermined interval such as daily, or weekly or by 14-day intervals as appropriate.

In another embodiment, poultry in intensive husbandry settings (e.g., broiler operations) that are exposed to pathogens or at risk of exposure to pathogens can be treated with immunogenic compositions disclosed herein throughout the building by exposure to an aerosol mist generated by an aerosol generator carried as a backpack by facility personnel.

In another embodiment, fish in for example, fish farms or ponds at risk of infection could be collected into smaller treatment tanks, and the composition can be introduced to the water in the tanks so all the fish would be treated via uptake by the gills or other mucosal surfaces.

In certain embodiments, the immunogenic composition may be used to treat a human. In accordance with these embodiments, the composition can be administered by any method known in the art. In certain embodiments, the immunogenic compositions can be administered to a human intranasally or to the eye by a dropper or ointment. In certain embodiments, the immunogenic composition can be administered as a liquid or spray using a spray bottle, eye dropper, intranasal device or similar device. In certain embodiments, humans at risk of contracting a viral infection or being exposed to a bacterial infection (e.g., during airline travel, holiday gatherings, classrooms) can administer immunogenic compositions disclosed herein prior to the encounter and then a day to 7 days to within 14 days afterward potential exposure.

In some embodiments, immunogenic compositions of the present invention generate rapid, broad immune response against pathogenic agents following application to mucosal surfaces. In other embodiments, data provided herein demonstrates superior induction of mucosal immune responses with the compositions of the present invention as compared to previous cationic liposome-DNA complex (CLDC) formulations.

According to certain alternative embodiments, the instant disclosure also relates, in part, to improved immunostimulatory compositions. In accordance with these embodiments, the improved or enhanced immunostimulatory compositions can be used as adjuvants, alone or in combination with antigens in, for example, vaccines. In certain embodiments, immunogenic compositions disclosed herein have include an improved liposomal vaccine adjuvant with greater lymph node trafficking ability for greater vaccine adjuvant activity. In certain embodiments, by combining an adhesive agent (e.g., carboxymethylcellulose) with a cationic liposome-TLR agonist complex, migration of vaccine antigens to draining lymph nodes is enhanced, resulting in enhanced immune responses, as well as, enhance immune responses to antigens (e.g. protein antigens). In certain embodiments, immunogenic compositions disclosed herein provide improved immunostimulatory properties of a previously developed immunotherapeutic (e.g. cationic-liposome DNA complexes; CLDC); for example, with respect to vaccine adjuvant properties and immunological responses to administration of a vaccine.

In certain embodiments, immunogenic compositions disclosed herein can include an immunogenic composition for application to an eye of a subject. In accordance with these embodiments, the immunostimulatory compositions can include, but are not limited to, the following components: cationic liposomes including at least one cationically-charged lipid in a predetermined ratio with cholesterol; one or more TLR ligand, such as TLR3 and/or TLR9 ligands or agonists (e.g. TLR ligands); for example, including non-coding plasmid DNA (TLR9 agonist) and/or polyinosinic-polycytidylic acid (TLR3 agonist); at least one cellular adhesion agent (e.g., carboxymethylcellulose, or chitosan, polyglycol, or hyaluronan) and further comprising a high molecular weight/high viscosity cell adhesion agent. In some embodiments, the high molecular weight/high viscosity adhesion agent can be a carboxymethylcellulose agent, a high molecular weight/high viscosity surfactant agent (e.g. a poloxamer such as poloxamer 407 or other) In accordance with these embodiments, a subject responsive to these immunogenic agents can be a subject suffering from an eye condition including, but not limited to, an eye tumor, an eye infection, an acute eye condition and/or chronic eye condition. In certain embodiments, the eye condition can include an eye condition that affects any component of the eye. In other embodiments, the eye condition can include a condition of the cornea. In some embodiments, the immunogenic compositions comprises MiM and a high viscosity carboxymethylcellulose agent (HV CMC). In some embodiments, MiM can be mixed 30/70, 70/30, 40/60; 60/40, 50/50 v/v or other pre-determined ratio with a solution of a high viscosity and/or high molecular weight CMC or other high molecular weight/high viscosity adhesive agent. In some embodiments, the high viscosity and/or high molecular weight CMC solution can be a 0.5% to a 10.0% solution. In other embodiments, the high viscosity and/or high molecular weight CMC solution can be a 0.5% to a 5.0% solution or a 0.5% to a 3% solution. In other embodiments, the final high viscosity CMC solution can be a 0.5% to a 2.5% solution or a 0.5% to a 1.5% solution or a final of a 1% solution of high viscosity having high molecular weight CMC. In certain embodiments, the MiM essentially liquid composition becomes a viscous gel-like consistency for administration to the eye of a subject (e.g. similar viscosity to implantation of a urinary or nasopharyngeal catheter)

In certain embodiments, compositions disclosed herein can be used to treat corneal conditions. Corneal diseases are a major causes of blindness and irreversible eye injury. There are currently no approved immunotherapies for corneal conditions (e.g. viral, bacterial, fungal, neoplastic). Therefore, there is an unmet need for eye conditions including, but not limited to, ocular herpesvirus, non-healing corneal ulcers and/or corneal squamous cell carcinoma. Current treatments are often off-label agents that have major drawbacks, narrow spectrum of activity, short duration, require frequent administration (every 3-4 hours) and often have intolerable side effects such as irritation and inflammation. In some embodiments, immunogenic compositions disclosed herein can be specifically formulated for topical administration to the eye leading to broad-spectrum ocular immunotherapy. In accordance with these embodiments, broad-spectrum ocular immunotherapy can include but is not limited to anti-viral, anti-neoplastic, anti-fungal and/or anti-bacterial activity. In other embodiments, compositions disclosed herein (e.g. Ocummune) can provide sustained immune activation and have convenient dosing regimens; for example, once a day, every other day, weekly or other regimen. In other embodiments, compositions disclosed herein (e.g. Ocummune) can provide treatments against multiple pathogens and other eye conditions simultaneously.

In some embodiments, one targeted condition of the instant inventions includes, but is not limited to, herpesvirus keratitis. Herpesvirus keratitis is the most common cause of infectious blindness in humans. There are no treatments available to rapidly suppress or prevent recurrence of this infection. Standard treatments of care include anti-viral eye drops which require prolonged treatment, frequent dosing, and relapse is very common. Another treatment includes oral herpesvirus drugs which can cause side-effects and are expensive. In some embodiments, Ocummune or similar immunogenic composition disclosed herein can be used to treat herpesvirus keratitis in a subject with improved outcomes at reduced cost and reduce dosing frequencies.

In some embodiments, another targeted condition of the instant inventions includes, but is not limited to, non-healing corneal ulcers. There is no consistently effective therapy on the market and multiple off-label and unapproved products are being used with mixed outcomes. There is a large unmet medical need because these conditions can lead to significant risk of loss of vision. In some embodiments, Ocummune or similar immunogenic composition disclosed herein can be used to treat non-healing corneal ulcers in a subject with improved and predictable outcomes.

In yet other embodiments, other targeted conditions can include treating corneolimbal squamous cell carcinoma. Corneolimbal squamous cell carcinoma (SCC) is the most common surface eye tumor, increasing incidence worldwide. There is currently no approved treatments. Multiple approaches have been attempted but none have been proven to be consistently effective. The recurrence rate is about 20%. These conditions frequently cause of eye loss in those suffering from this cancer. Current agents of use to treat these conditions are off-label drugs and many of them have significant adverse effects. In some embodiments, Ocummune or similar immunogenic composition disclosed herein can be used to treat non-healing corneal ulcers in a subject with improved and predictable outcomes.

In some embodiments, the immunogenic compositions comprises MiM and a high viscosity adhesion agent (e.g. HV CMC). In accordance with these embodiments, the immunogenic agent containing a high viscosity adhesion agent can be a viscous eye drop. In certain embodiments, these eye drops can be administered once daily to eyes of a subject having an eye condition. In some embodiments, these novel composition activate host innate immune responses by TLRs in the cornea and surrounding adnexal tissues having a local distribution and not systemic. Clearance can be rapid due in part to rapid degradation of nucleic acids. In other embodiments, eye treatments can be closely monitored by tear cytokines, corneal cytology, and/or scheduled and frequent eye exams General Methods Embodiments of the present invention can employ, unless otherwise indicated, conventional techniques of cell culturing, molecular biology (including recombinant techniques), microbiology, cell biology, biochemistry and immunology, which are within the skill of the art. Such techniques are explained fully in the literature, such as, Molecular Cloning: A Laboratory Manual, third edition (Sambrook et al., 2001) Cold Spring Harbor Press; Oligonucleotide Synthesis (P. Herdewijn, ed., 2004); Animal Cell Culture (R. I. Freshney), ed., 1987); Methods in Enzymology (Academic Press, Inc.); Handbook of Experimental Immunology (D. M. Weir & C. C. Blackwell, eds.); Gene Transfer Vectors for Mammalian Cells (J. M. Miller & M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Manual of Clinical Laboratory Immunology (B. Detrick, N. R. Rose, and J. D. Folds eds., 2006); Immunochemical Protocols (J. Pound, ed., 2003); Lab Manual in Biochemistry: Immunology and Biotechnology (A. Nigam and A. Ayyagari, eds. 2007); Immunology Methods Manual: The Comprehensive Sourcebook of Techniques (Ivan Lefkovits, ed., 1996); Using Antibodies: A Laboratory Manual (E. Harlow and D. Lane, eds., 1988); and others.

Immunostimulatory Compositions

Embodiments disclosed herein provide for novel immunostimulatory compositions. In certain embodiments, these immunostimulatory compositions are used to induce a non-specific immune response in a subject.

In other embodiments, the immunostimulatory compositions can include, but are not limited to, the following components: cationic liposomes including at least one cationically-charged lipid in a predetermined ratio with cholesterol; one or more TLR ligand, such as TLR3 and/or TLR9 ligands or agonists (TLR ligands), including non-coding plasmid DNA (TLR9 agonist) and polyinosinic-polycytidylic acid (TLR3 agonist); and at least one cellular adhesion agent (e.g., carboxymethyl cellulose, or chitosan, polyglycol, or hyaluronan). In other embodiments, the immunostimulatory compositions can further include a high molecular weight/high viscosity adhesion molecule such as HMW/high viscosity CMC or other HMW/high viscosity adhesion agents (e.g. chitosan, polyglycol, poloxamer agent or hyaluronan)

In some embodiments, the immunostimulatory composition includes both a CLDC and a cellular adhesion agent of low and/or medium molecular weight. In certain embodiments, the immunostimulatory composition includes both a CLDPC and a cellular adhesion agent of low or medium molecular weight.

TLR3 and TLR9 Ligands (TLR Ligands)

In one embodiment, the TLR ligand can be a cationic liposome combined with a TLR9 agonist (e.g. either plasmid DNA (e.g., non-coding plasmid DNA), or CpG oligos)), referenced herein in certain embodiments as a CLDC adjuvant. In one embodiment, the TLR ligand is a cationic liposome DNA-pIC complex (CLDPC). According to certain exemplary embodiments, the TLR9 agonist can be a non-coding plasmid represented by SEQ ID NO. 1. In accordance with these embodiments, the plasmid (See for example, FIG. 34) includes a plurality of CpG motifs, but does not contain antibiotic resistance genes (e.g. as mandated for regulatory purposes by the USDA and FDA).

In certain embodiments, the immunogenic compositions of the present invention can elicit both a cell-mediated immune response and a humoral immune response when administered to a subject. In some embodiments, these immune responses can induce prolonged exposure to antibodies as well as an enhanced T cell-mediated immune response. In some embodiments, the enhanced T-cell response can include and enhanced CD4 and/or CD8 T-cell response. In certain embodiments, the disclosed CLDC adjuvant primarily elicits a Th1 response. In some embodiments, the TLR ligand is prepared with a CLDC adjuvant and/or CLDPC adjuvant capable of eliciting an enhanced and effective cell-mediated immunity. In certain embodiments, the immunogenic compositions can include other adjuvants capable of eliciting and enhanced Th1 immune response.

In some embodiments, the TLR ligand includes, but is not limited to, cationic liposomes complexed to non-coding plasmid DNA (CLDC), as this adjuvant is particularly effective in eliciting T cell (e.g. such as CD8 and CD4) responses. In other embodiment, the CLDC adjuvant can be prepared using cationic liposomes combined with CpG oligos. In some embodiments, the CLPDC can include cationic liposomes complexed to polyI:C and plasmid DNA. In other embodiments, the complex includes cationic liposomes (e.g., DOTAP) in a 1:1 to 1:2 molar ratio with cholesterol, e.g., formulated as small unilamellar vesicles in dextrose or sucrose solution, and polyI:C and/or plasmid DNA (e.g., non-coding DNA). When both are present, in certain embodiments, the polyI:C and plasmid DNA may be present in a ratio of 1:2 to 2:1, e.g., 1:1 (by weight). In certain embodiments, the complex contains about 10 µg to about 500 µg, about 50 to about 200 µg, or about 100 µg total of polyI:C and/or DNA per 1 ml liposomes or other volume of liposomes. In some embodiments, the liposome concentration can be from about 1 to about 20 mM or about 5 to about 15 mM or about 10 mM. In other embodiments, the cationic liposomes can include a cationic lipid (e.g., DOTAP or DOTIM) mixed in a 1:1 or 2:1 or 1:2 molar ratio of cholesterol and rehydrated to produce liposomes in the range of about 100 to about 350, to about 150 to about 300 to about 250 nm diameter. In certain embodiments, any of the CLDC and CLPDC adjuvants can include a cellular adhesive agent. In some embodiments, the cellular adhesion agent is a low to medium molecular weight cell adhesion agent. In other embodiments, the cellular adhesion agent is a high molecular weight/high viscosity adhesion agent. In certain embodiments, the cell adhesion agent can be carboxymethylcellulose (CMC). In certain embodiments, the CLDC adjuvant can include cationic liposomes (e.g., DOTAP and cholesterol (10 mM), 1:2 to 2:1 ratio or about 1:1 ratio), and non-coding plasmid DNA (e.g. about 10 µg/ml to about 500 µg/ml or about 10 µg/ml to about 200 µg/ml, or about 50 µg/ml). In some embodiments, the CLDC adjuvant can include cationic liposomes (e.g., DOTAP and cholesterol, 1:1 ratio), and non-coding plasmid DNA (50 µg/ml). In other embodiments, the immunogenic compositions can include both a CLDC adjuvant and carboxymethylcellulose (CMC) at about 1% to about 20%, about 2% to about 15%, about 2.5% to about 10%, about 5% to about 10% or about 10% or about 5% v/v. In certain embodiments, the CLPDC adjuvant can include cationic liposomes (e.g., DOTAP and cholesterol, 1:2 to 2:1 ratio or about 1:1 ratio), non-coding plasmid DNA (about 10 µg/ml to about 500 µg/ml or about 10 µg/ml to about 200 µg/ml, or about 50 µg/ml), and synthetic pIC (about 10-500 µg/ml or about 10-200 µg/ml or about 50 µg/ml). In some embodiments, the LPDC composition includes cationic liposomes (e.g., DOTAP and cholesterol, 1:1 ratio), non-coding plasmid DNA (50 µg/ml), and synthetic pIC (50 µg/ml). In certain embodiments, the compositions includes both a CLPDC composition and carboxymethylcellulose (CMC) at about 1% to about 20%, about 2% to about 15%, about 2.5% to about 10%, about 5% or about 10% or about 5% v/v in the final composition.

Cellular Adhesion Agent

In certain embodiments, the immunogenic composition or adjuvanted composition includes at least one cellular adhesion agent. In some embodiments, the at least one cellular adhesion agent enhances uptake of the composition by the mucosa or other tissue and cells exposed to the compositions. In certain embodiments, compositions can be administered by any method known in the art. In other embodiments, compositions disclosed herein can be administered either orally, intranasally, topically, by dropper (e.g. eye, ear, nose) or nasally, where the composition id capable of adhering to and/or anchors to a subject's mucous membrane or cellular surface or intradermal layer for a period of time sufficient for the composition to exert its immunostimulatory effects.

In particular embodiments, the cellular adhesion agent can be carboxymethylcellulose, e.g. a low to mid-weight viscosity formulation and/or a high molecular weight cellular adhesion agent. Carboxymethylcellulose (CMC) or cellulose gum is a cellulose derivative with carboxymethyl groups (—CH2-COOH) bound to some of the hydroxyl groups of the glucopyranose monomers that make up the cellulose backbone. In certain embodiments, the CMC is a sodium salt derivative, sodium carboxymethyl cellulose. In some embodiments, CMC is present in the composition at about 0.1% to about 20%, about 1% to about 20% (v/v), 2% to 15%, 2.4% to 10%, 2.5% to about or about 5% (v/v). In some embodiments, low viscosity carboxymethylcellulose (CMC) agents can have a viscosity of a 4% solution in a diluent (e.g. water or PBS or other) at about room temperature (e.g. 25° C.) and can be 50-200 centipoise (cps). Viscosity is both concentration and temperature dependent. As the temperature increases, the viscosity decreases. As the concentration of these agents increases, the viscosity increases. In various embodiments, low, medium and high viscosity carboxymethylcellulose (CMC) are used in the compositions of the present invention. Low viscosity CMC is usually used in "thin" aqueous solutions. Medium viscosity CMC is usually used to make solutions that look like a syrup. In other embodiments, low viscosity CMC can have a molecular weight of about 50 to about 150; or about 50 to about 100 or about 90 kDa; a degree of polymerization of 400; a degree of substitution of 0.65-0.90 (6.5-9.0 carboxymethyl groups per 10 anhydroglucose units); and a sodium content of about 8% by weight. In certain embodiments, medium viscosity carboxymethylcellulose (CMC) can have a viscosity of a 2% solution in a diluent (e.g. water or PBS or other) at about room temperature (e.g. 25° C.) and can be 400-800 centipoise (cps). In certain embodiments, medium viscosity CMC can have a molecular weight of about 150 to about 350; about 200 to about 300 or about 250 kDa; a degree of polymerization of about 1100; and a degree of substitution of about 0.7 (approximately 7 carboxymethyl groups per 10 anhydroglucose units).

In other embodiments, high viscosity cell adhesion agents are contemplated. In some embodiments, a high viscosity cell adhesion agent can include carboxymethylcellulose (CMC) having viscosity in about 1% solution in a diluent (e.g. water or PBS or other) at about room temperature (e.g. 25° C.) and can be from about 1500 to about 3000 centipoise (cps). In some embodiments, high viscosity CMC as used herein can be used to make a mixture that resembles a cream or lotion. In other embodiments, high viscosity CMC can have increased viscosity compared to low or medium viscosity CMC while still being capable of delivery to a subject by a dropper bottle but has viscous gel-like properties. In certain embodiments, low viscosity CMC can be used in "thin" aqueous solutions. In some embodiments, high viscosity CMC has a molecular weight of about 400 to about 1000, about 500 to about 900, about 600 to about 800, about 650 to about 750; or about 700 kDa; a degree of polymerization of about 3200; and a degree of substitution of about 0.65-0.85 (6.5-8.5 carboxymethyl groups per 10 anhydroglucose units). As used herein, a "poise" is a unit of viscosity based on a flow rate using the standard of water at 20° C. having a poise value of exactly 1 centipoise or one hundredth of a poise. One poise can be referred to as "P" in the following equation: $1P=(0.10 \text{ kg/meter})/\text{sec}=(1 \text{ g/cm})/\text{sec}$.

In certain alternative embodiments, the cellular adhesion agent can be chitosan. In further alternative embodiments, the cellular adhesion agent can be hyaluronan. Hyaluronan, also known as hyaluronic acid, is a is an anionic, nonsulfated mucoid polysaccharide of biological origin. According to still further embodiments, the cellular adhesion agent is a polymer. As will be appreciated by those skilled in the art, suitable polymers in these embodiments are those with hydrophilic functional groups or those that bind to specific receptors on cell or mucus surface (e.g., lectins, thiolated polymers) or lipoid S100.

In certain embodiments, the cellular adhesion agent can be a propylene glycol. As used herein, "propylene glycol" or "PEG" is a polyether compound of general formula H—(O—CH2-CH2)n-OH. PEGs are also known as polyethylene oxides (PEOs) or polyoxyethylenes (POEs), depending on their molecular weight PEO, PEE, or POG, as used herein, refers to an oligomer or polymer of ethylene oxide. The three names are chemically synonymous, but PEG has tended to refer to oligomers and polymers with a molecular mass below 20,000 g/mol, PEO to polymers with a molecular mass above 20,000 g/mol, and POE to a polymer of any molecular mass. PEG and PEO are liquids or low-melting solids, depending on their molecular weights. Throughout this disclosure, the 3 names are used indistinguishably. PEGs are prepared by polymerization of ethylene oxide and are commercially available over a wide range of molecular weights from 300 g/mol to 10,000,000 g/mol. In certain embodiments, the PEG is water-soluble (amphiphilic or hydrophilic), non-toxic, and pharmaceutically inert. Suitable polymeric moieties include polyethylene glycols (PEG), homo- or co-polymers of PEG, a monomethyl-substituted polymer of PEG (mPEG), or polyoxyethylene glycerol (POG). See, for example, Int. J. Hematology 68:1 (1998); Bioconjugate Chem. 6:150 (1995); and Crit. Rev. Therap. Drug Carrier Sys. 9:249 (1992). Suitable PEG polymers will vary substantially by weights ranging from about 200 to about 60,000. In certain embodiments, PEGs having molecular weights from 200 to 2,000 or from 200 to 500 are used. Lower-molecular-weight PEGs are also available as pure oligomers, referred to as monodisperse, uniform, or discrete. PEGs are also available with different geometries: branched PEGs have three to ten PEG chains emanating from a central core group; star PEGs have 10 to 100 PEG chains emanating from a central core group; and comb PEGs have multiple PEG chains normally grafted onto a polymer backbone. PEGs can also be linear.

In other embodiments, the cellular adhesion molecule can be a surfactant. In some embodiments, the cellular adhesion molecule can be a high molecular weight/high viscosity surfactant (e.g. a poloxamer).

In one embodiment, immunogenic compositions disclosed herein are prepared by combining complexes of cationic liposomes with DNA and/or pIC. In other embodiments, the adhesive agent (also referred to as the cellular adhesive agent) can be added to the combined complexes. In certain embodiments, an antigen can be added to the combined complexes containing the cellular adhesive agent. In yet other embodiments, a high molecular weight adhesive agent is added to the combined complexes containing the cellular adhesive agent to make a HMW/high viscosity adhesive agent immunogenic composition and used in a subject to induce an enhanced immune response, alone or in combination with other standards of care. In some embodiments, the HMW/high viscosity adhesive agent immunogenic composition can be administered to a subject having an eye disorder.

In other embodiments, the composition can be administered by a variety of mucosal routes of delivery, including intranasally, orally, inter-rectally, intra-vaginally, or by the intra-mammary or intra-uterine route, or by aerosol mist exposure, or by dilution in water (fish). Alternative routes of delivery include parenterally, e.g., intravenously, subcutaneously, intraperitoneally, or intramuscularly.

Immune cells at mucosal surfaces include dendritic cells (DC), monocytes and macrophages, neutrophils, and B cells, and in some species such as cattle and other ruminants, a specialized subset of T cells known as gamma-delta T cells (γδ T cells). In addition, epithelial cells lining mucosal surfaces can also respond to immune stimuli. The coordinated activation of immune cells and epithelial cells can induce immune responses to suppress infection by either prevent viral or bacterial infection, or significantly reduce the severity of infection and limit pathogen replication. In addition, strong activation of local immune responses at mucosal surfaces can also reduce the severity of infection even after the infection has already been initiated (e.g., when the immune stimulus is administered in an early therapeutic setting as opposed to for prophylaxis).

When immune stimuli reach mucosal surfaces, they are sampled by local DC and macrophages, which then become activated and produce cytokines and chemokines, including inflammatory cytokines (e.g., TNF, IL-1, IL-6) as well as antiviral and antibacterial cytokines (e.g., IFN-γ, IFN-α, INF-β) and other cytokines such as IL-12 and IL-22. The epithelial cells also respond to immune stimuli and produce chemokines (and cytokines) that serve to recruit immune cells to the sites of inflammation. Key chemokines produced by epithelial cells include MCP-1, which recruits monocytes, and IL-8, which recruits neutrophils. Monocytes and neutrophils both play key role in early immune defenses against viral and bacterial pathogens of the respiratory tract and other mucosal surfaces. Some immune stimuli can also directly activate a specialized type of T cell (γδ T cell) that is only found at mucosal surfaces, especially in cattle and other ruminants, and also another cell type known as NK cells, which are present in all mammalian species.

The early cytokine and chemokine responses serve to amplify local immune responses and recruit other inflammatory cells, including monocytes, neutrophils, NK cells and later conventional T cells. These other inflammatory cells produce antiviral and antibacterial cytokines, and also secrete factors such as reactive oxygen and reactive nitrogen species that can directly kill certain bacteria and viruses. In addition, these immune cells and epithelial cells can also produce antimicrobial peptides that kill bacteria and enhance the activity of antibiotics.

To activate mucosal immune defenses effectively, an immune stimulant needs several important properties. These include the ability to first adhere well to epithelial surfaces, and in some cases penetrate into and around epithelial cells. Cationic liposomes are very effective at introducing nucleic acid molecules such as polyIC and plasmid DNA or CpG oligonucleotides into cells such as epithelial cells and immune cells.

An effective mucosal immune stimulant also needs to be very potent, given the large surface areas that must be contacted by relatively small volumes of the immune stimulant. In addition, the ability to induce broad spectrum immune responses, by activating both antibacterial and antiviral immune pathways, is important. Thus, activation of the TLR3 pathway induces anti-viral immune responses, while activation of the TLR9 pathway induces antibacterial immune responses. By activating both pathways simultaneously, the breadth and potency of the immune response that is induced is greatly increased.

In immunogenic compositions disclosed herein an effective mucosal immune stimulant should be capable of interacting with epithelial cells and immune cells for prolonged periods of time in order to induce a sustained immune response. In accordance with embodiments disclosed herein, addition of a mucosal adhesion agent serves to disperse the immune stimulant over large mucus membrane surfaces, and also prolongs the contact time. For example, addition of a mucosal adhesion agent such as carboxymethylcellulose to an immune stimulant such as a liposome-TLR agonist complex can induce local immune stimulation at mucosal surfaces for prolonged periods, for example more than 7 to more than 14 days or longer. Prolonged exposure to these compositions can reduce the risk of onset of an infection, treat an infection or treat a tumor or chronic ulcer in the region of application, for example. In addition, this period of time is sufficient for reducing the chance of infection from most pathogens; for example, exposures in respiratory disease settings. In other embodiments, with respect to treating a subject with the immunogenic compositions disclosed herein of use as a mucosal immune stimulants, this prolonged duration of immune activation provides a more effective long-term therapeutic response. In certain embodiments, prolonged exposure to the immunogenic compositions disclosed herein can lead to generation of T cell responses and antibody responses (as described further below).

Vaccine and Adjuvants

In other embodiments, an antigen (e.g. protein antigen against a pathogen or other agent) in combination with immunostimulatory compositions disclosed herein can be used as a vaccine. In accordance with these embodiments, all components of the adjuvant or vaccine are present in the same pharmaceutical composition, which may be a liquid composition and which may further comprise one or more excipients, diluents or carriers. The pharmaceutical compositions may be sterile. In certain embodiments, the liposome-TLR ligand complexes include a protein antigen.

In accordance with these embodiments, immunogenic compositions (e.g. MiM) in combination with a high viscosity and/or high molecular weight adhesion agent can form a viscous composition and be used as a pharmaceutical agent for delivering to the eye of a subject. In accordance with these embodiments, immunogenic compositions disclosed herein can further include one or more excipients, diluents or carriers. In other embodiments, immunogenic compositions disclosed herein can include higher or lower concentrations of the high viscosity and/or high molecular weight adhesion agent depending on the condition and how long exposure is desired in the targeted area (e.g. eye) and the condition being treated (e.g. chronic infection, tumor or injury). In certain embodiments, the consistency of the immunogenic composition having high viscosity and/or high molecular weight adhesion agents can be where the composition is capable of being delivered by a drop bottle but the composition remains in the delivery location for a prolonged period (e.g. on the cornea).

In certain embodiments, immunogenic compositions disclosed herein include an immunostimulant of cationic liposomes complexed to TLR agonists (plasmid DNA and/or polyinosinic polycytidylic acid; pIC), and low- or medium-molecular weight carboxymethylcellulose (CMC) as an adhesive agent to increase uptake and trafficking to lymph nodes. In some embodiments, immunogenic compositions disclosed herein include: 1) cationic liposomes (e.g., DOTAP and cholesterol, 1:1 molar ratio); 2) non-coding plasmid DNA (e.g., 50 ug/ml); 3) synthetic pIC (e.g., 50 ug/ml); 4) carboxymethylcellulose (CMC) (e.g., 5% v/v with final vaccine). In other embodiments, immunogenic compositions disclosed herein can include an immunostimulant of cationic liposomes complexed to TLR agonists (plasmid DNA and/or polyinosinic polycytidylic acid; pIC), and low- and/or medium-molecular weight carboxymethylcellulose (CMC) as an adhesive agent; and high molecular weight/high viscosity carboxymethylcellulose. In some embodiments, immunogenic compositions disclosed herein include: 1) cationic liposomes (e.g., DOTAP and cholesterol, 1:1 molar ratio); 2) non-coding plasmid DNA (e.g., 50 ug/ml); 3) synthetic pIC (e.g., 50 ug/ml); 4) carboxymethylcellulose (CMC) and 5) high viscosity/high molecular weight carboxymethylcellulose.

In one embodiment, to prepare the adjuvant, complexes of cationic liposomes with DNA and pIC are prepared, then the antigen is added. The final step is the addition of the CMC adhesive agent. In particular embodiments, the vaccine is then administered by the s.c. or i.m. route. In various embodiments, this vaccine technology is applicable to the treatment and prevention of both infectious disease and cancer vaccine applications.

In certain methods disclosed herein, to generate immunity with vaccine adjuvants and antigens, T cells can be stimulated. While T cells play little direct role in mucosal immune responses, they are important for longer term protection against viral, fungal, prion, protozoan and bacterial infections, as in the case of conventional prophylactic vaccines. Further, T cells also play an important role in cancer immunity.

In some embodiments, CD4+ and CD8+ T cells initiate and/or enhance cell mediated immunity and humoral immunity. CD8+ T cells interact with antigens displayed on MHC Class I molecules. CD4 T cells recognize antigenic peptides bound to MHC class II molecules. Upon interaction with a MHC class II molecule, the CD4 cells secrete factors such as cytokines, which activate B cells, cytotoxic T cells, macrophages, and other cells that participate in an immune response.

In some embodiments, a vaccine against an infection of the eye can be used in combination with immunogenic compositions including a high viscosity/high molecular weight adhesion agent. In some embodiments, a vaccine against a viral infection is contemplated. In certain embodiments, a vaccine against herpes virus infection of the eye is contemplated.

Other Adjuvants

In some embodiments, other adjuvants may be present in the immunostimulatory compositions and vaccines of the present invention, or delivered in combinations, including those that stimulate either or both a TH1 and/or TH2 response. TH1 adjuvants suitable for use in the invention may include, for example, saponin formulations, virosomes and virus like particles, non-toxic derivatives of enterobacterial lipopolysaccharide (LPS), immunostimulatory oligonucleotides. Immunostimulatory oligonucleotides, such as oligonucleotides containing a CpG motif, are typical TH1 adjuvants. TH2 adjuvants suitable for use in the invention include, for example, mineral containing compositions, oil-emulsions, and ADP-ribosylating toxins and detoxified derivatives thereof. Mineral containing compositions, such as aluminum salts are typical TH2 adjuvants for use in the invention.

Other adjuvants that can be included in the immunogenic compositions disclosed herein can include any adjuvant known or used in the art, including but not limited to: CLDC adjuvants, mineral salts, such as aluminum salts and calcium salts, including hydroxides (e.g., oxyhydroxides), phosphates (e.g., hydroxyphosphates, orthophosphates) and sulfates, etc.; oil-in water emulsions, such as squalene-water emulsions, including MF59 (5% Squalene, 0.5% Tween 80, and 0.5% Span 85, formulated into submicron particles using a microfluidizer); complete Freund's adjuvant (CFA) and incomplete Freund's adjuvant (IFA); saponin formulations, such as QS21 and ISCOMs; virosomes and virus-like particles (VLPs); bacterial or microbial derivatives, such as non-toxic derivatives of enterobacterial lipopolysaccharide (LPS), Lipid A derivatives; immunostimulatory oligonucleotides, such as IC-31 (deoxynucleotide comprising 26-mer sequence 5'-(IC)13-3' and polycationic polymer polypeptide comprising 11-mer amino acid sequence KLKLLLLLKLK, SEQ ID NO: 2) and ADP-ribosylating toxins and detoxified derivatives thereof; human immunomodulators, including cytokines, such as interleukins (e.g., IL-1, IL-2, IL-4, IL-5, IL-6, IL-7, IL-12, interferons (e.g., interferon-gamma), macrophage colony stimulating factor, and tumor necrosis factor; bioadhesives and mucoadhesives, such as chitosan and derivatives thereof, esterified hyaluronic acid microspheres or mucoadhesives, such as crosslinked derivatives of poly (acrylic acid), polyvinyl alcohol, polyvinyl pyrollidone, polysaccharides and carboxymethylcellulose; microparticles (e.g., a particle of about 100 nm to about 150 um in diameter) formed from materials that are biodegradable and non-toxic (e.g., a poly(alpha-hydroxy acid), a polyhydroxybutyric acid, a polyorthoester, a polyanhydride, a polycaprolactone, etc.); liposomes; polyoxyethylene ethers and polyoxyethylene esters; PCPP formulations; muramyl polypeptides, including N-acetyl-muramyl-L-threonyl-D-isoglutamine (thr-MDP), N-acetyl-normuramyl-l-alanyl-d-isoglutamine (nor-MDP), and N-acetylmuramyl-1 lalanyl-d-isoglutaminyl-1-alanine-2-(1'-2'-dipalmitoyl-s-n-glycero-3-hydroxyphosphoryloxy)-ethylamine MTP-PE); and imidazoquinolone compounds, including Imiquamod and its homologues (e.g. "Resiquimod 3M"). Illustrative adjuvants suitable for use include, but are not limited to, cationic lipid DNA complexes (CLDC), CpG-oligonucleotides, poly I:C, LPS, alphagalactosylceramide, and the like.

Antigens

In certain embodiments, the immunogenic compositions of the present invention are combined with an antigen, or administered sequentially to a subject to induce an enhanced immune response. In some embodiments, the compositions disclosed herein can include a protein antigen or antigen derived from a pathogenic agent. In some embodiments, the antigen is a viral, fungal, protozoan, prion or bacterial antigen. In other embodiments, compositions (e.g., vaccines) and kits of the invention include an antigen, and certain methods of the invention comprise administering an antigen. In certain embodiments, the antigen present in the vaccine compositions provided by the invention can be any material or substance that can induce an immune response (e.g., cellular and/or humoral immune response) by the immune system of a human or animal. For example, the antigen can be a polypeptide of interest derived from an infectious agent, e.g., a bacterium, a virus, a fungus, a protozoan, a parasite, or a prion. The antigen can be a whole microbe or a mixture thereof. The compositions can include a live whole infectious agent. In certain embodiments, the compositions can include a killed or inactivated (attenuated) infectious agent.

In certain embodiments, the antigen includes, e.g., a polypeptide, nucleic acid, polysaccharide, a fatty acid or the like, derived from an infectious agent. In other embodiments, the antigen can be a subunit or fragment of a polypeptide, or a fragment of a nucleic acid or polysaccharide derived from an infectious agent. In certain embodiments, the antigen is a recombinant polypeptide produced in a heterologous expression system, e.g., a recombinant protein derived from an infectious agent that was expressed in and purified from cells of another organism. However, an antigen can also be a recombinant nucleic acid construct which encodes a polypeptide antigen of interest (e.g., an expression construct). The antigen can include a viral subunit, a virus-like particle, a capsular (poly) saccharide; a bacterial outer membrane bleb formation containing one or more of bacterial outer membrane proteins, a phospholipid, a lipopolysaccharide, or a polysaccharide.

In some embodiments, the antigen can be a naturally occurring substance. In certain embodiments, the antigen comprises or is derived from an allergen, e.g., pollen. In certain embodiments, the antigen comprises or is derived from a toxin. In certain embodiments, the antigen comprises or is derived from an addictive substance, including, without limitation, nicotine, caffeine, alcohol, and the like. In yet other embodiments, the antigen can be a non-naturally occurring (e.g., synthetic) substance, e.g., a synthetic peptide, a synthetic polysaccharide, or a synthetic polymer.

In other embodiments, the antigen is a tumor cell or is derived from a tumor cell, including cells from any of the types of cancers or tumors described herein.

In certain aspects, the antigen can be provided in a vaccine, e.g., any vaccine known in the art. The vaccine can be a nucleic acid construct (e.g., a DNA vaccine). The vaccine can be a viral vector vaccine, which uses live viruses to carry DNA into an individual's cells. The DNA contained in the viral vaccine encodes antigen(s) that, once expressed in the infected cells, elicit an immune response. Alternatively, the vaccine can be a subunit vaccine, e.g., a specific protein from a virus. The vaccine can be a dendritic cell vaccine, in which an individual's dendritic cells are cultured with an antigen and then re-injected into the individual to stimulate an immune response. In certain embodiments, the vaccine can be a monovalent vaccine, e.g., containing a single antigen. In certain embodiments, the vaccine containing the antigen is a polyvalent or multivalent vaccine, e.g., containing more than one antigen.

The amount of antigen to be included in compositions disclosed herein and used in the methods of the present invention depends on the target and on immunogenicity of the antigen itself and the efficacy of any adjuvants co-administered therewith. In general, an immunologically effective dose can include but is not limited to a concentration of about 1 µg to about 1000 µg of the antigen, about 5 µg to about 500 m about 10 µg to about 200 µg. In some embodiments, an immunologically effective dose can be at least about 1, at least about at least about 10 at least about 25 at least about 50 at least about 100 at least about 150 µg, at least about 200 at least about 250 at least about 300 at least about 350 µg, at least about 400 at least about 450 at least about 500 m, at least about 550 m, at least about 600 m, at least about 650 at least about 700 at least about 750 at least about 800 at least about 850 at least about 950 m, or up to about 1000 µg of antigen. In embodiments where the antigen is a recombinant protein or peptide, a suitable dose can be about 10-100 µg. In embodiments where the antigen is a recombinant protein or peptide, a suitable dose can be about 10-100 µg.

Pharmaceutical Compositions

In some embodiments, the present invention can include pharmaceutical compositions designed for mucosal immune stimulation as well as other non-specific immune stimulation. In accordance with these embodiments, the composition includes a liquid immune stimulant, formulated with a pharmaceutically acceptable carrier, diluent or excipient. In other embodiments, the composition includes a viscous solution having HMW/high viscosity adhesion agents with improved adhesion properties formulated with a pharmaceutically acceptable carrier, diluent or excipient. Any known diluents, excipients and carriers in the art are contemplated of use herein. Compositions may be in an aqueous form or semi-solid form capable of being delivered through a dropper. In the most desirable formulation, the immune stimulant would be prepared as a stable liquid (during refrigeration) in an acceptable carrier. In other instances, the immune stimulants may be lyophilized during manufacture, to be reconstituted later into an aqueous form at the time of use. In certain embodiments, composition of the instant invention can be liquid, semi-liquid, semi-solid or dried, such as a lyophilized formulation. In certain embodiments, the compositions can be a stable liquid, semi-liquid, or semi-solid formulation stable at room temperature for prolonged periods.

In some embodiments, immunogenic compositions disclosed herein are very stable having improved tolerance for high temperatures or moderate temperatures for prolonged periods. In accordance with these embodiments, the immunogenic compositions with or without high viscosity/HMW adhesion agents are stable at room temperature (e.g. 25° C.) for at least one week, at least one month, at least 2 months, at least 3 months, at least 4 months or more. In certain embodiments, ocular immunotherapy compositions that include at least one high viscosity/HMW adhesion agent is stable at elevated temperatures and pressures. For example, these compositions are stable during autoclaving, an advantage for assuring sterility of the compositions during the manufacturing process and for use in a subject having an eye condition contemplated herein.

In certain embodiments, pharmaceutical compositions of the present invention are formulated for delivery by a variety of mucosal routes of delivery, including intranasally, orally, intrarectally, intravaginally, or by the intra-mammary or intra-uterine route, or by aerosol mist exposure, or by dilution in water (fish). Alternative routes of delivery include parenterally, e.g., intravenously, subcutaneously, intraperitoneally, or intramuscularly.

Kits

In some embodiment, composition can be present in one or more containers or vials, e.g., single use or multiuse containers or vials. In some embodiments, multiuse vials can include a rubber diaphragm suitable for retrieving multiple doses of the immune stimulant. The composition may also be supplied in flexible plastic bags that can be connected to multi-dose intranasal syringes, as in a feedlot operation. The composition may also be further diluted in a suitable diluent for administration in an aerosol delivery device that can be worn as a backpack for administration to poultry, or in a dispensing device suitable for delivery into water for treatment of fish. In some embodiment, immunogenic compositions disclosed herein can be in a dropper bottle, a tube, an eye delivery device, a syringe or other suitable container. In other embodiments, the immunogenic composition can be part of a kit and further include a delivery device.

In some embodiments, the kit or composition can include for a single dose, or multiple doses. In some embodiments, a kit containing an immunostimulatory composition can include a preservative. In some embodiments, a delivery device can include a bulb tip or other delivery tip. In other embodiments, a syringe can be used to or is adapted for use to deliver the composition to by any delivery mode contemplated herein. For example, delivery directly to the nasal cavity, oral cavity, to the eye (e.g. cornea) and/or pharyngeal region of a mammal. In certain embodiments, the subject is an animal such as a mammal (e.g. horse, dog, cat, cow, pig, sheep, goat, rabbit) or bird (e.g. chicken, turkey, duck) or fish (e.g., talapia, salmon, trout, catfish).

Methods of Treatment—Stimulation of Innate Immune Response

In certain embodiments, methods of inducing an immune response in a subject are disclosed. In certain embodiments, immunogenic compositions disclosed herein are administered to a subject in order to induce a non-specific immune response. In certain aspects, the composition is administered in a therapeutically effective amount. In further aspects, the composition is administered in a prophylactically effective amount. In yet other embodiments, doses for treatment of cattle can be in the range of 1 ml to 5 ml of immunogenic compositions disclosed herein (e.g. PCT-01) administered into each nostril, for goats and sheep, 0.5 ml to 3 ml immunogenic compositions disclosed herein (e.g. PCT-01) in each nostril, for dogs 0.1 ml to 3 ml immunogenic compositions disclosed herein (e.g. PCT-01) in each nostril (and 1 ml to 5 ml orally), for cats 0.1 ml to 2 ml immunogenic compositions disclosed herein (e.g. PCT-01) in each nostril and 0.5 to 3 ml orally. For treatment of poultry, an example dose could be 1 to 100 ml immunogenic compositions disclosed herein (e.g. PCT-01) diluted in 100 to 1000 ml of suitable diluent (e.g., saline, D5W) and administered as an aerosol to treat a 30 by 30 foot room with 100 chickens. For treatment of fish, and example dose can be about 1.0 to 50 ml immunogenic compositions disclosed herein (e.g. PCT-01) diluted in 1000 to 10,000 gallons of water for 24 h of treatment. In humans, the intranasal dose of immunogenic compositions disclosed herein (e.g. PCT-01) can be about 0.1 to about 2 ml administered in each nostril.

In some embodiments, the subject is a mammal at risk of infection by a pathogenic agent (or already infected with such an agent), such as a virus, fungus, prion, protozoan or bacterium, or an infected subject. Examples include but are not limited to: 1) prevention or early treatment of kennel cough in dogs, or upper respiratory tract infection syndrome in cats; 2) prevention or early treatment of bovine respiratory tract disease (BRD) syndrome in cattle (beef or dairy); 3) prevention or early treatment of respiratory tract disease in swine, sheep, or goats; 4) intra-mammary infusion for prevention or treatment of mastitis in cattle; 5) intra-uterine infusion for prevention or early treatment of metritis in cattle or horses; 6) oral administration for treatment of inflammatory bowel disease in dogs, cats, humans; and 7) intra-nasal administration for prevention or early treatment of viral upper airway infections in humans.

In another embodiment, the subject is a bird at risk of infection, or already infected. Examples of methods for birds include, but are not limited to, prevention or treatment of viral, fungal, protozoan, or bacterial respiratory tract infections (e.g., influenza infection) in poultry (e.g. chickens, turkeys, ducks) in intensive rearing conditions (e.g., boiler operations, egg laying facilities). In addition, the composition could be directly administered to eggs (e.g. in ovo) for induction of innate immune responses in the developing embryo to improve hatchability and early resistance to infection.

In another embodiment, methods are disclosed to treat fish for example to treat an infection or reduce onset of an infection in a fish population. Examples include but are not limited to prevention or treatment of viral, fungal, bacterial or protozoal infections in fish. For example, in fish farms. Examples include, but are not limited to, fish in aquaculture settings (e.g., talapia, trout, salmon, catfish), where an immunogenic composition could be administered by diluting in water in small treatment ponds or tanks for periods of several hours of days of treatment.

In certain embodiments, the composition is provided by a variety of mucosal routes of delivery, including intranasally, orally, inter-rectally, intravaginally, or by the intra-mammary or intra-uterine route, or by aerosol mist exposure, or by dilution in water (e.g., fish). Alternative routes of delivery include parenterally, e.g., intravenously, subcutaneously, intraperitoneally, or intramuscularly.

According to certain embodiments, administration of the composition is applied to a mucosal surface. According to certain exemplary embodiments, the composition is applied topically to the nose, eyes, mouth, upper airways, air sacs, gills, ears, eyes, uterus, mammary gland, and or gastrointestinal tract.

Methods of Treatment—Stimulation of Antigen-Specific Immune Response

According to certain alternative embodiments, methods disclosed herein concern inducing an immune response, e.g., an immune response specific to an antigen, by providing a composition (e.g., a vaccine composition) of the present invention to a subject in need thereof. In particular embodiments, the subject is a mammal at risk of an infection due to a pathogen.

Particular embodiments include methods of treating or preventing an infection, for example, a lung infection. In accordance with these embodiments, immunogenic compositions disclosed herein can be used to treat or reduce the onset of an infection by administering to a subject in need thereof an effective amount of the immunogenic composition in combination with an antigen, e.g. a protein antigen, an antigen derived from a virus, fungus, prion, or bacterium.

In some embodiments, include treating or preventing a cancer in a subject in need thereof, including providing to the subject an effective amount of a cancer antigen in combination with an immunogenic composition of the present invention. In other embodiments, immunogenic compositions disclosed herein can be used to treat a subject having cancer for inhibiting tumor growth, reducing tumor size, and inhibiting tumor metastasis, as well as reducing side effects of tumors such as chronic ulcers. In some embodiments, tumor growth, tumor size, or tumor metastasis is inhibited or reduced by at least 10%, 20%, 30%, 40%, 50%, 60%, 70%, 75%, 80%, 85%, or 90% in a subject when compared to treatment without immunogenic composition as disclosed herein. In certain embodiments, the subject has a tumor (e.g. a metastatic tumor). In other embodiments, the subject is considered to be at risk of cancer or tumor metastasis. In some embodiments, the subject has a tumor of the eye.

In some embodiments, a tumor can be any type of tumor from any type of cancer such as a solid tumor or liquid tumors or other tumor. In certain embodiments, the cancer is breast cancer, lung cancer, prostate cancer, colorectal cancer (e.g., colon carcinoma), brain cancer, glioblastoma, skin cancer, melanoma, eye, cancer esophageal cancer, stomach cancer, bladder cancer, pancreatic cancer, cervical cancer, head and neck cancer, ovarian cancer, melanoma, leukemia, myeloma, lymphoma, glioma, Non-Hodgkin's lymphoma, leukemia, multiple myeloma or multidrug resistant cancer.

Some embodiments disclosed herein concern eye metastatic cancers and tumors. In one example, one primary malignant intraocular cancers is uveal melanoma (in adults) and another is retinoblastoma (in children). In certain embodiments, immunogenic compositions disclosed herein can be used alone or in combination to treat cancer of the eye. In some embodiments, depending upon the type and stage of eye cancer, combination treatment options can include, but are not limited to, surgery, radiotherapy, laser therapy, chemotherapy (ChT), and targeted therapy. Other combination therapies can include eye-sparing therapies for retinoblastoma, including brachytherapy and systemic and intra-arterial ChT.

In some embodiments, eye neoplasm can mean a cancerous growth in any part of the eye (e.g. eyeball, orbit, or adnexal structures). Eye cancers can be grouped into three basic categories according to their location: tumors of the eyelid and conjunctiva; intraocular tumors; and orbital tumors. Eye cancers can be classified as primary (e.g. starts within the eye) or metastatic (e.g. originated from another region and spreads to the eye). The most common primary malignant intraocular tumor in adults is uveal melanoma (UM). The two most common cancers that metastasize to the eye from another organ are breast cancer and lung cancer as well as less common cancers including, but not limited to, prostate, kidney, thyroid, skin, colon, lymphoma, and leukemia. The most common malignant intraocular tumor in young children is retinoblastoma. It is contemplated herein the immunogenic compositions disclosed herein (e.g. MiM plus a HMW/high viscosity adhesion agent) can be used alone or in combinations to treat tumors of the eye.

Some embodiments disclosed herein can include combination therapies using immunogenic compositions disclosed herein in combination with immunotherapy. Immunotherapies can include use of cytokines, monoclonal antibodies, and/or vaccines. In certain embodiments, targeted therapy can include chemotherapy drugs.

In some embodiments, an effective amount of an immunogenic composition can include about 0.1 ml to about 5.0 ml (e.g., about 1 ml) of TLR ligand; and about 1% to about 20%, about 2% to about 15%, about 2.5% to about 10%, about 5% to about 10%, or about 5% (v/v) of a cellular adhesion agent, such as carboxymethylcellulose or a PEG. In some embodiments, the effective amount includes: optionally, 100 to 500 ug of antigen; and about 1-4 ml of cationic liposome-DNA complexes; about 5% to about 10% (v/v) of carboxymethylcellulose.

In certain embodiments, the immunogenic compositions alone or in combination with an antigen can be administered in a single dose or in two, three, four, five, six, seven, eight, nine, ten or more dosing regimens. In some embodiments, the immunogenic composition can be provided daily, every other day, twice a week, weekly, every other week, once a month, or once every other month depending on the condition (e.g. eye condition)

EXAMPLES

The following examples are included to illustrate various embodiments. It should be appreciated by those of skill in the art that the techniques disclosed in the examples which follow represent techniques discovered to function well in the practice of the claimed methods, compositions and apparatus. However, those of skill in the art should, in light of the present disclosure, appreciate that changes may be made in the some embodiments which are disclosed and still obtain a like or similar result without departing from the spirit and scope of the invention.

Example 1

Figure 1:
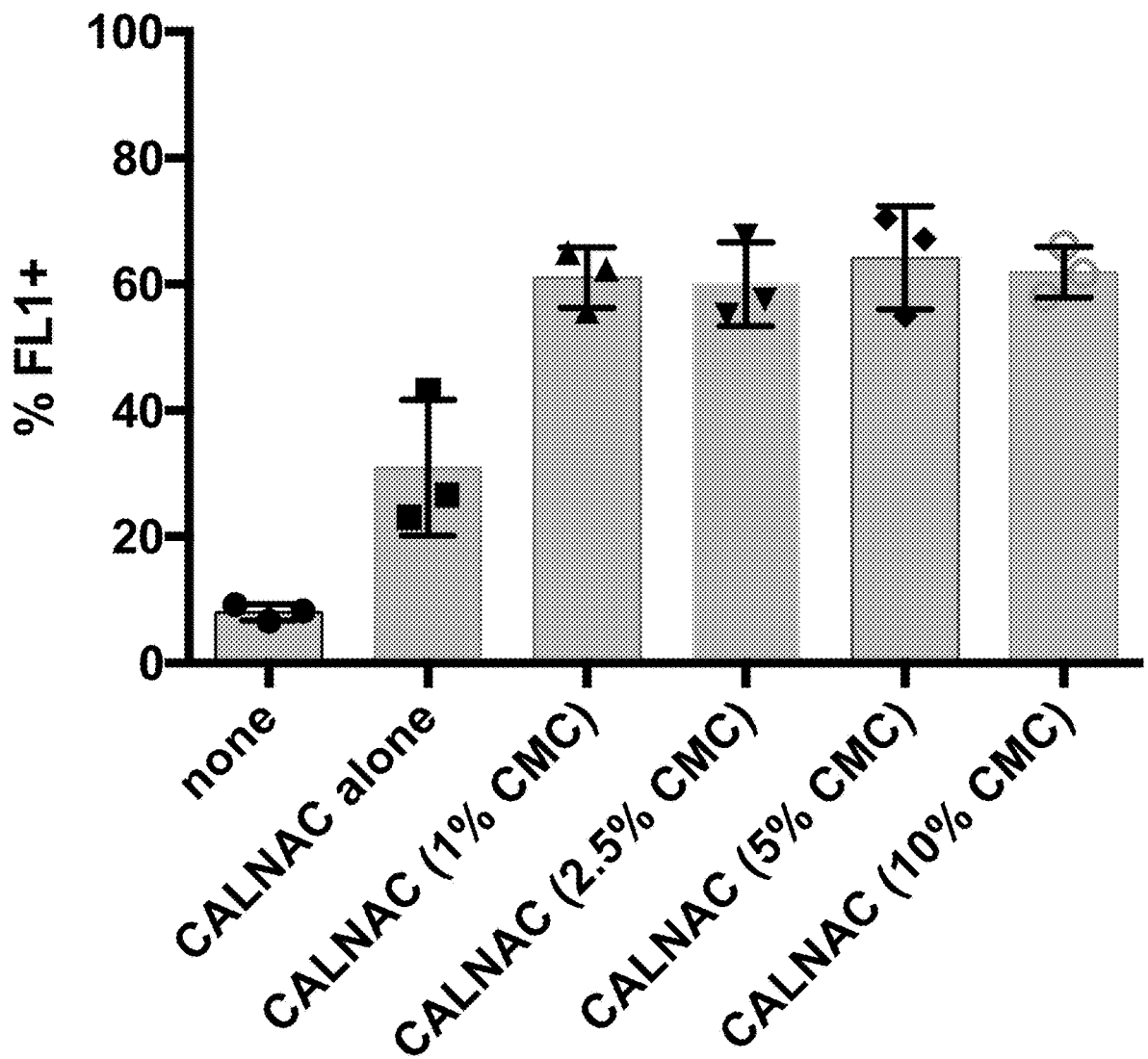
FIG. 1 illustrates flow cytometric data demonstrating that CMC addition to liposome-TLR3/9 complexes (CALNAC, cationic liposome nucleic acid complexes) increases adhesion to epithelial cells of some embodiments disclosed herein.

In one exemplary method, to test the effects of adding carboxy-methylcellulose (CMC) on the adhesion properties of liposome-TLR3/9 complexes, complexes of liposomes and DNA and TLR3/9 agonists (plasmid DNA and pIC) were labeled with a fluorescent dye, and adherence to a rat epithelial cell line was evaluated by a 3 h assay with shaking in an incubator. The effects of adding different concentrations of CMC to liposome-TLR3/9 complexes (CALNAC) was assessed by flow cytometric measurement of the percentages of epithelial cells containing liposome-TLR3/9 complexes. As best shown in FIG. 1, the addition of CMC to liposome-TLR3/9 complexes increases adhesion to epithelial cells.

Example 2

In one exemplary method, in order to assess the effects of combining TLR3 and TLR9 agonists with liposomes, spleen cells from mice were incubated with cationic liposomes alone, or liposomes+pIC or liposomes plus pDNA, or liposomes plus both pIC and pDNA. Immune stimulation (IL-12 release) was measured by ELISA assay. The combination of both TLR3 and TLR9 agonists generated synergistic immune activation. See for example, FIG. 1, the combination of TLR3 and TLR9 agonists with liposomes increases potency of immune activation.

Example 3

Figure 2:
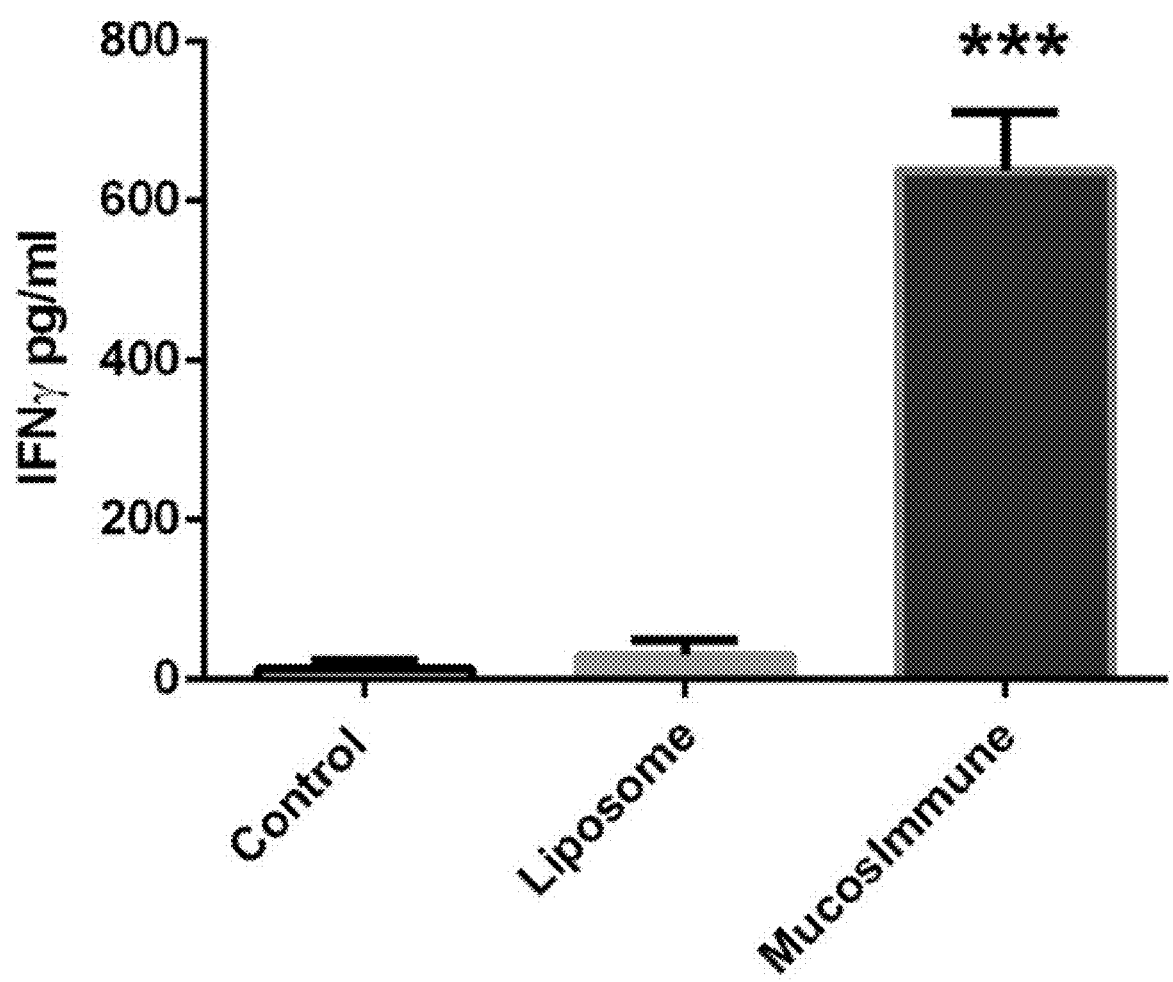
FIG. 2 illustrates data from a canine PBMC stimulation assay demonstrating increased immune stimulatory potency by inclusion of CMC with an immune stimulatory complex (CALNAC, cationic liposome nucleic acid complexes). of some embodiments disclosed herein.

In another exemplary method, in order to evaluate the effect of CMC on the immune potency, canine PBMC were incubated with CLDC complexes or CLDC+10% CMC for 24 h. IFN-γ release measured by ELISA as an indication of immune stimulation potency. FIG. 2 illustrates that the immune potency comparison of complexes of cationic liposomes and pIC and pDNA alone (CLDC) or CLDC plus 10% CMC (PCT-01). Complexes of CLDC+CMC (PCT-01) were significantly more immune stimulatory than CLDC complexes.

Example 4

Figure 3:
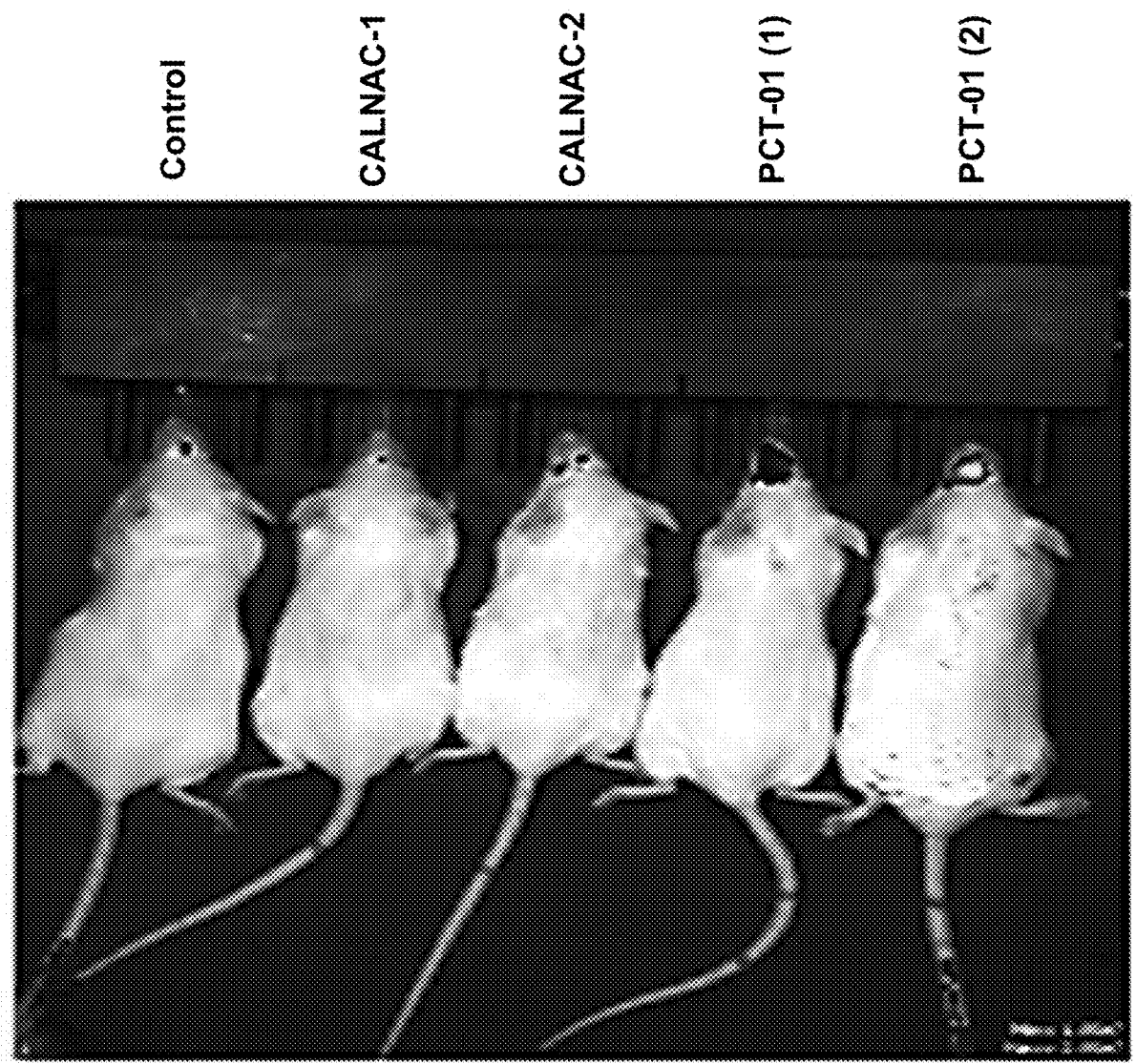
FIG. 3 illustrates exemplary imaging data from mice demonstrating increased in nasal cavity adhesion Animals are administered an immune stimulant (CALNAC, cationic liposome nucleic acid complexes) combined with CMC (e.g., PCT-01) and compared to administration of (CALNAC, cationic liposome nucleic acid complexes) alone of some embodiments disclosed herein.

In another exemplary method, to test the ability of CMC to affect adhesion to mucosal surfaces, mice were administered intranasally 50 μl CLDC or CLDC+CMC that had been labeled with a fluorescent dye to allow tracking in a live animal imager (IVIS). The amount of labeled material still present in the nostrils 60 min after administration was determined by live animal imaging. As illustrated in FIG. 3, compared to control animals (n=1) and animals administered CLDC (labeled CALNAC) alone (n=2), animals treated with CLDC+CMC (PCT-01, n=2) had significantly more material retained in their nostrils, indicating CMC contributes to mucosal surface adhesion.

Figure 4:
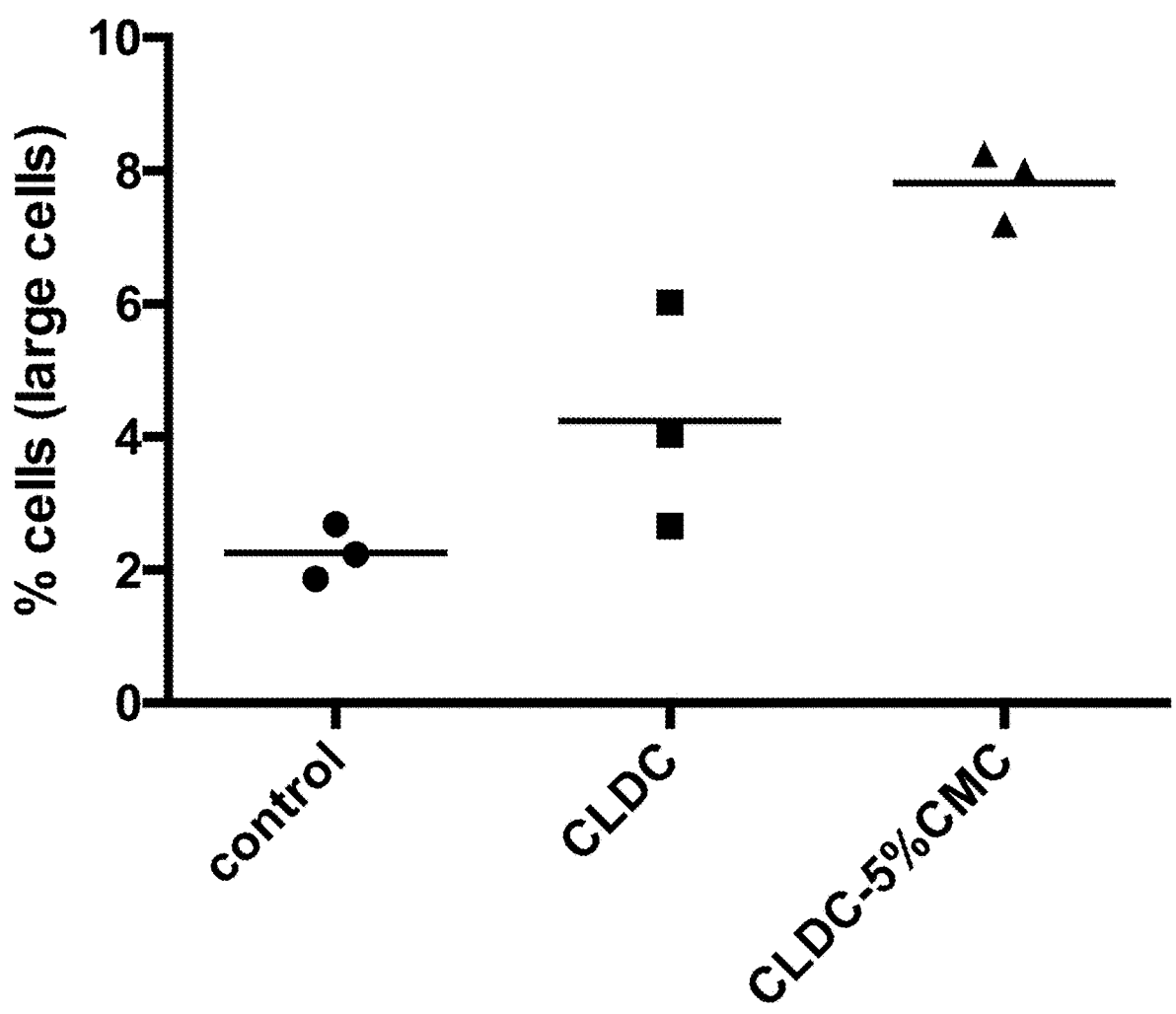
FIG. 4 illustrates exemplary flow cytometry data demonstrating increased immune response to an immunogenic composition (e.g., PCT-01) administered in the oropharynx of mice compared to CLDC (cationic liposome nucleic acid complexes) alone treatment groups of some embodiments disclosed herein.
Figure 5:
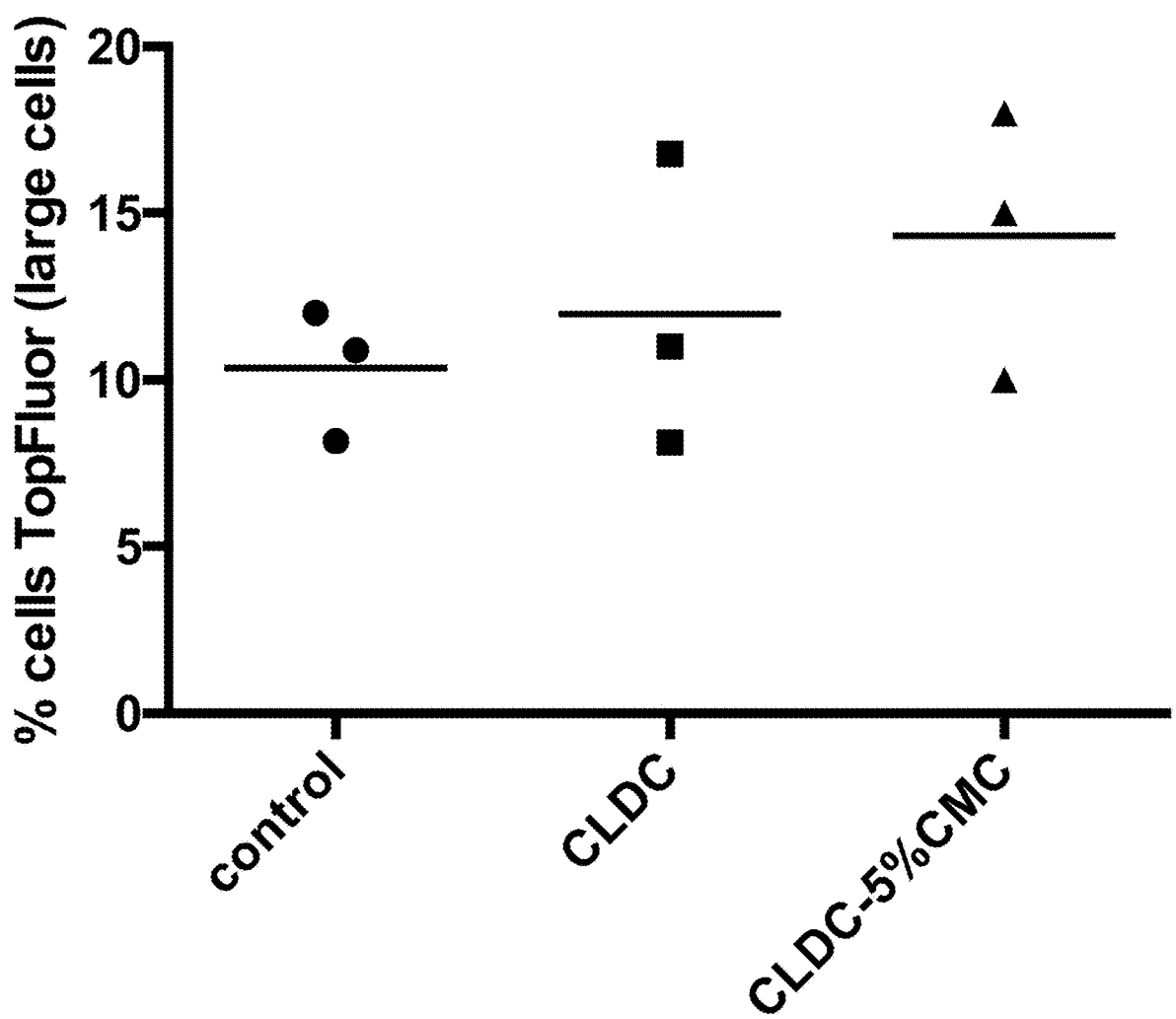
FIG. 5 illustrates exemplary flow cytometry data demonstrating increased immune response to an immunogenic composition (e.g., PCT-01) administered in oropharynx of mice compared to CLDC alone treatment groups of some embodiments disclosed herein.

In yet another exemplary method, to assess the effect of CMC on the ability of CLDC to elicit immune response, mice (n=3 per group) were administered CLDC or CLDC+CMC (ie, PCT-01) orally, and 24 hours later, infiltrates of immune cells into the oropharynx was assessed by flow cytometry, using cells obtained from the oropharynx by swabs. As illustrated in FIG. 4, compared to control animals and animals treated with CLDC, animals treated with PCT-01 had a much stronger influx of immune cells into the oropharynx. To test the effect of nasal administration, mice (n=3 per group) were administered CLDC or CLDC+CMC (e.g., PCT-01) intranasally, and 24 hours later, infiltrates of immune cells into the nasal cavity was assessed by flow cytometry, using cells obtained from the nasal cavity by nasal lavage. As illustrated in FIG. 5, compared to control animals and animals treated with CLDC, animals treated with PCT-01 had a much stronger influx of immune cells into the oropharynx.

Example 5

Figure 6A:
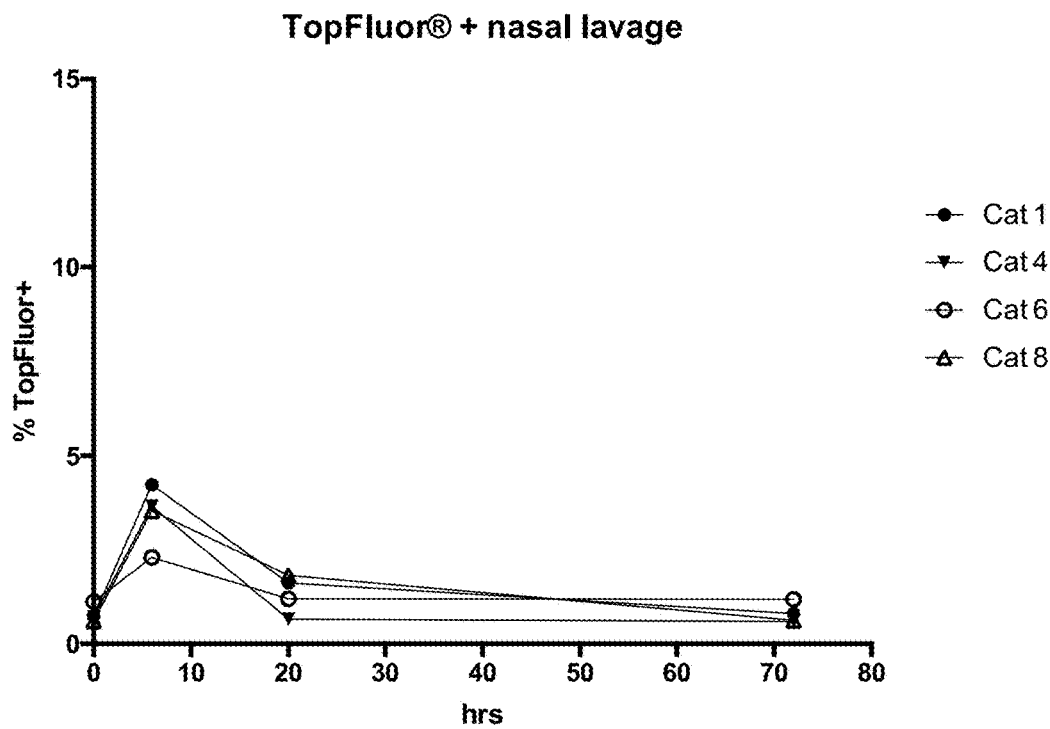
FIG. 6A illustrates exemplary flow cytometry data demonstrating liposome uptake by nasal cells in cats treated intranasally with CLDC of some embodiments disclosed herein.
Figure 6B:
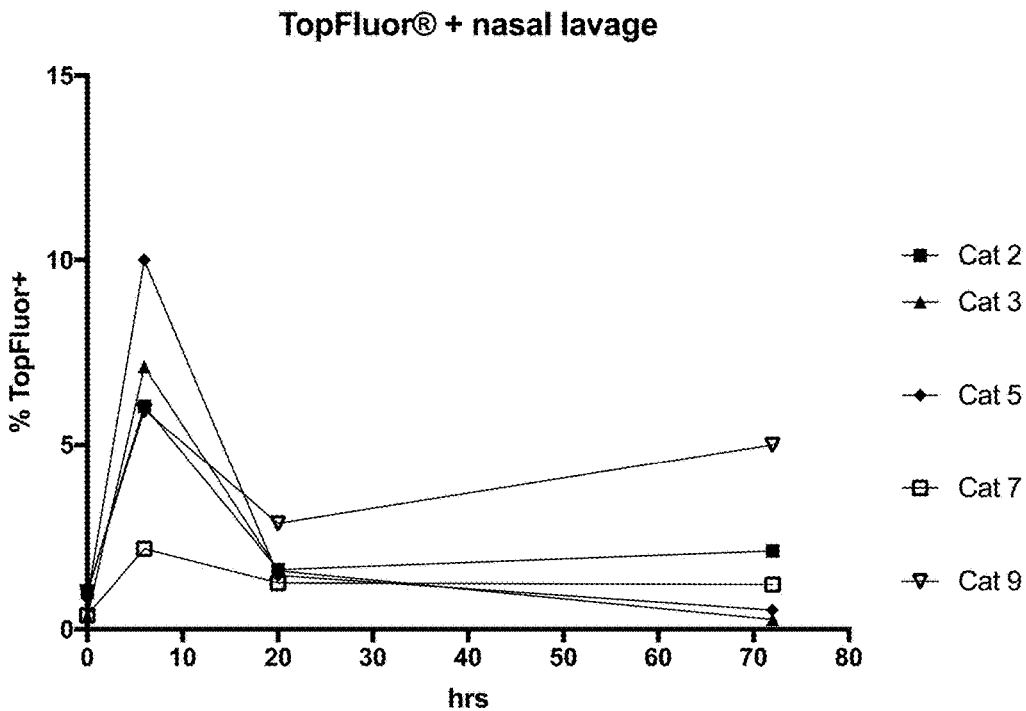
FIG. 6B illustrates exemplary flow cytometry data demonstrating liposome uptake by nasal cells in cats treated with an immunogenic composition (e.g., PCT-01) of some embodiments disclosed herein.
Figure 7A:
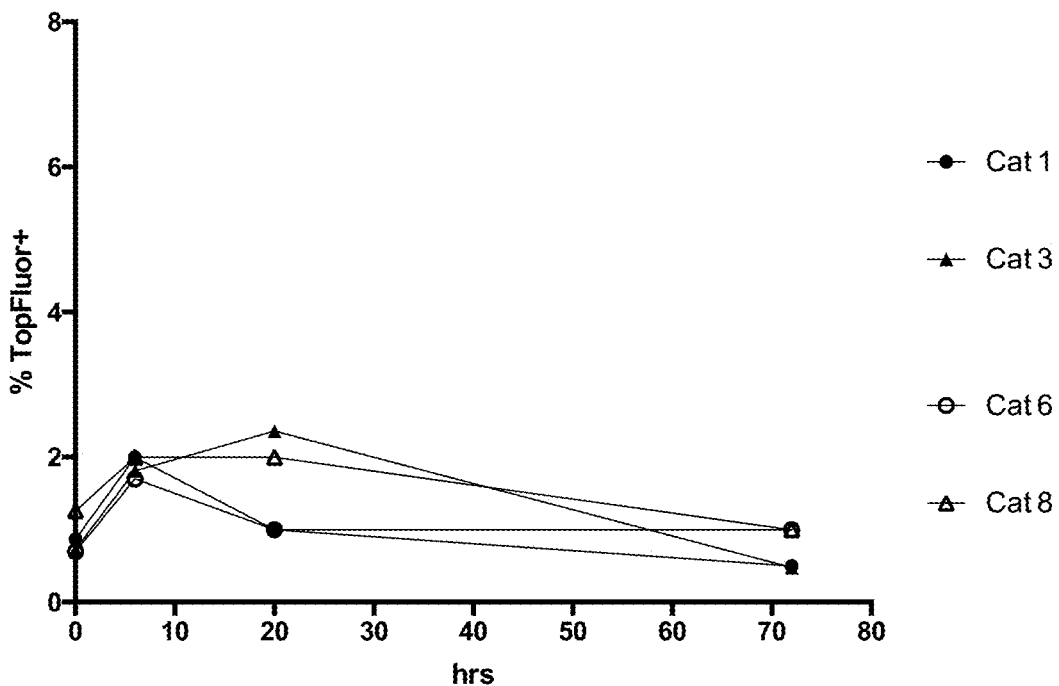
FIGS. 7A and 7B, 7A illustrates exemplary flow cytometry data demonstrating oropharyngeal cells from cats treated with CLDC alone.
Figure 7B:
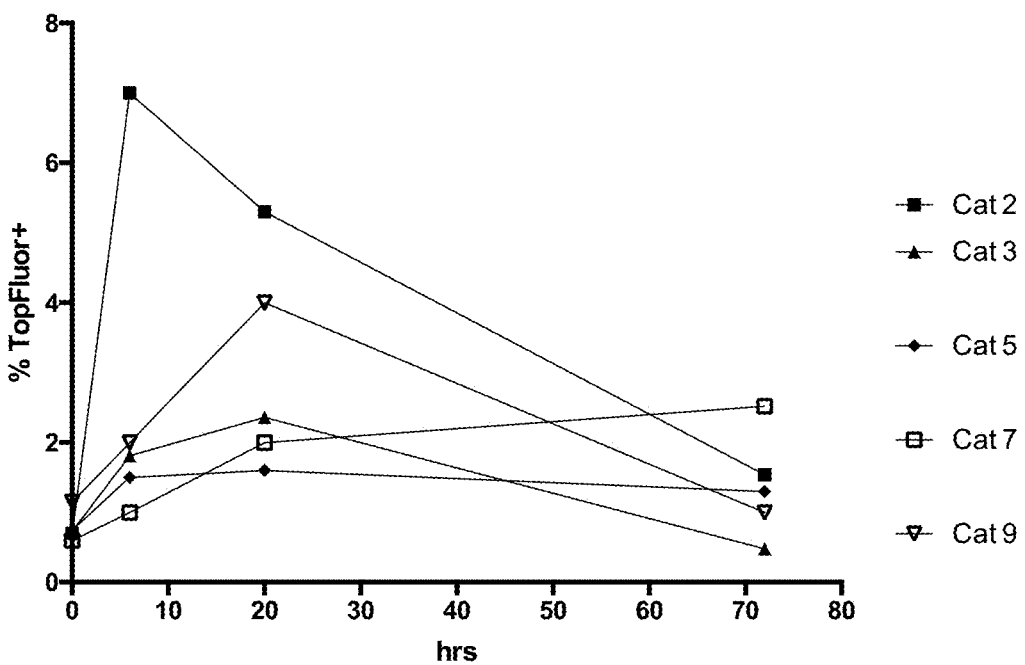

In one exemplary method, to assess the effect of CMC on the ability of CLDC to elicit immune response in felines, cats were treated intranasally with PCT-01 (CLDC+CMC) (n=5) and compared to cats treated with CLDC (n=4). To conduct the study, liposomes were labeled with a fluorescent dye to track their uptake by cells in the nasal and oropharyngeal mucosal. Healthy purpose-bred cats were treated intranasally with 0.3 ml labeled CLDC+CMC or labeled CLDC in each nostril. 24 hours later, nasal lavage samples were obtained and the percentage of cells that had contained labeled liposomes (TopFluor+) were compared between treatment groups, using flow cytometry. As illustrated in FIGS. 6 A & B, nasal cells from cats treated with PCT-01 (FIG. 6A) had substantially more liposomes than from cats treated with CLDC (FIG. 6B). The study was repeated to assess liposome uptake by cells in the oropharynx. Healthy purpose-bred cats were treated orally with 1 ml labeled PCT-01 (n=5) or labeled CLDC (n=4) in each nostril. 24 h later, oropharyngeal swab samples were obtained and the percentage of cells that had contained labeled liposomes (TopFluor+) were compared between treatment groups, using flow cytometry. As illustrated in FIGS. 7A & B, oropharyngeal cells from cats treated with PCT-01 (FIG. 7A) had substantially more liposomes than from cats treated with CLDC (FIG. 7B).

Figure 8A:
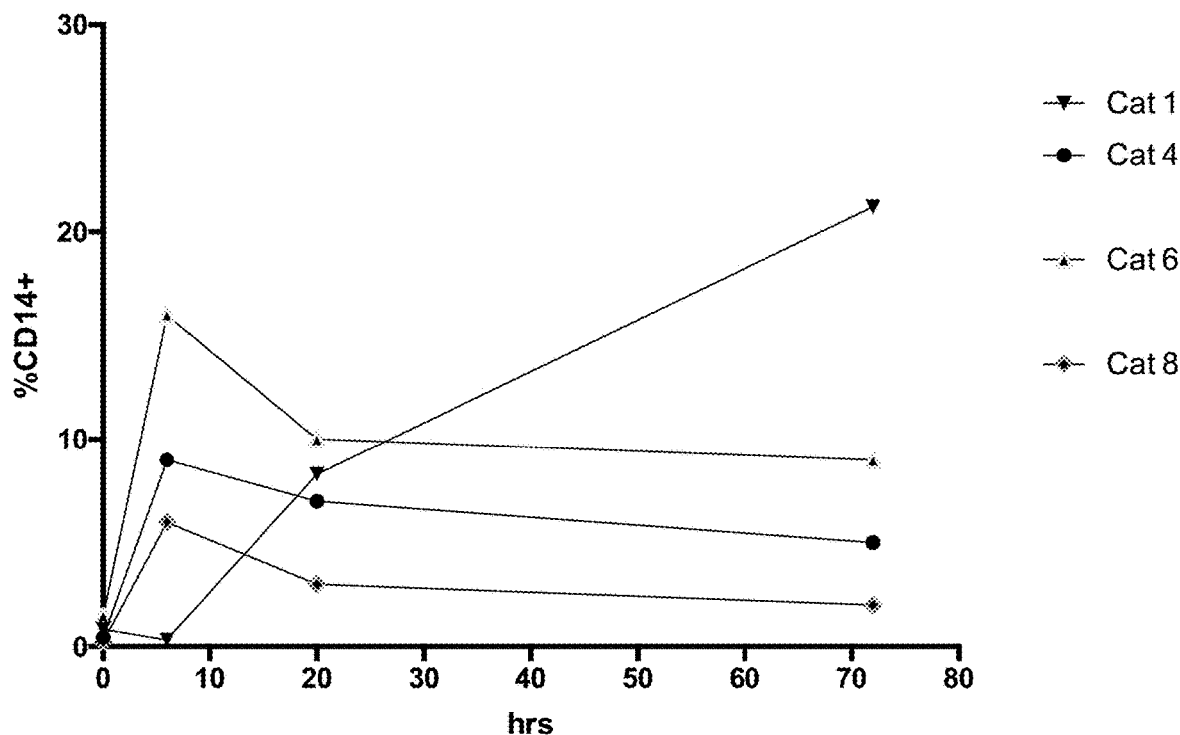
FIG. 8A illustrates exemplary flow cytometry data from the nose of cats treated intranasally with CLDC alone.
Figure 8B:
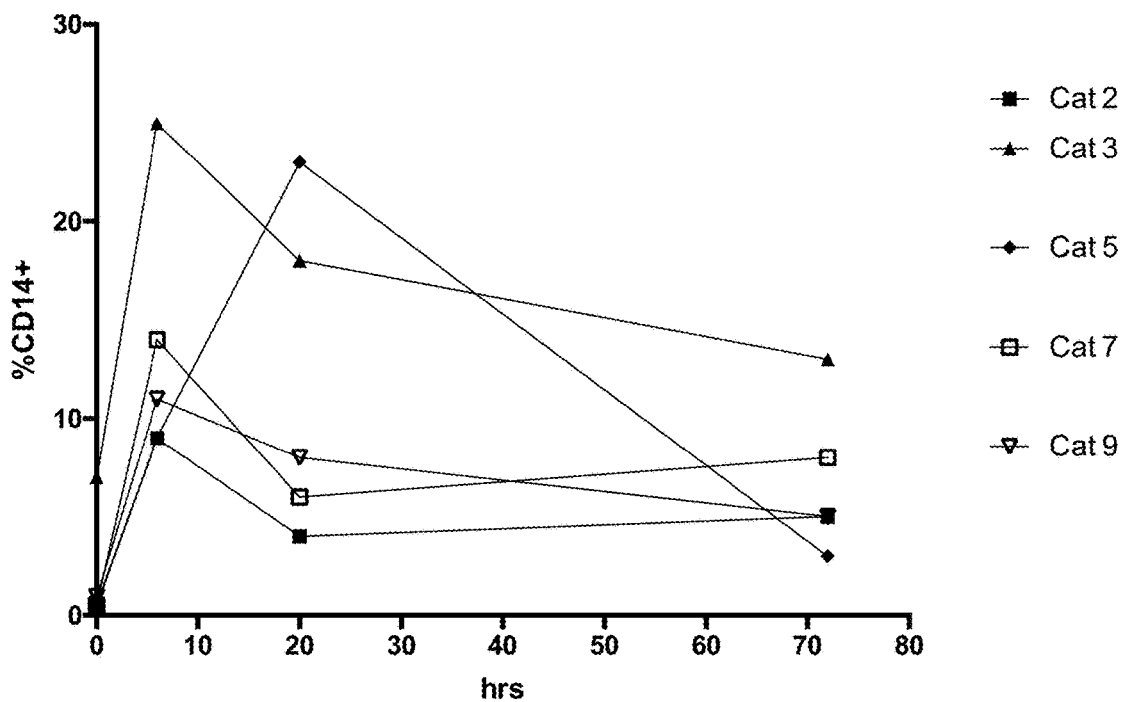
FIG. 8B illustrates exemplary flow cytometry data from nasal lavage samples from cats treated with an immunogenic composition (e.g., PCT-01: CLDC+CMC) of some embodiments disclosed herein.

FIGS. 8 A & B illustrate increase in recruitment of nasal immune cells in cats treated intranasally with PCT-01 (CLDC+CMC) (n=5) compared to cats treated with CLDC (n=4). Healthy purpose-bred cats were treated intranasally with 0.3 ml PCT-01 or CLDC in each nostril. 24 hours later, nasal lavage samples were obtained and the percentage of Cd14+ monocytes (immune cells) in the nose were compared between treatment groups, using flow cytometry. Nasal lavage samples from cats treated with PCT-01 (FIG. 8A) had substantially more CD14+ monocytes than from nasal lavage samples from cats treated with CLDC (FIG. 8B). Substantial infiltrates of monocytes were observed in both the nose and throat of the treated cats, attesting to local immune stimulation by PCT-01.

Example 6

Figure 9:
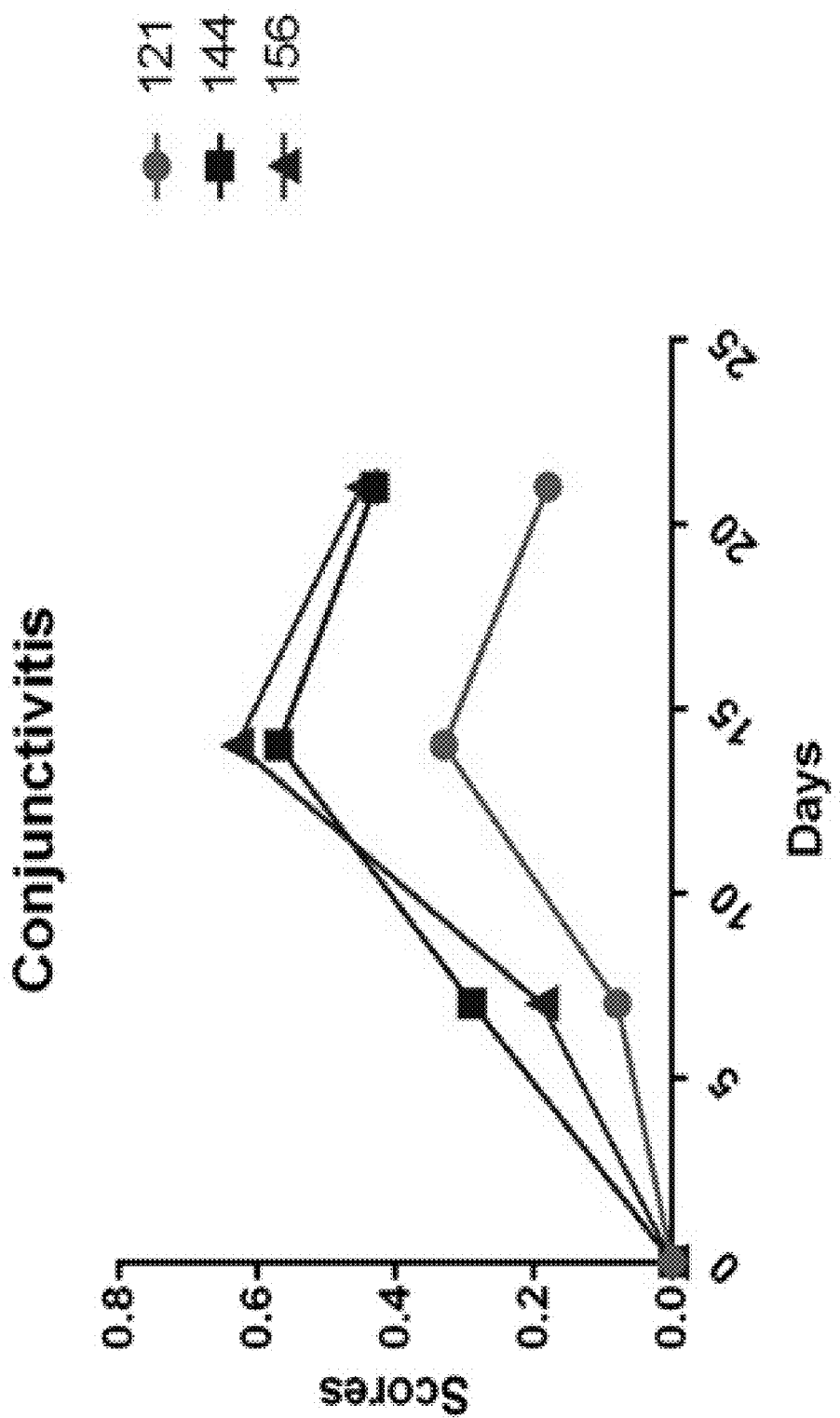
FIG. 9 illustrates exemplary data demonstrating reduced clinical signs of ocular conditions in cats challenged with FHV-1 and pre-treated 24 h prior to challenge with an immunogenic composition (e.g., PCT-01: CLDC+CMC) of some embodiments disclosed herein.
Figure 10:
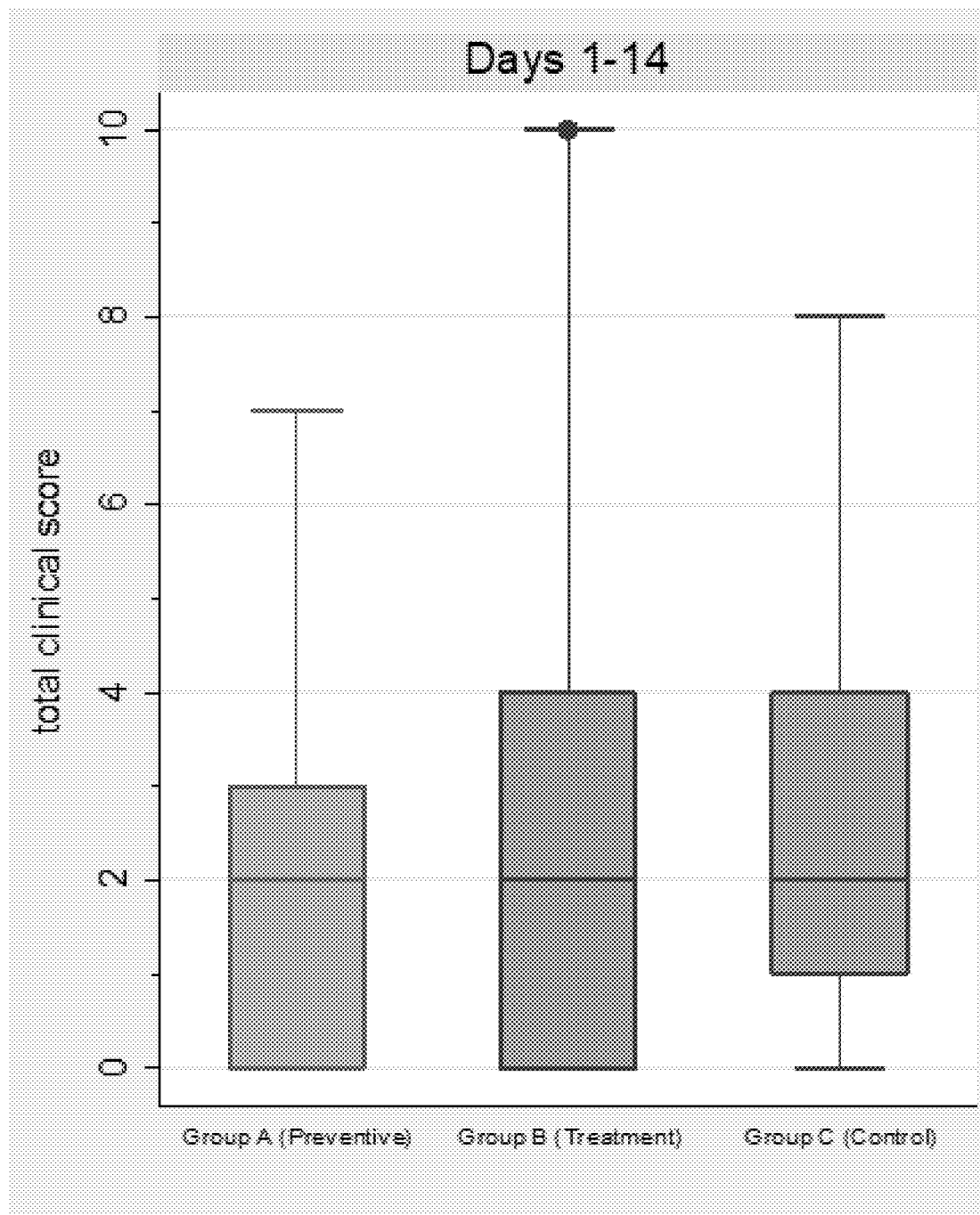
FIG. 10 illustrates exemplary clinical illness in cats pre-treated with an immunogenic composition (e.g., PCT-01: CLDC+CMC) 24 h prior to FHV-1 challenge of some embodiments disclosed herein.
Figure 11:
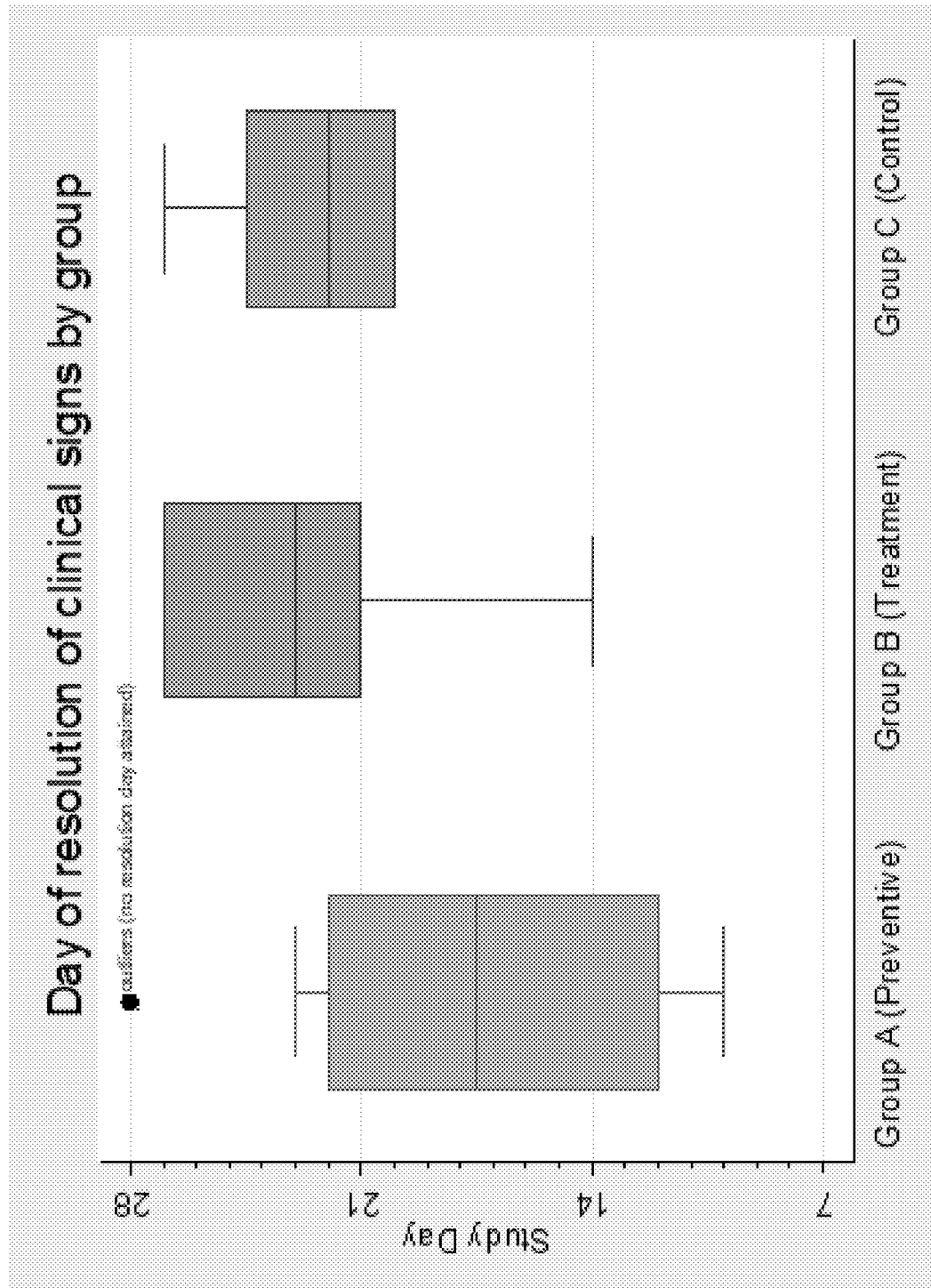
FIG. 11 illustrates exemplary clinical data indicating time to resolution of clinical signs significantly shortened in cats pre-treated with an immunogenic composition (e.g., PCT-01: CLDC+CMC) of some embodiments disclosed herein.

In another exemplary method, to test the ability of PCT-01 to affect clinical signs of ocular disease, a challenge study with feline herpesvirus type 1 (FHV-1) was conducted in purpose-bred cats. Three groups of cats (n=7 per group) including untreated control cats (group 156), cats pre-treated with PCT-01 24 h prior to challenge (group 121) and cats treated with PCT-01 when symptoms first developed (group 144), were monitored for clinical signs of infection (ocular signs, total clinical signs, body temp) and viral shedding by qRT-PCR for 28 days after the viral challenge was administered. As illustrated in FIG. 9, cats pre-treated with PCT-01 before challenge had a significant reduction in clinical ocular signs (squinting, ocular discharge) compared to control animals. As best seen in FIG. 10, total clinical scores in cats challenged with FHV-1 (FIG. 9) and pre-treated 24 h before challenge with PCT-01 were significantly lessened compared to control cats and cats treated after clinical signs developed. Furthermore, as illustrated in FIG. 11, cats challenged with FHV-1 and treated 24 h before onset of clinical signs experienced a significant reduction in the duration of clinical signs compared to control animals or animals treated once signs developed.

Figure 12:
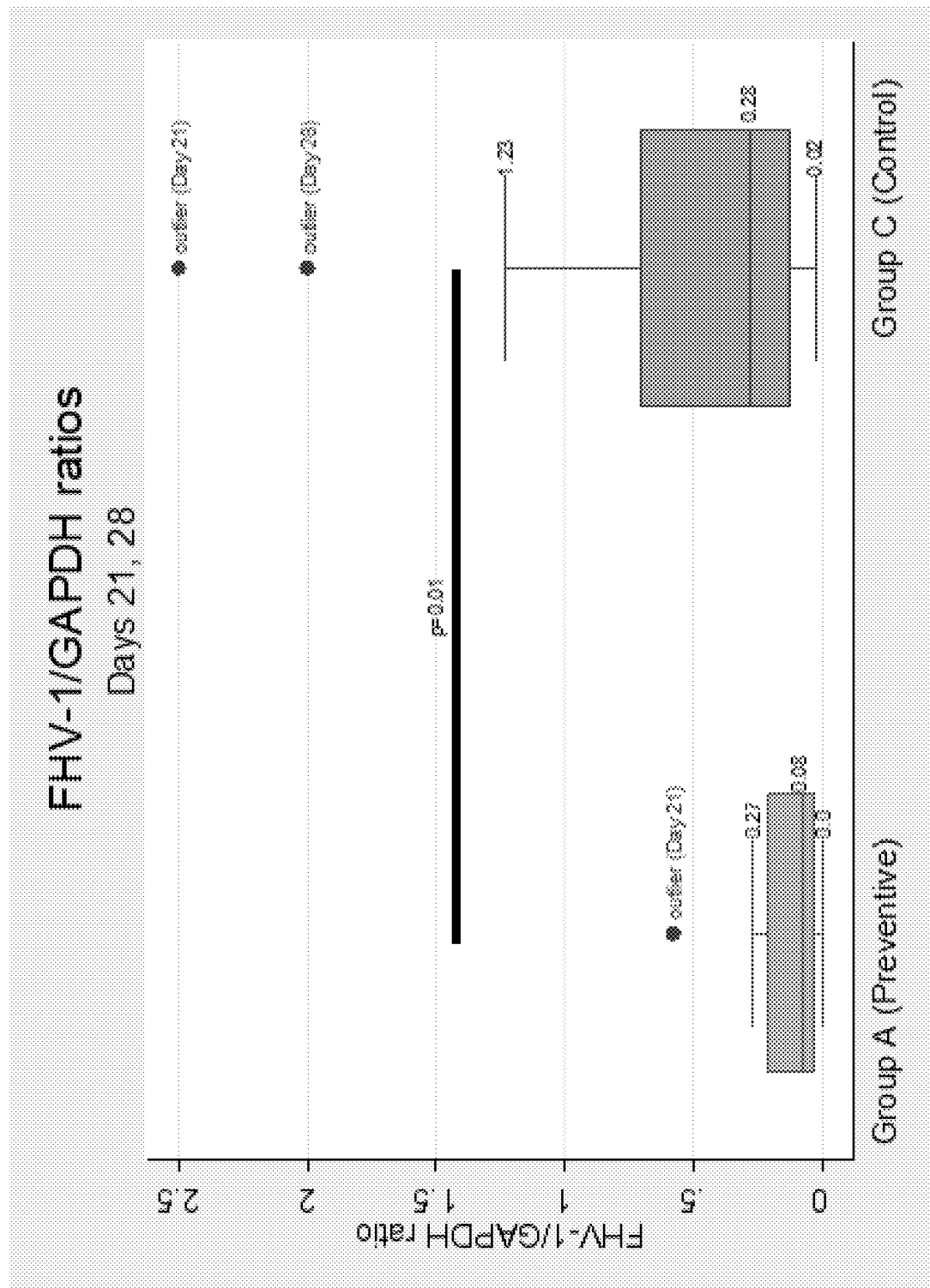
FIG. 12 illustrates exemplary qRT-PCR data indicating an immunogenic composition (e.g., PCT-01: CLDC+CMC) treatment significantly decreased viral shedding in cats challenged with FHV-1 of some embodiments disclosed herein.

FIG. 12 illustrates pre-treatment with PCT-01 significantly decreases viral shedding in cats challenged with FHV-1. Cats were pre-treated 24 h prior to FHV-1 challenge with PCT-01, and viral shedding from oropharyngeal swabs (as assessed by qRT-PCR) was compared to viral shedding by untreated control animals. As illustrated in FIG. 12, pre-treated with PCT-01 resulted in a significant decrease in viral shedding compared to untreated animals.

Example 7

In another exemplary method, to assess the uptake of labeled PCT-01 by nasal and oropharyngeal cells in dogs, labeled PCT-01 were administered intranasally and orally to a healthy adult dog. 6 h and 20 h later, nasal lavage and throat swab samples were obtained, and the percent of cells containing labeled liposomes determined. As illustrated in FIGS. 13 A & B, These studies found a substantial uptake of liposomes by nasal (FIG. 13A) and oropharyngeal (FIG. 13 B) cells at 6 h and 20 h after administration.

In another exemplary method, to assess the stimulation of immune cell infiltrates into nose and throat of dogs, PCT-01 was administered intra-nasally (0.5 ml per nostril) and orally (2 ml) in a healthy adult dog. The effects on immune cell infiltrates in the nose and throat was determined 6 h and 20 h later. As illustrated in FIGS. 14 A & B, substantial infiltrates of neutrophils and monocytes were observed in both the nose (FIG. 14A) and throat (FIG. 14B) of the treated dog, attesting to local immune stimulation by PCT-01. FIGS. 15 A & B illustrate stimulatory effect in the nose and mouth, as measured CD4 T cell infiltrates.

In another study, expression of cytokine genes in the oropharynx of dogs treated with PCT-01 was assessed at 3 time points (24 h, 72 h, 7 days) following treatment in healthy Beagle dogs (n=5), using qRT-PCR and primers designed for amplification of canine cytokine genes. As illustrated in FIG. 33, induction of cytokine expression was observed at 24 h, and persisted for at least 7 days in the treated dogs, consistent with the activation of local, mucosal immune responses by PCT-01.

Figure 16:
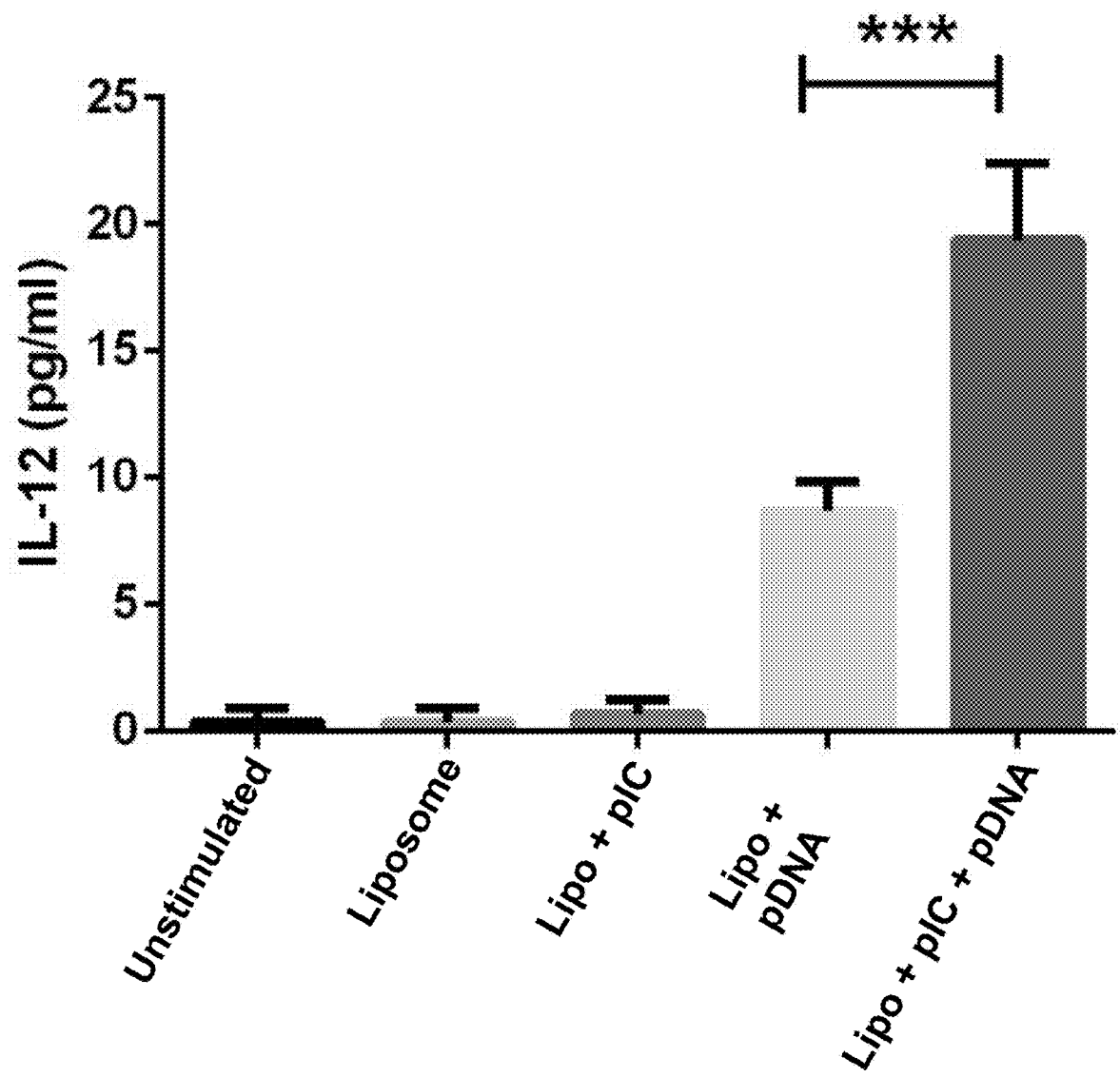
FIG. 16 illustrates exemplary IL-12 expression data indicating increased in vitro immune potency from combined TLR agonists, as present in an immunogenic composition (e.g., PCT-01: CLDC+CMC) of some embodiments disclosed herein.

FIGS. 16 A & B illustrate increased immune potency from combined TLR3 and TLR9 agonists. Spleen cells from mice were placed in culture in triplicate wells, and then incubated with the noted components for 24 hours to assess induction of immune activation (reflected by IL-12 secretion). While liposomes complexed with either polyIC or with plasmid DNA induced immune activation (IL-12 production), liposomes complexed with both pIC and pDNA together in the same complexes stimulated significantly greater immune activation.

Example 8

Figure 17A:
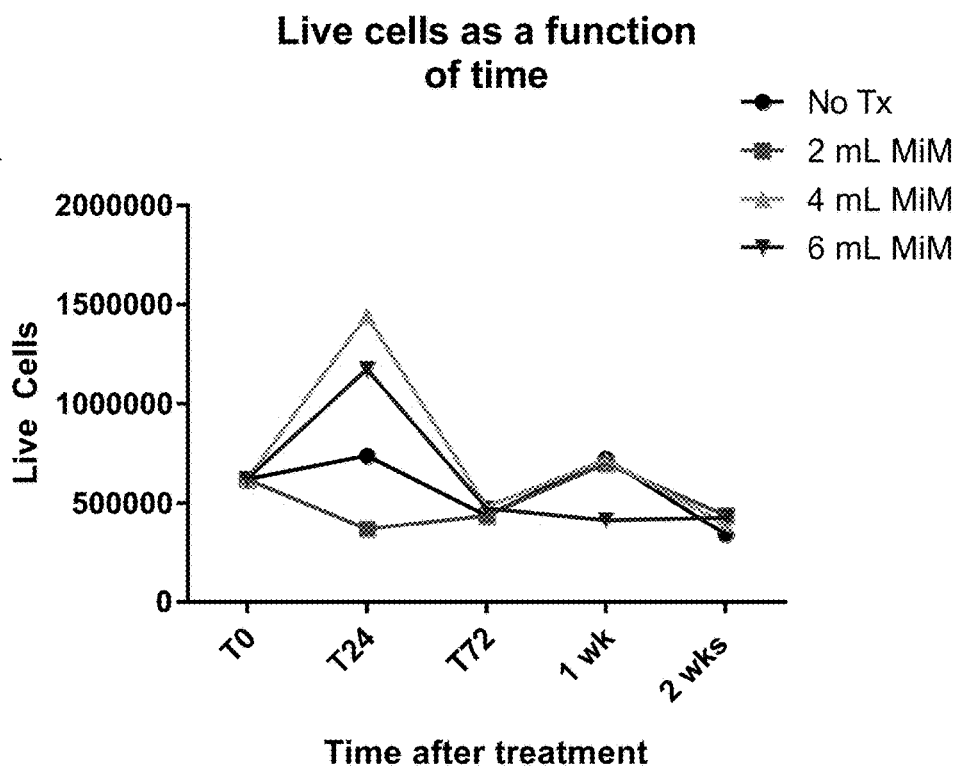
FIGS. 17A and 17B illustrate exemplary changes in nasopharyngeal cell counts from cattle over time following a single intranasal immunogenic composition (e.g., PCT-01: CLDC+CMC) administration of variable concentrations (17A) and a single concentration (17B) compared to a negative control of some embodiments disclosed herein.
Figure 17B:
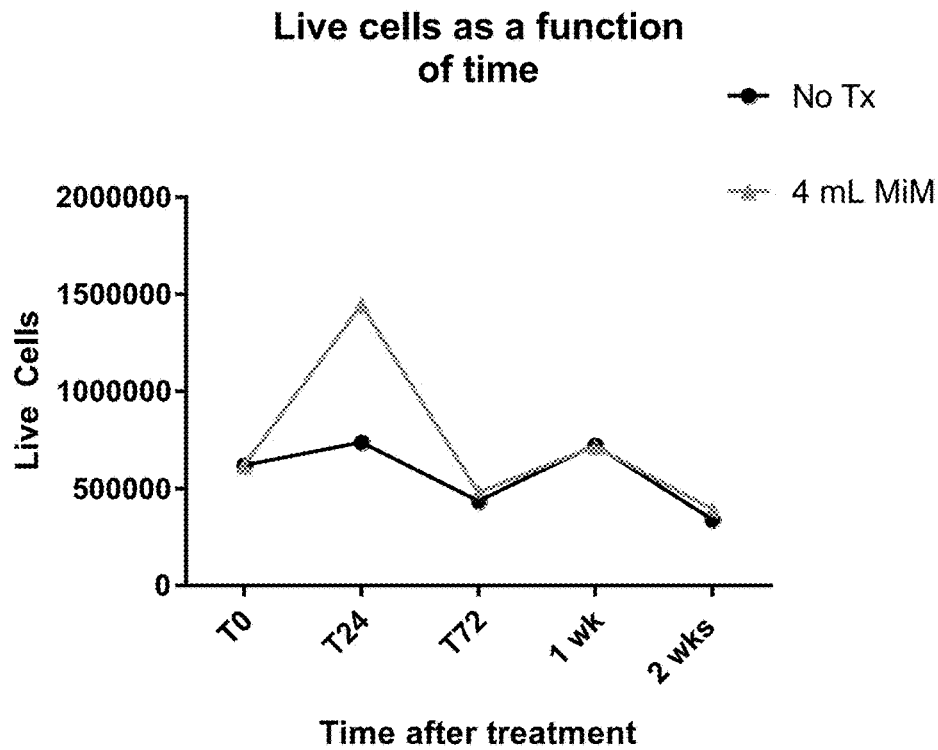

In some exemplary methods, to assess the ability of an exemplary formulation disclosed herein (e.g. PCT-01) to elicit a bovine immune response, cattle (n=5 per group) were treated by intranasal administration of 3 different doses of PCT-01 (2 ml, 4 ml, or 6 ml per animal, divided in two equal doses per nostril) using a nasal cannula. One additional untreated group served as a control. Prior to the initial dose, and then at 24 hours, 72 hours, 1 week and 2 weeks post administration, swabs of the throat were obtained from each animal, and the cells were removed from the swab by swirling and total cell counts obtained. As illustrated in FIGS. 17 A & B, administration of PCT-01 at the 2 highest doses (e.g. 4 ml and 6 ml) elicited a significant increase in immune cell infiltration into the nasopharynx, which peaked at about 24 h and then declined to normal levels by about 72 h after administration.

Figure 18A:
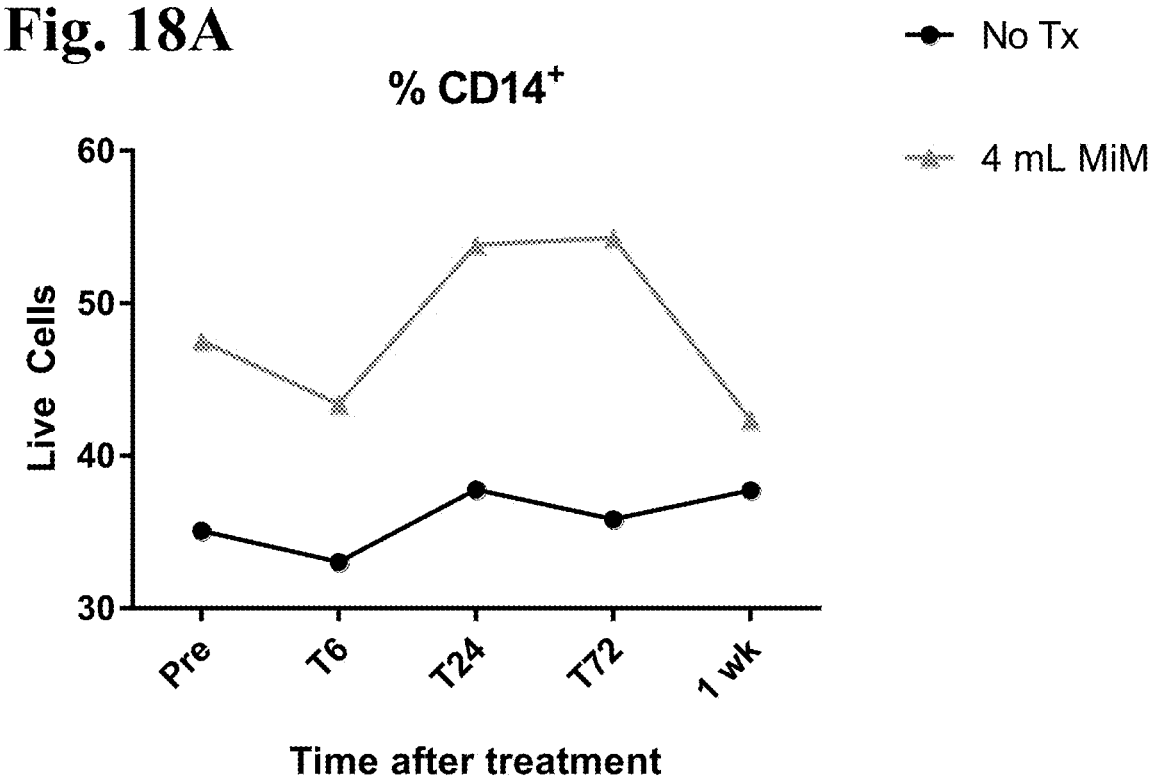
FIGS. 18A and 18B illustrate exemplary data indicating the effects of intranasal immunogenic composition (e.g., PCT-01: MIM: CLDC+CMC) administration on monocyte recruitment (FIG. 18A) and immune activation (FIG. 18B) in cells from bovine nasopharyngeal swab specimens of some embodiments disclosed herein.
Figure 18B:
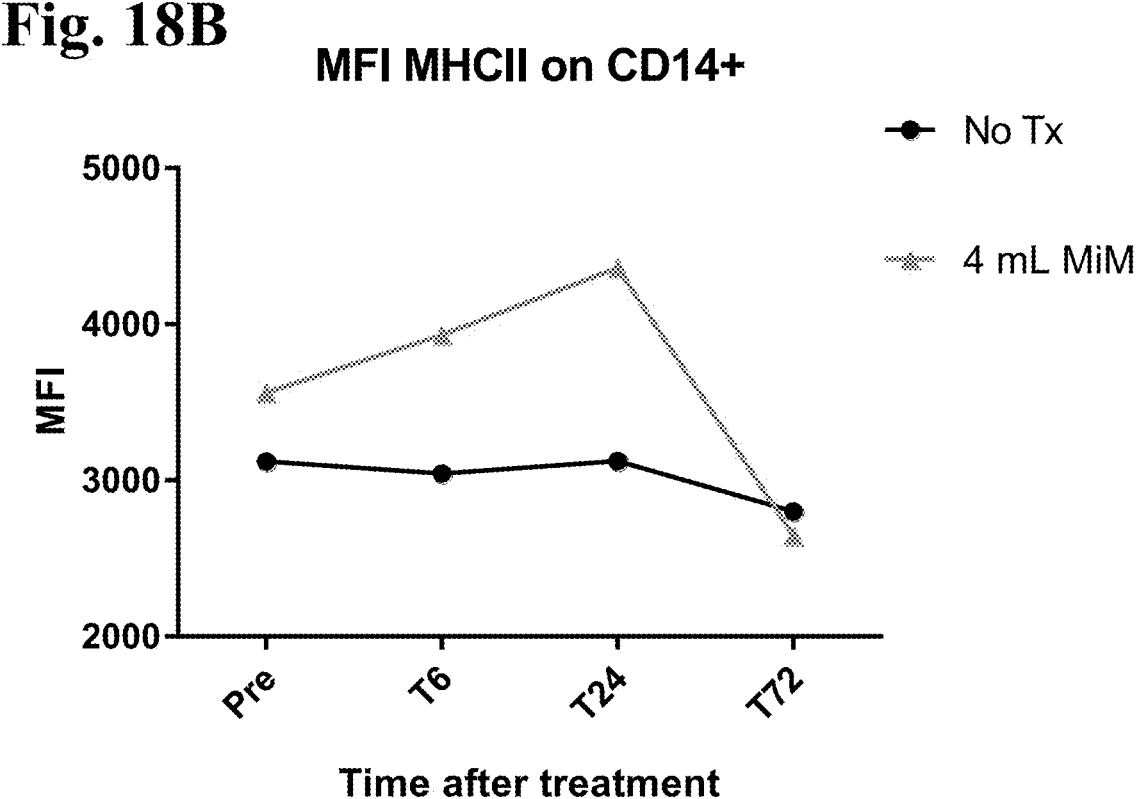

In some exemplary methods, to assess the ability of an exemplary formulation disclosed herein (e.g. PCT-01), monocyte recruitment and immune activation were analyzed after administration to the oropharynx of cows. Cattle (n=5 per group) were treated with intranasal administration PCT-01 (e.g. MiM, about 4 ml) (2 ml per nostril) (or treated with saline only as a negative control, no Tx) and infiltrates of monocytes (CD14+ cells) in the nasopharynx were assessed by throat swabs and flow cytometric analysis. In addition, the upregulation of MHCII expression (measure of immune activation) was also assessed on the CD14+ monocytes by flow cytometry. As illustrated in FIGS. 18A & 18B administration of PCT-01 elicited a sustained increase in the percentage of monocytes in the nasopharynx (FIG. 18A) compared to untreated animals, and the monocytes were also activated, as reflected by upregulation of MHCII expression (FIG. 18B).

Figure 19:
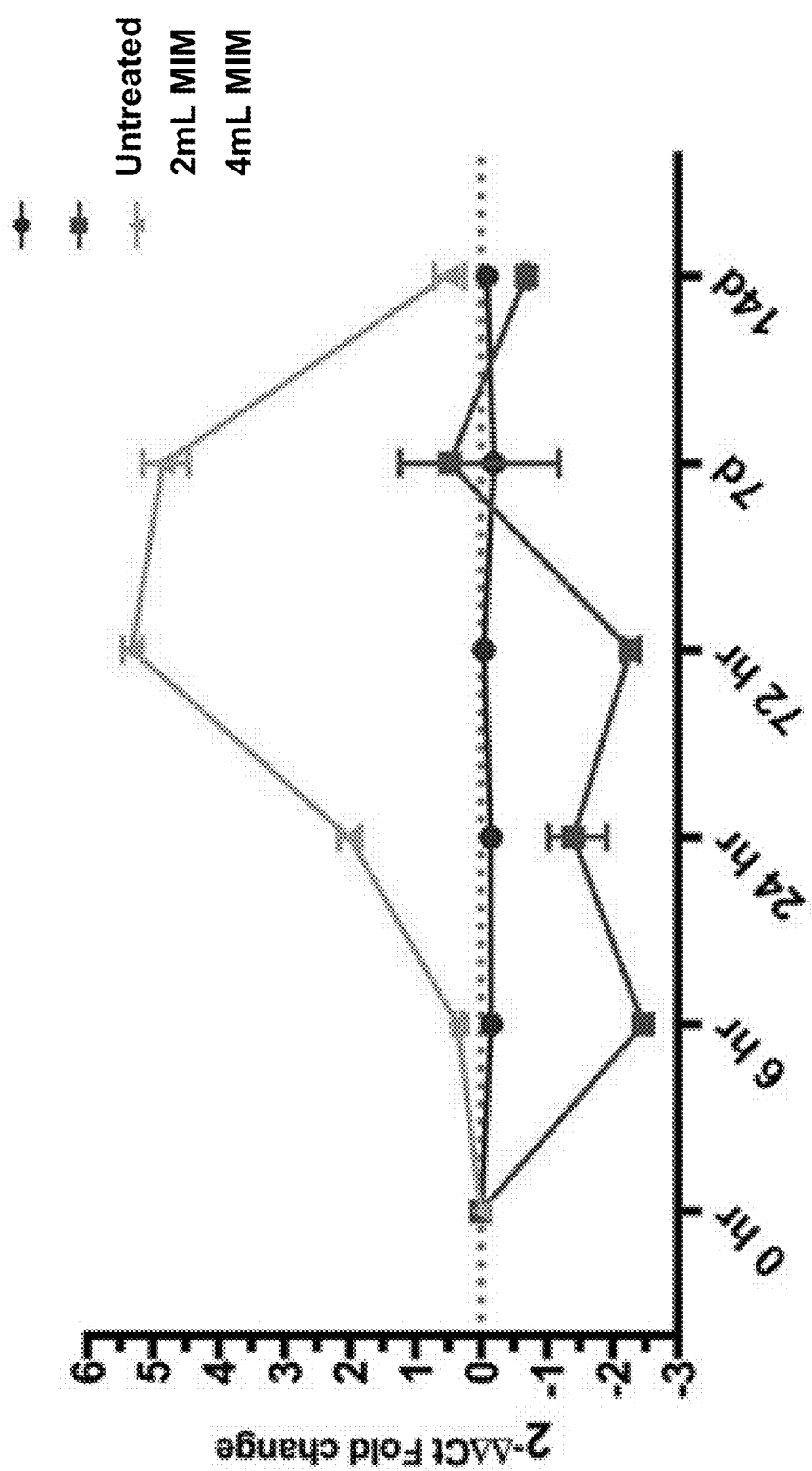
FIG. 19 illustrates exemplary qRT-PCR data indicating intranasal administration of an immunogenic composition (e.g., PCT-01: MIM: CLDC+CMC) stimulates production of the cytokine IL-8 by cells in the nasopharynx of cattle of some embodiments disclosed herein.
Figure 20:
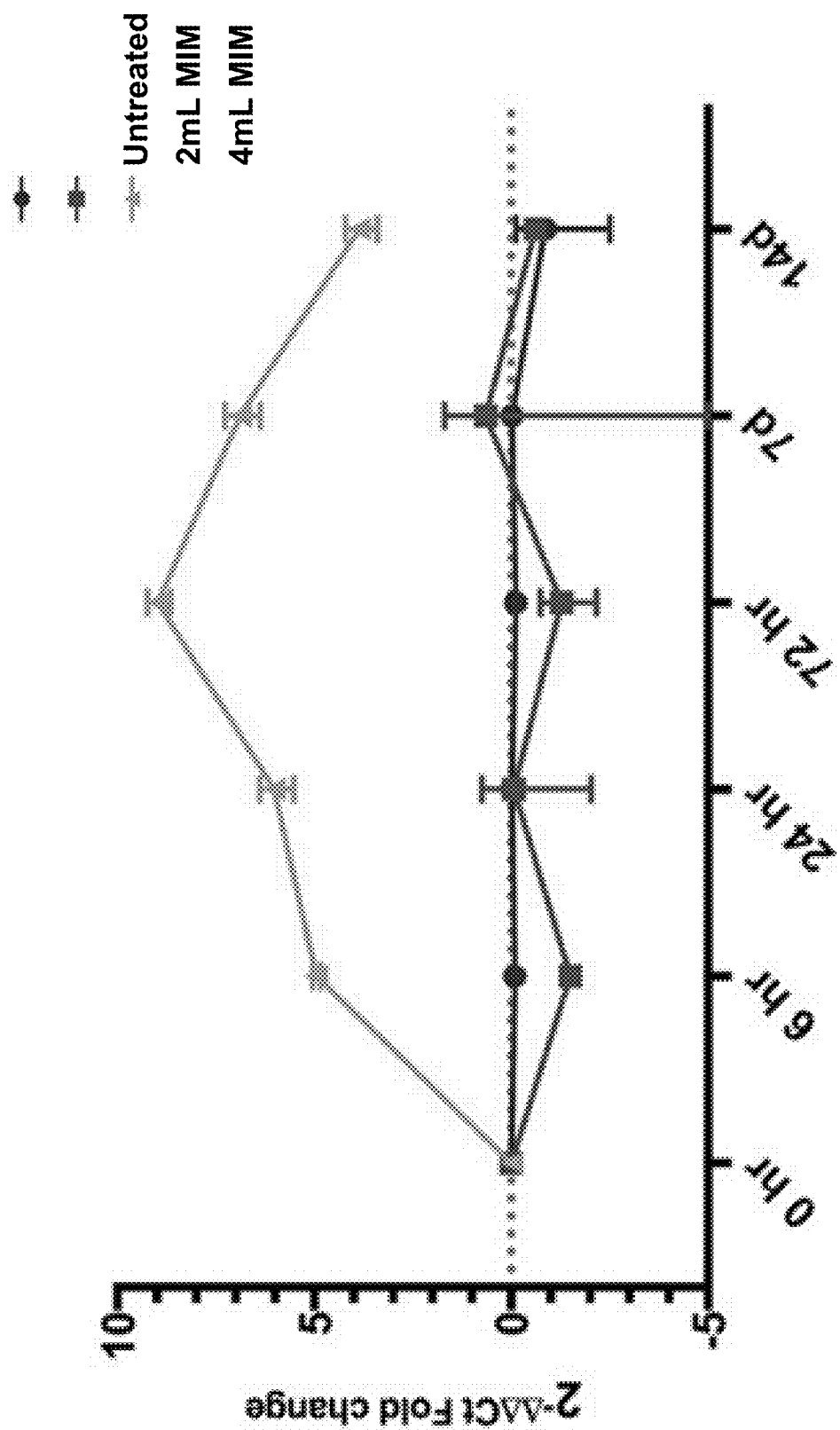
FIG. 20 illustrates exemplary qRT-PCR data indicating intranasal administration of an immunogenic composition (e.g., PCT-01: MIM: CLDC+CMC) stimulates production of the cytokine MCP-1 by cells in the nasopharynx of cattle of some embodiments disclosed herein.
Figure 21:
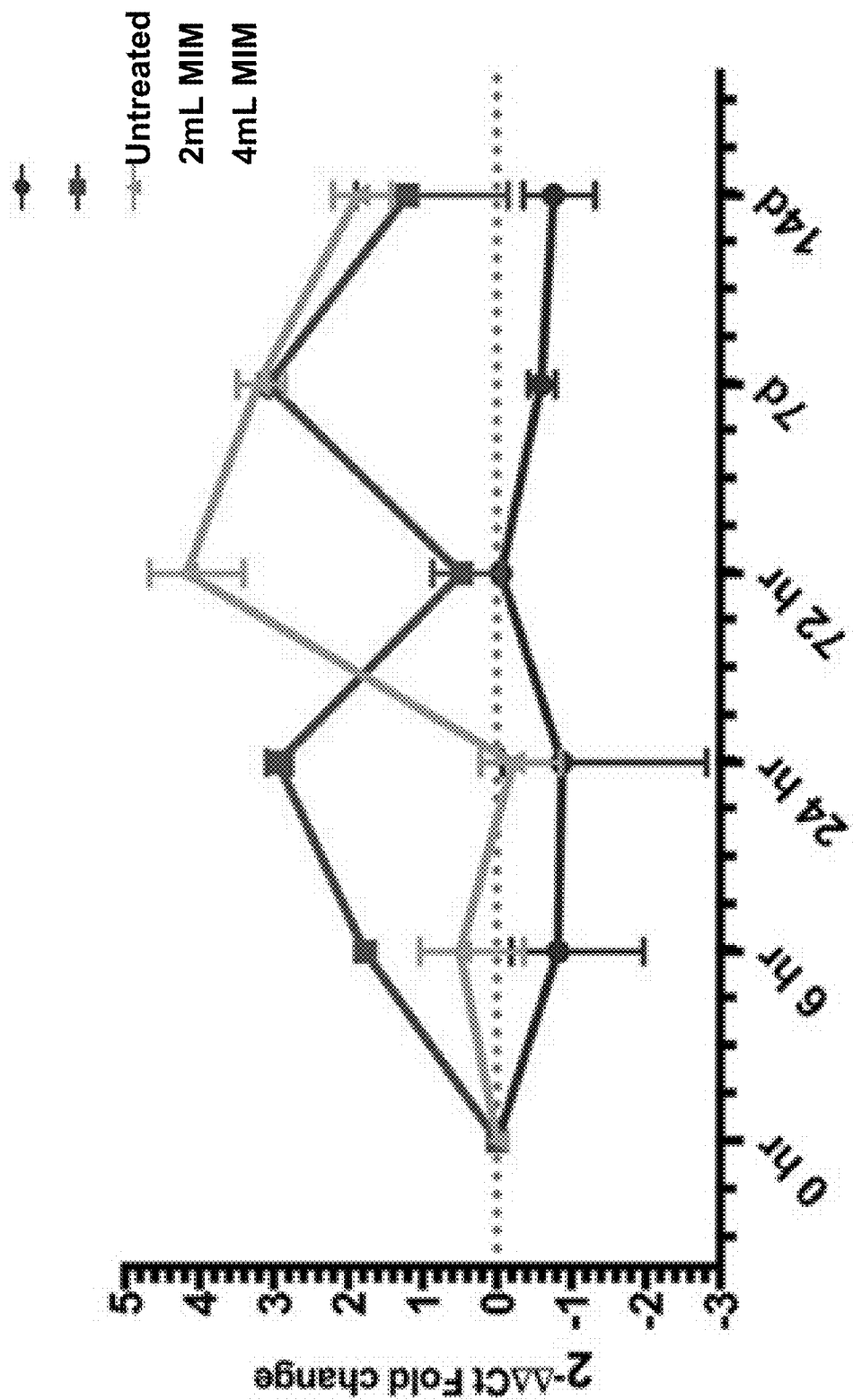
FIG. 21 illustrates exemplary qRT-PCR data indicating intra-nasal administration of an immunogenic composition (e.g., PCT-01: MIM: CLDC+CMC) stimulates production of the cytokine IFN-γ by cells in the nasopharynx of cattle of some embodiments disclosed herein.

In some exemplary methods, to assess the ability of an exemplary formulation disclosed herein (e.g. PCT-01), to test the ability of PCT-01 to stimulate bovine cytokine production as markers of an enhanced immune response, cattle (n=5 per group) were administered PCT-01 intranasally (e.g. 2 ml or 4 ml) and cells obtained by nasopharyngeal swabbing were evaluated using qRT-PCR for cytokine expression. Several cytokine markers were evaluated for enhanced expression. FIG. 19 illustrates administration of PCT-01 (e.g. 4 ml) resulted in sustained expression of mRNA for cytokine IL-8 in nasopharyngeal cells for up to 14 days. FIG. 20 illustrates that administration of PCT-01 (e.g. 4 ml) resulted in sustained expression of mRNA for cytokine MCP-1 in nasopharyngeal cells for up to 14 days. FIG. 21 illustrates that administration of PCT-01 (e.g. 4 ml) resulted in sustained expression of mRNA for cytokine IFN-γ in nasopharyngeal cells for up to 14 days.

Example 9

Figure 22A:
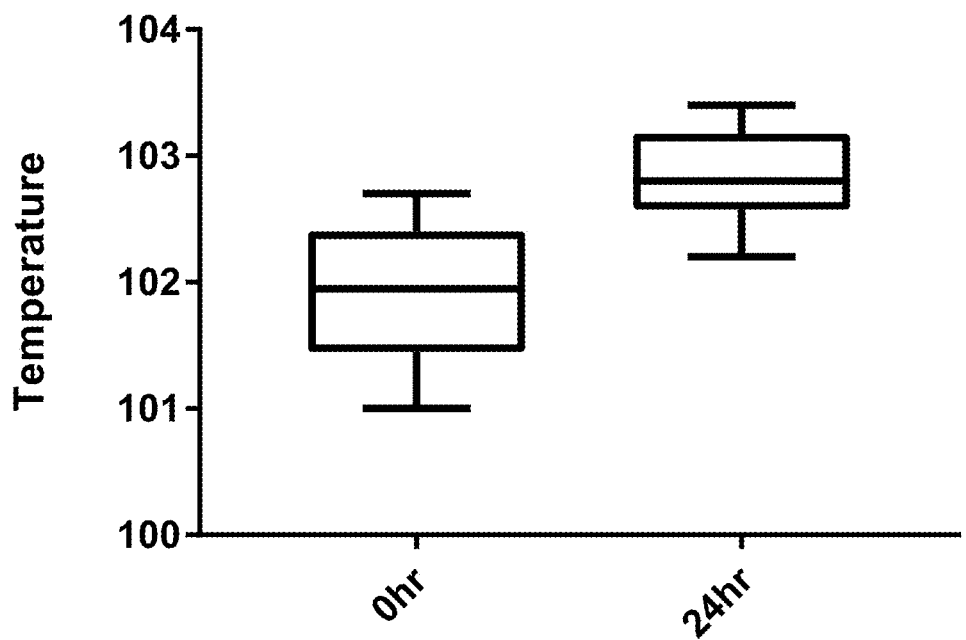
FIGS. 22A and 22B illustrates exemplary body temperature data in cattle following administration of an immunogenic composition (e.g., PCT-01: MIM: CLDC+CMC) (22A) or Zelnate™ (22B) of some embodiments disclosed herein.
Figure 22B:
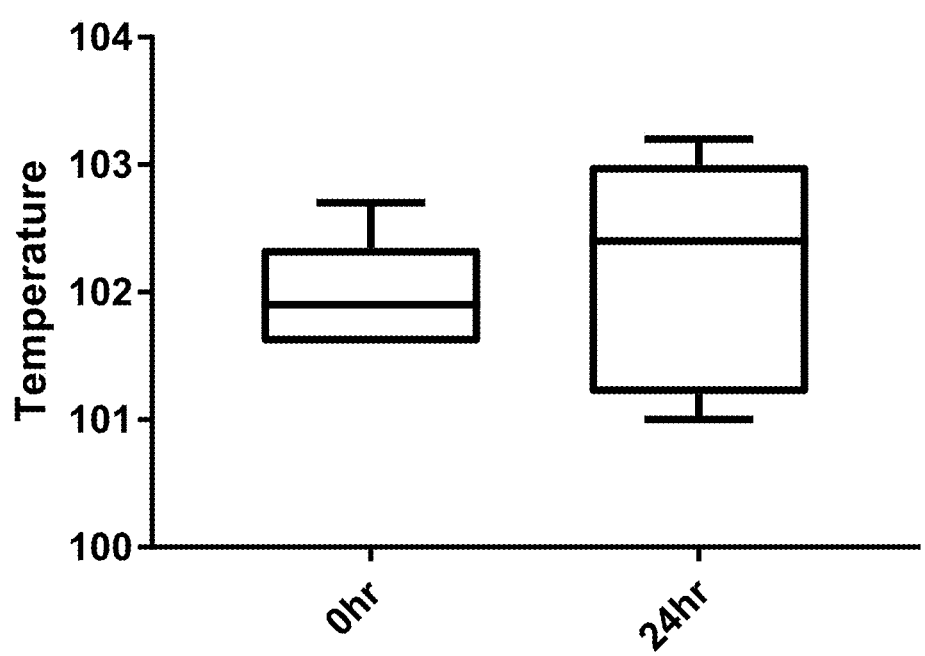
Figure 23:
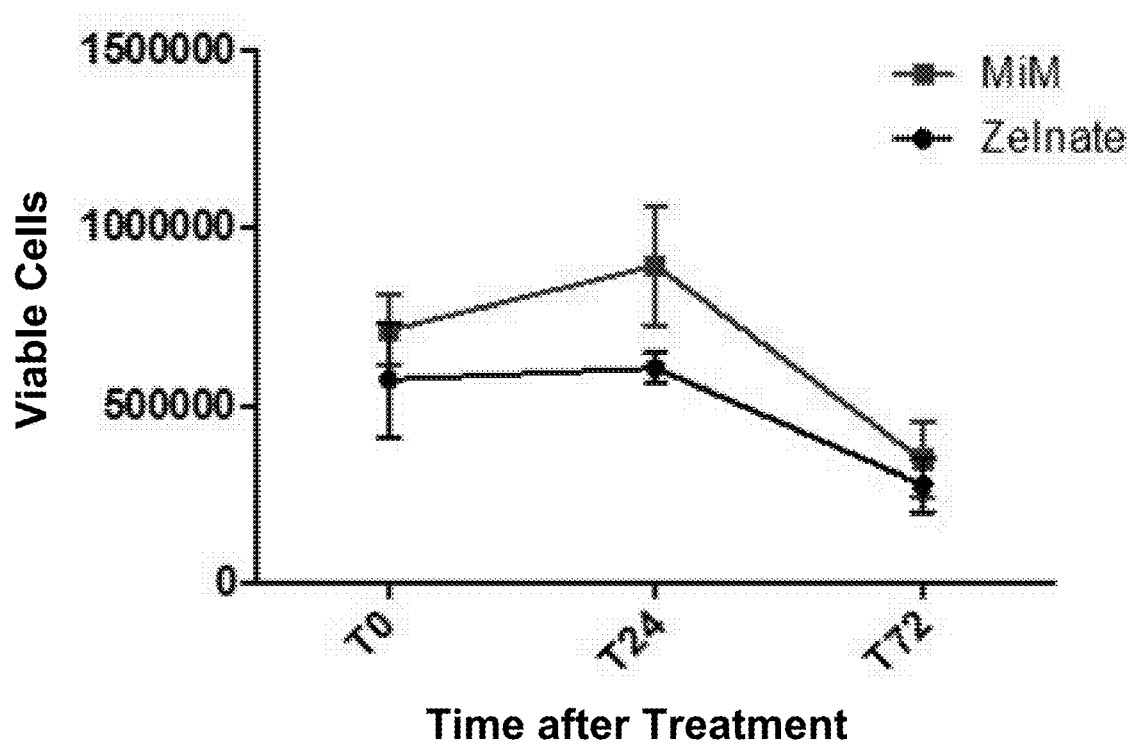
FIG. 23 illustrates exemplary data comparing immune activation of monocytes, as measured by total cell count, in the nasopharynx of cattle following intranasal administration of an immunogenic composition (e.g., PCT-01: MIM: CLDC+CMC) or intramuscular administration of Zelnate™ of some embodiments disclosed herein.
Figure 24:
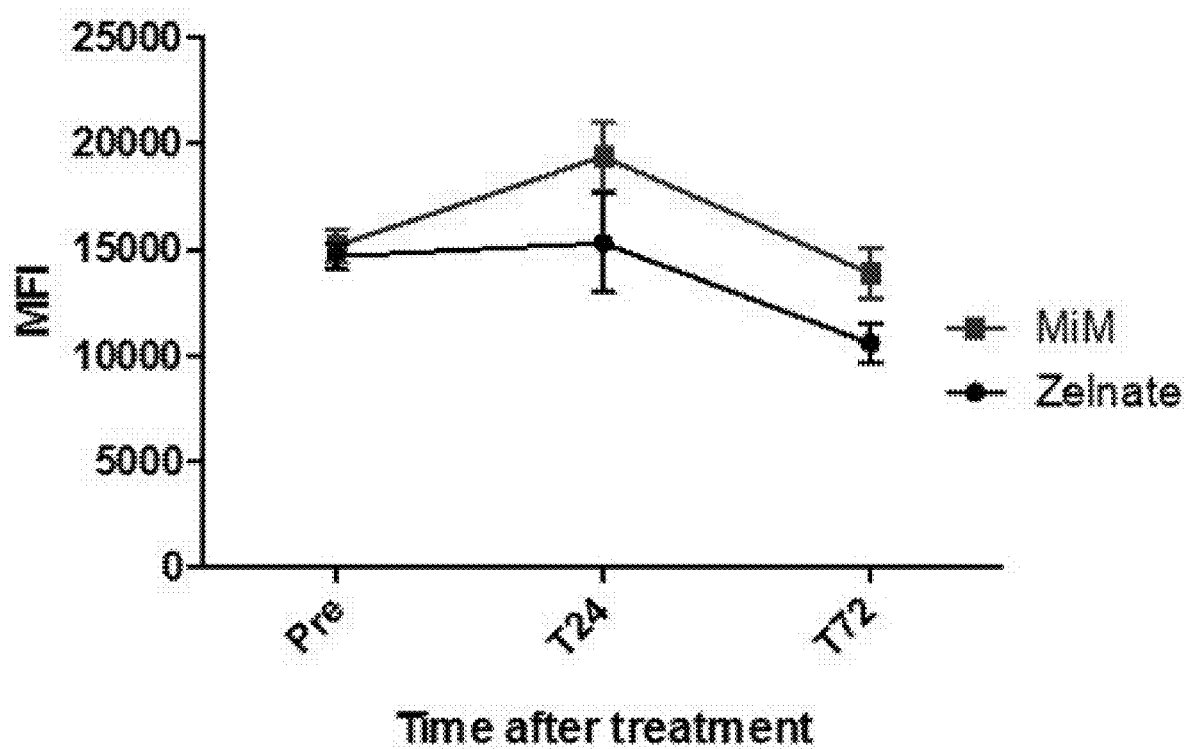
FIG. 24 illustrates exemplary data comparing immune activation of monocytes, as measured by upregulation of MHCII, in the nasopharynx of cattle following intranasal administration of an immunogenic composition (e.g., PCT-01: MIM: CLDC+CMC) or intramuscular administration of Zelnate™ of some embodiments disclosed herein.
Figure 25:
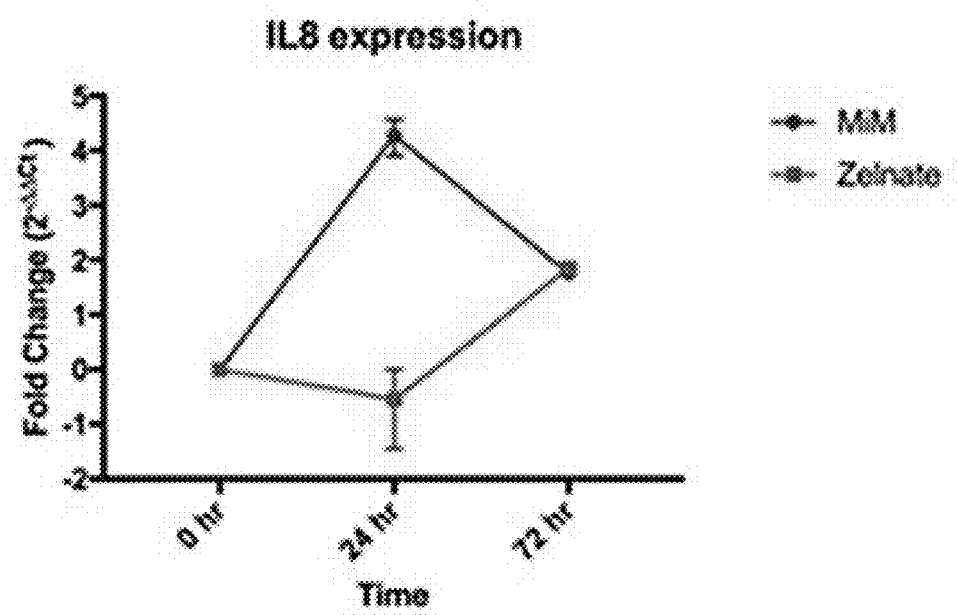
FIG. 25 illustrates exemplary qRT-PCR data from cattle indicating increased IL-8 expression by an immunogenic composition (e.g., PCT-01: MIM: CLDC+CMC) treatment, compared to Zelnate™ treatment of some embodiments disclosed herein.
Figure 26:
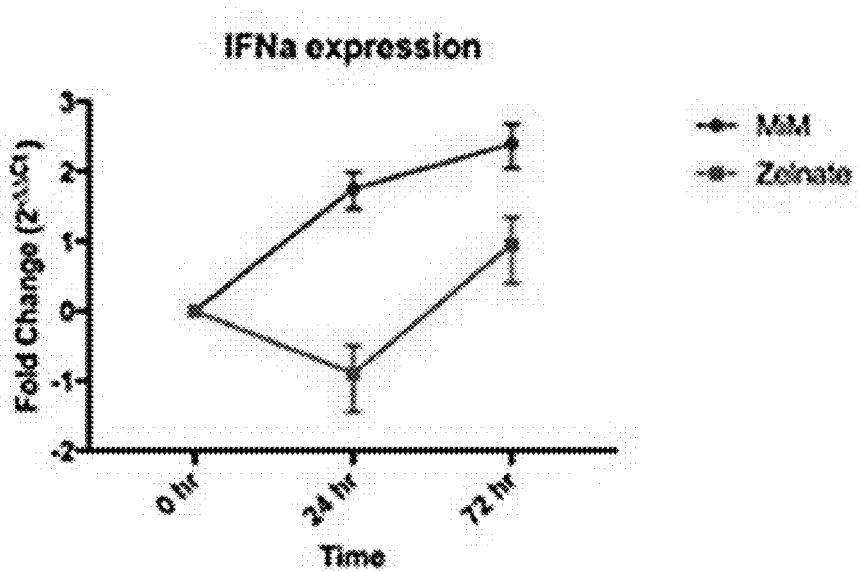
FIG. 26 illustrates an exemplary qRT-PCR data from cattle indicating increased INF-α expression by an immunogenic composition (e.g., PCT-01: MIM: CLDC+CMC) treatment, compared to Zelnate™ treatment of some embodiments disclosed herein.
Figure 27:
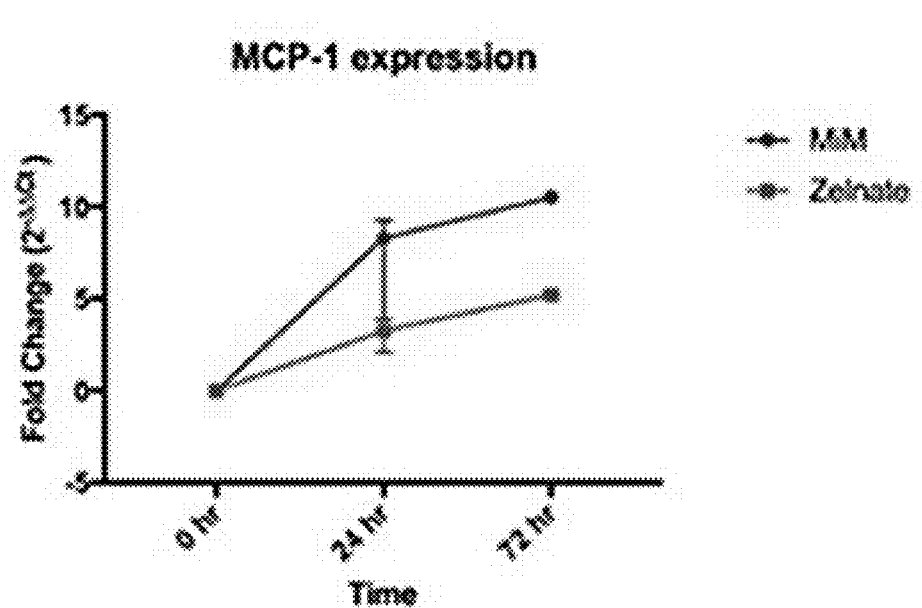
FIG. 27 illustrates an exemplary qRT-PCR data from cattle indicating increased MCP-1 expression by an immunogenic composition (e.g., PCT-01: MIM: CLDC+CMC) treatment, compared to Zelnate™ treatment of some embodiments disclosed herein.

In some exemplary methods, to assess the ability of an exemplary formulation disclosed herein (e.g. PCT-01), to evaluate the ability of PCT-01 to induce an enhanced immune response relative to other immune stimulants known in the art, two groups of cattle (n=5) were administered either PCT-01 (e.g. 4 ml/2 mL per nostril) or Zelnate™ (I.M. per manufacturer guidance) and the immune response was measured; for example, prior to treatment, 24 hours post-treatment and 72 hours post-treatment. FIGS. 22 A & B illustrate that after 24 hours, PCT-01 treatment (FIG. 22A) yielded a larger increase in body temperature than Zelnate™ treatment (FIG. 22B). FIG. 23 illustrates data from flow cytometry analysis of nasopharyngeal swabs indicating greater upregulation of WWII expression by monocytes (CD14+) in PCT-01 treated groups than in Zelnate treated groups. FIG. 24 illustrates exemplary data from qRT-PCR studies indicating IL-8 expression was upregulated more when administered PCT-01 compared to Zelnate™ administration. Furthermore, PCT-01 administration produced a much more rapid upregulation of IL-8 than did the commercially available composition, Zelnate™. qRT-PCR was also used to assess INF-α expression following PCT-01 and Zelnate™ administration. FIG. 16 shows INF-α expression was upregulated to a much greater degree by PCT-01 administration compared to Zelnate™ administration. It was observed that PCT-01 administration produced a more rapid upregulation of INF-α when compared to Zelnate™ administration. qRT-PCR studies were also performed to assess MCP-1 expression. FIG. 27 illustrates that PCT-01 produced a more robust induction of MCP-1 than administration of Zelnate™. Taken together, these data indicate that relative to a commercially available formulation Zelnate™, PCT-01 produces a significantly greater non-specific enhanced immune response.

Example 10

Figure 28:
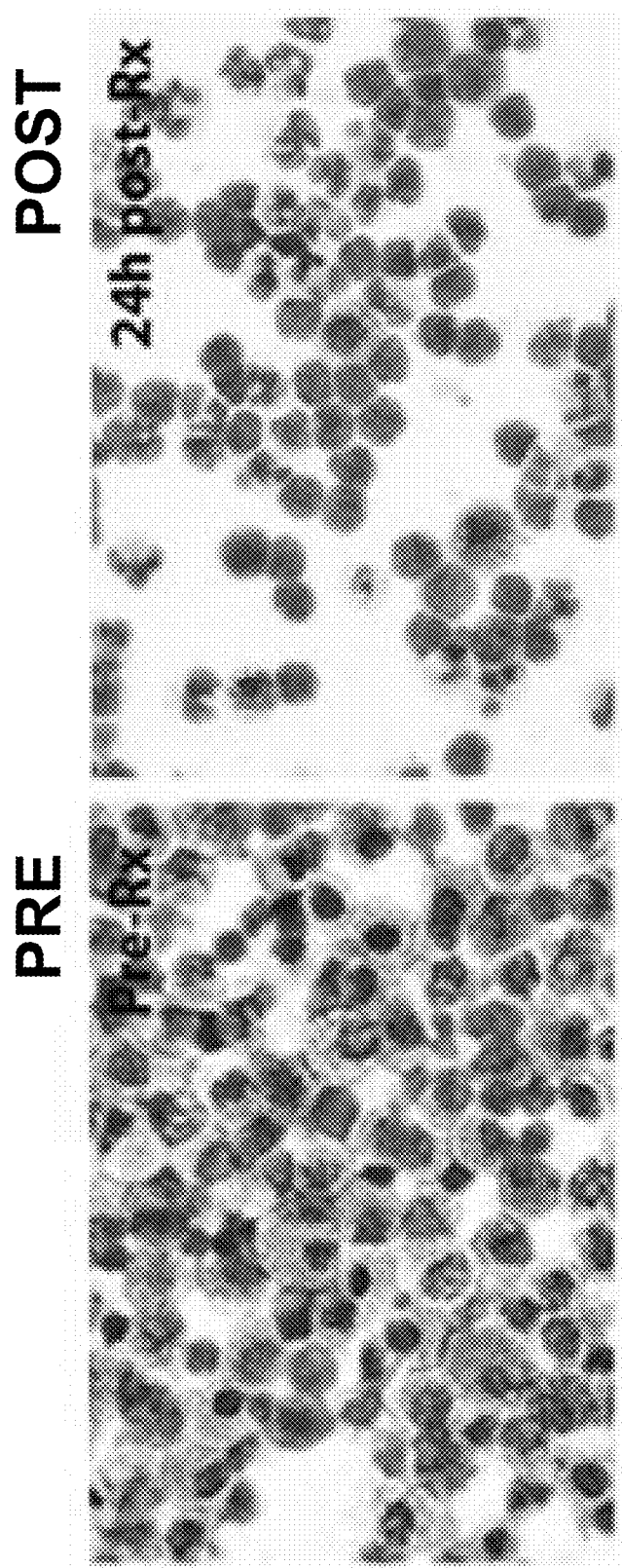
FIG. 28 illustrates exemplary images demonstrating increased infiltration of lymphocytes in milk samples following intramammary infusion of an immunogenic composition (e.g., PCT-01: MIM: CLDC+CMC) in dairy cattle of some embodiments disclosed herein.

In another exemplary method, in order to assess the immunological impact of an exemplary formulation disclosed herein (e.g. PCT-01), dairy cattle (n=5) were administered by infusion in one quarter of the mammary gland using PCT-01 (1 ml diluted in PBS). Pre-treatment lavage samples were obtained from the treated animal quarter 7d before infusion (pre-Rx) and then at 24 h, 72 h, and 7 days after PCT-01 infusion. As illustrated in FIG. 28, milk samples were evaluated cytologically for a cellular response to PCT-01 infusion, and demonstrated an influx of mononuclear cells (T cells) into the infused mammary gland quarter. These results are indicative of local induction of mammary gland immunity by PCT-01.

Example 11

Figure 29:
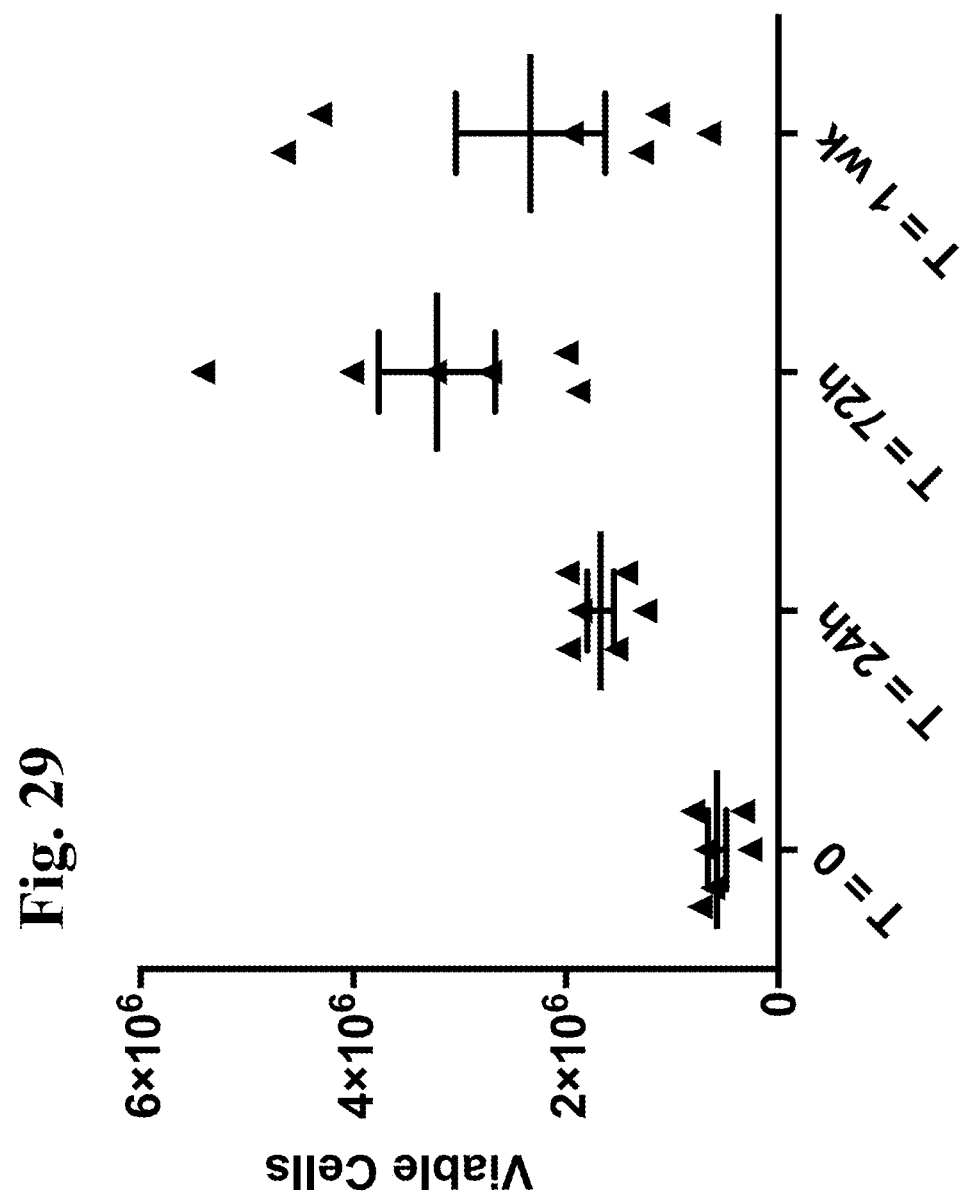
FIG. 29 illustrates exemplary cell count data demonstrating the cellular responses in the nasopharynx of goats following intranasal administration of an immunogenic composition (e.g., PCT-01: MIM: CLDC+CMC) of some embodiments disclosed herein.

In another exemplary method, in order to assess the immunological impact of an exemplary formulation disclosed herein (e.g. PCT-01), goats were administered PCT-01. Nasopharyngeal swabs were obtained from healthy adult goats (n=6) before PCT-01 administration and at 24 h, 72 h, and 7 days after treatment. As illustrated in FIG. 29, cell counts were determined from swab samples, and were found to be significantly increased at 72 h and 7 days after treatment.

Figure 30A:
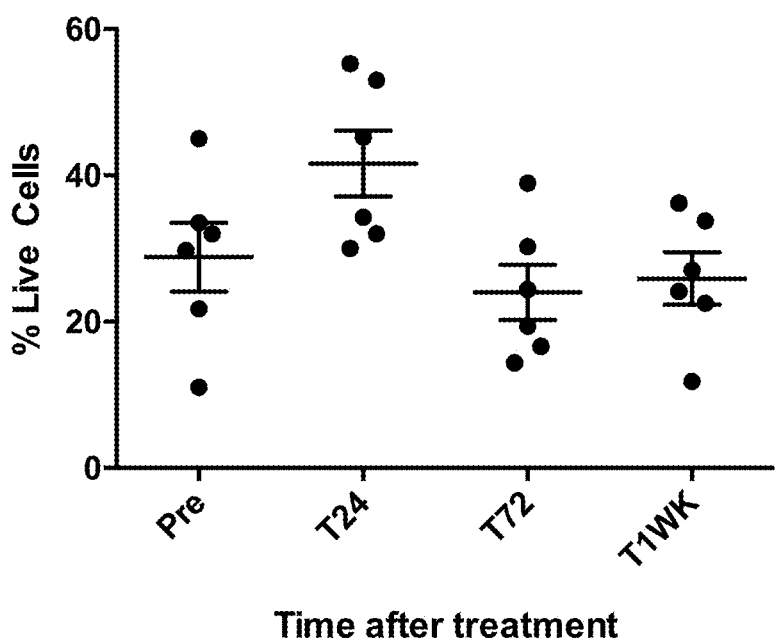
FIGS. 30A and 30B illustrate exemplary monocyte responses, as measured by cell count (30A), and cellular activation (30B), as measured by MHCII upregulation, following an immunogenic composition (e.g., PCT-01.
Figure 30B:
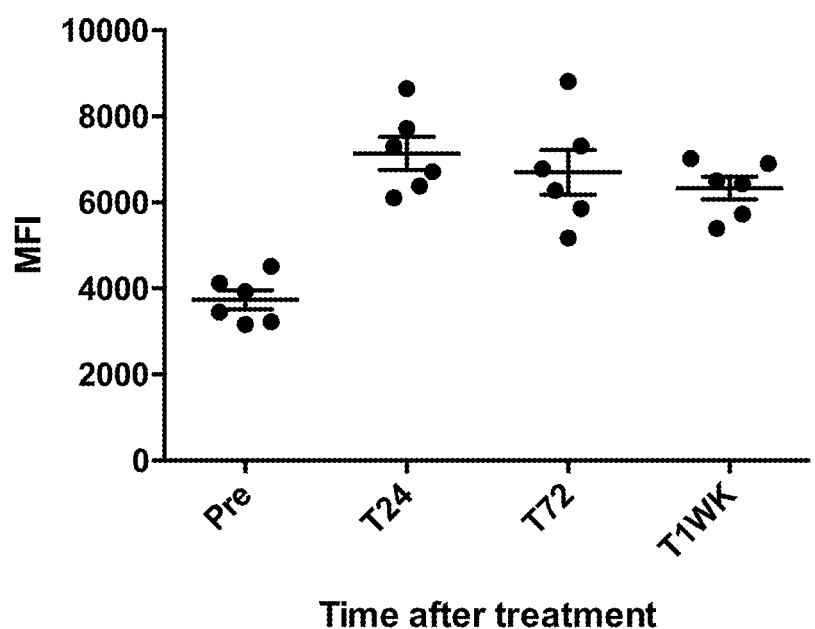

In another exemplary method, in order to assess the immunological impact of an exemplary formulation disclosed herein (e.g. PCT-01) on monocyte response and cellular activation, monocyte infiltration and MHCII upregulation were assessed post administration. As illustrated in FIG. 30A, percentages of CD14+ monocytes were determined from nasopharyngeal swabs samples post-treatment, and were found to be significantly increased 24 h after treatment. As illustrated in FIG. 30B, monocytes were found to be significantly activated (higher MHCII expression) at all post-treatment time points evaluated, indicative of sustained immune activation. In addition, as illustrated in FIG. 31, CD8 T cells were found to be significantly increased in nasopharynx swabs from goats following treatment.

As illustrated in FIG. 32, PCT-01 administration results in an increased percentage of γδ-T cells in goat cultured PBMC cells compared to controls. Blood leukocytes from healthy goats were placed in triplicate wells (e.g. 96-well plates in 100 μl complete medium) and PCT-01 was added to the wells, and the cultures were incubated for 48 h, at which point the cells were collected and immunostained for evaluation of cellular responses using, for example, flow cytometry. The results indicated that PCT-01 induced an increase in γδ-T cells in cultured goat leukocytes, compared to control cells not exposed to the immunogenic agent.

Example 12

In some exemplary methods, a starting material is referred to as previously disclosed immunogenic composition, MucosImmune (MiM), and further includes a high viscosity carboxymethylcellulose (CMC). In these examples, MiM is mixed 50/50 v/v with 1% solution of high viscosity CMC to create a product (referred to as Ocummune). Addition of high viscosity CMC increases viscosity of Ocummune to gel-like consistency (typically, MiM is essentially a liquid). By adding the high viscosity agent, contact time is increased with the cornea and can assist with reducing corneal pain sensitivity. In other exemplary methods, a starting material is MucosImmune (MiM) and high molecular weight/high viscosity carboxymethylcellulose (CMC) MW=700 KDa of high viscosity (Sigma). In other exemplary methods, MiM can be mixed 50/50 v/v with 2% solution of high viscosity CMC to create final product (Ocummune) with final high viscosity CMC concentration of 1%. In some exemplary methods, Ocummune has a similar consistency to that of Surgilube™ (e.g. a common lube for placing urinary or nasopharyngeal catheters).

In one exemplary method, in order to assess the immunological impact of an exemplary immunogenic formulation disclosed herein on chronic ocular infection in a subject, experimental protocols were applied to an animal model (e.g. cats) having chronic ocular herpes virus infection. A cat was observed pre-treatment having a chronic ocular herpesvirus infection and then treated with MiM further including a high viscosity carboxymethylcellulose additive (e.g. Sigma about 500 to 1,000 kDa such as 700 kDa carboxymethylcellulose, salt, high viscosity CMC) termed Ocummune. In one exemplary experiment, safety of the novel formulation was tested on mice and demonstrated no adverse effects following topical application of the immunogenic composition. Within 4 days of treatment, the cat demonstrated significantly improved infection (FIGS. 35A and 35B). In this experiment, it was observed that the clinical response after the immunogenic composition was used to treat the cat was significant. Within 4 days of treatment, the cat responded where the infection herpesvirus keratoconjunctivitis was previously refractory to standard treatments. In this experiment, treatment was applied once daily as a single drop to each eye. Substantial improvement was observed within 48 hr of treatment, and the animal has continued to have improvement in ocular signs for at least 3 months.

Example 13

In another exemplary method, in order to assess the immunological impact of an exemplary immunogenic formulation disclosed herein on an eye-related cancer in a subject, experimental protocols were applied to an animal model (e.g. horses) having corneal cancer. Horses having corneal cancer were observed pre-treatment having eye tumors and then post treatment: at 2 weeks, 4 weeks and 6 weeks with MiM further including a high viscosity carboxymethylcellulose additive (e.g. Sigma about 500 to 1,000 kDa such as 700 kDa carboxymethylcellulose, salt) termed Ocummune. Within 2 weeks of treatment, positive responses were observed in 5 of 7 treated horses. No adverse effects observed. At 4 weeks, positive responses were observed where essentially no tumor remained in the cornea of 5 of 7 horses. At 6 weeks, positive results were continued to be observed. (See for example, FIG. 36A to 36D). In this experiment, it was observed that the clinical response after the immunogenic composition was used to treat eye tumors in a horse were significant. It was also observed that the horses were less sensitive to the treatment compared to other commercially available products, for example, by reducing pain associated with the tumors and tumor regression. In this exemplary method, horses were treated every other day (e.g. 2-3 drops) of the eye product to the affected eye. In some animals, the ocular immunotherapy material was also injected into the larger cancer lesions, for two injections at 1-week intervals.

In another exemplary method, in order to assess the immunological impact of an exemplary immunogenic formulation disclosed herein on corneo-limbal squamous cell carcinoma (SCC) in a subject, experimental protocols were applied to an animal model (e.g. horses) having corneo-limbal SCC. Horses having this cancer were observed pre-treatment having eye tumors and then post treatment: at 2 weeks, 4 weeks and 6 weeks with MiM further including a high viscosity carboxymethylcellulose additive (e.g. Sigma about 500 to 1,000 kDa such as 700 kDa carboxymethylcellulose, salt) termed Ocummune. The horses (2 horses) were treated by topical application only. Within 2 weeks of treatment, positive responses were observed in both treated horses. No adverse effects observed. At 2-4 weeks, positive responses were observed where essentially no tumor remained in the cornea of 5 of 7 horses. At 6 weeks, positive results were continued to be observed. (See for example, FIG. 37A to 37D). In this experiment, it was observed that the clinical response after the immunogenic composition was used to treat eye tumors in a horse were significant. It was also observed that the horses were less sensitive to the treatment compared to other commercially available products, for example, by reducing pain associated with tumors and side effects due to tumor regression (e.g. chronic wounds) In this exemplary method, horses were treated every other day (e.g. 2-3 drops) of the eye product to the affected eye. In some animals, the ocular immunotherapy material was also injected into the larger cancer lesions, for two injections at one-week intervals.

All of the COMPOSITIONS and METHODS disclosed and claimed herein may be made and executed without undue experimentation in light of the present disclosure. While the COMPOSITIONS and METHODS have been described in terms of preferred embodiments, it will be apparent to those of skill in the art that variation may be applied to the COMPOSITIONS and METHODS and in the steps or in the sequence of steps of the METHODS described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An immunogenic composition comprising:
   (a) cationic liposomes, wherein the cationic liposomes comprise a mixture of cationic lipids and non-charged lipids;
   (b) a mixture of toll like receptor 3 (TLR3) and toll like receptor 9 (TLR9) ligands;
   (c) a cellular adhesion agent having a high viscosity; and
   (d) further comprising a cellular adhesion agent of low- to mid-weight viscosity.

2. The composition according to claim 1, wherein the cationic liposomes comprise a mixture of cationic lipid and non-charged lipids.

3. The composition according to claim 2, wherein the mixture comprises non-coding plasmid DNA and polyI:C.

4. The composition according to claim 3, wherein the non-coding plasmid DNA comprises a polynucleotide represented by SEQ ID NO: 1.

5. The composition according to claim 2, wherein the mixture comprises plasmid DNA and polyI:C in about a 1:1 ratio (by weight).

6. The composition according to claim 2, wherein the mixture of cationic lipid and non-charged lipids further comprises DOTAP and cholesterol in a 1:1 molar ratio.

7. The composition according to claim 1, wherein the high viscosity cellular adhesion agent comprises one or more of carboxymethylcellulose, chitosan, polyglycol, a poloxamer or hyaluronan.

8. The composition according to claim 1, wherein the high viscosity cellular adhesion agent is carboxymethylcellulose.

9. The composition according to claim 1, further comprising a protein antigen derived from a pathogen.

10. The composition according to claim 1, wherein the composition is a gel-like consistency capable of drop-wise delivery.

11. The composition according to claim 1, wherein the composition comprises a pharmaceutical composition and further includes a pharmaceutically acceptable excipient.

12. A kit comprising the composition according to claim 1 and at least one container.

13. The kit according to claim 12, further comprising an eye delivery device.

14. A method for inducing a non-specific immune response in a subject, comprising administering to the subject a composition according to claim 1.

15. The method according to claim 14, wherein the subject has an eye disorder.

16. The method according to claim 15, wherein the eye disorder comprises cancer, an infection or an ulcer.

17. The method according to claim 15, wherein the eye disorder comprises a condition of the cornea.

18. The method according to claim 14, wherein administering comprises administering dropwise to the affected area or region or administering as an ointment or cream.

19. The method according to claim 14, wherein the subject is a human, other mammal, bird, or fish.

20. The method according to claim 14, wherein the subject is a pet or livestock.

* * * * *